(12) United States Patent
Hirsh et al.

(10) Patent No.: US 11,247,069 B2
(45) Date of Patent: Feb. 15, 2022

(54) METHODS AND DEVICES FOR TREATING VASCULAR RELATED DISORDERS

(71) Applicant: LuSeed Vascular Ltd., Tel-Aviv (IL)

(72) Inventors: Nitzan Hirsh, Tel Aviv (IL); Amir Arthur, Rishon LeTsion (IL)

(73) Assignee: LuSeed Vascular Ltd., Tel-Aviv (IL)

( * ) Notice: Subject to any disclaimer, the term of this patent is extended or adjusted under 35 U.S.C. 154(b) by 0 days.

(21) Appl. No.: 16/469,666

(22) PCT Filed: Dec. 15, 2017

(86) PCT No.: PCT/IB2017/057989
§ 371 (c)(1),
(2) Date: Jun. 14, 2019

(87) PCT Pub. No.: WO2018/109733
PCT Pub. Date: Jun. 21, 2018

(65) Prior Publication Data
US 2020/0078602 A1 Mar. 12, 2020

Related U.S. Application Data

(60) Provisional application No. 62/481,500, filed on Apr. 4, 2017, provisional application No. 62/434,629, filed on Dec. 15, 2016.

(51) Int. Cl.
*A61N 5/10* (2006.01)
*A61F 2/915* (2013.01)

(52) U.S. Cl.
CPC .......... *A61N 5/1002* (2013.01); *A61N 5/103* (2013.01); *A61F 2/915* (2013.01); *A61N 2005/1003* (2013.01); *A61N 2005/1004* (2013.01)

(58) Field of Classification Search
CPC .......... A61N 5/1002; A61N 2005/1003–1005; A61N 2005/1024
See application file for complete search history.

(56) References Cited

U.S. PATENT DOCUMENTS

| 5,498,227 A * | 3/1996 | Mawad ............... A61N 5/1002 600/3 |
| 6,190,303 B1 | 2/2001 | Glenn et al. |
| 6,261,320 B1 | 7/2001 | Tam et al. |
| 6,626,928 B1 * | 9/2003 | Raymond ........ A61B 17/12022 600/3 |
| 2001/0001806 A1 | 5/2001 | Turnlund et al. |

(Continued)

FOREIGN PATENT DOCUMENTS

| WO | WO 2018/109733 | 6/2018 |
| WO | WO 2018/109733 A3 | 6/2018 |

OTHER PUBLICATIONS

International Preliminary Report on Patentability dated Jun. 27, 2019 From the International Bureau of WIPO Re. Application No. PCT/IB2017/057989. (8 Pages).

(Continued)

*Primary Examiner* — Thaddeus B Cox

(57) ABSTRACT

A method of treatment including: selecting tissue to be exposed to radiation for gradual closure of one or more blood vessel within the tissue to be exposed radiation; selecting radiation levels to promote gradual constriction of the one or more vessel; exposing the tissue to be exposed radiation to selected radiation levels.

27 Claims, 40 Drawing Sheets

(56) References Cited

U.S. PATENT DOCUMENTS

| | | |
|---|---|---|
| 2001/0056219 A1 | 12/2001 | Brauckman et al. |
| 2002/0065448 A1 | 5/2002 | Bradshaw et al. |
| 2003/0065242 A1 | 4/2003 | Dinkelborg et al. |
| 2004/0092913 A1 | 5/2004 | Hennings et al. |
| 2005/0049508 A1* | 3/2005 | Forman ................ A61N 5/1001 600/476 |
| 2011/0066254 A1 | 3/2011 | Forsell |

OTHER PUBLICATIONS

International Search Report and the Written Opinion dated May 31, 2018 From the International Searching Authority Re. Application No. PCT/IB2017/057989. (15 Pages).

Invitation to Pay Additional Fees dated Mar. 27, 2018 From the International Searching Authority Re. Application No. PCT/IB2017/057989. (2 Pages).

Supplementary European Search Report and the European Search Opinion dated May 6, 2020 From the European Patent Office Re. Application No. 17879672.8. (8 Pages).

Communication Pursuant to Article 94(3) EPC dated Mar. 12, 2021 From the European Patent Office Re. Application No. 17879672.8. (6 Pages).

\* cited by examiner

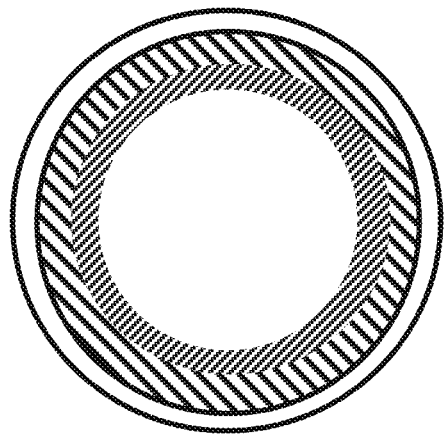
FIG. 2C
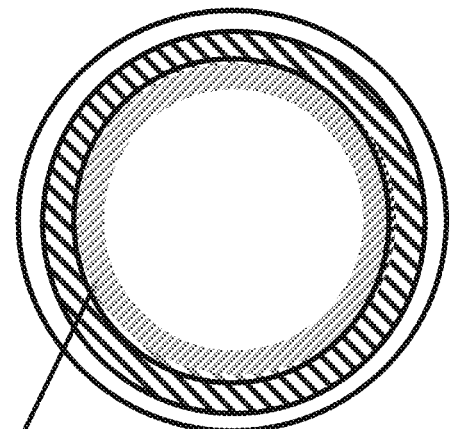
206d    FIG. 2D    207
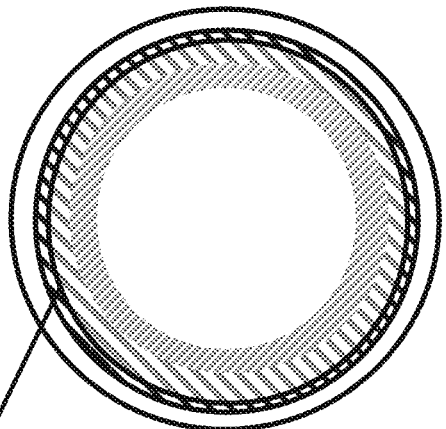
206e    FIG. 2E
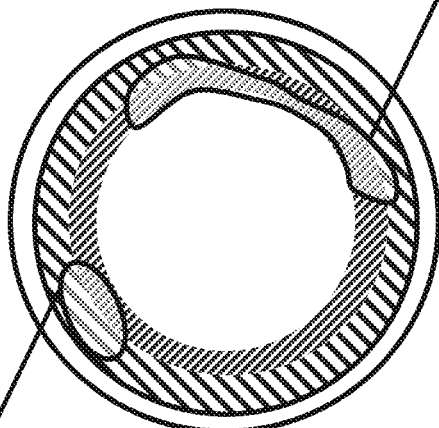
206f    FIG. 2F
 Endothelial layer
 Smooth muscle layer
 Collagen layer

| total radiation [Gy] \ radiation rate [mGy/hours] | 0 | 1 | 10 | 100 | 200 | 300 | 400 | 500 | 600 | 700 | 800 | 900 | 1000 | >1000 |
|---|---|---|---|---|---|---|---|---|---|---|---|---|---|---|
| 0.1 | x | x | x | x | x | x | x | 12secs | 10secs | 8.57secs | 7.5secs | 6.6secs | 6secs | <6 secs |
| 1 | x | x | x | x | x | x | x | 2 | 1.66667 | 1.42857 | 1.25 | 1.111111 | 1 | <1 |
| 2 | 2000 | 200 | 20 | 10 | 6.67 | 5 | 4 | 3.33333 | 2.85714 | 2.5 | 2.222222 | 2 | <2 |
| 3 | 3000 | 300 | 30 | 15 | 10 | 7.5 | 6 | 5 | 4.28571 | 3.75 | 3.333333 | 3 | <3 |
| 4 | 4000 | 400 | 40 | 20 | 13.3 | 10 | 8 | 6.66667 | 5.71429 | 5 | 4.444444 | 4 | <4 |
| 5 | 5000 | 500 | 50 | 25 | 16.7 | 12.5 | 10 | 8.33333 | 7.14286 | 6.25 | 5.555556 | 5 | <5 |
| 6 | 6000 | 600 | 60 | 30 | 20 | 15 | 12 | 10 | 8.57143 | 7.5 | 6.666667 | 6 | <6 |
| 7 | 7000 | 700 | 70 | 35 | 23.3 | 17.5 | 14 | 11.6667 | 10 | 8.75 | 7.777778 | 7 | <7 |
| 8 | 8000 | 800 | 80 | 40 | 26.7 | 20 | 16 | 13.3333 | 11.4286 | 10 | 8.888889 | 8 | <8 |
| 9 | 9000 | 900 | 90 | 45 | 30 | 22.5 | 18 | 15 | 12.8571 | 11.25 | 10 | 9 | <9 |
| 10 | - | 1000 | 100 | 50 | 33.3 | 25 | 20 | 16.6667 | 14.2857 | 12.5 | 11.11111 | 10 | <10 |
| 11 | - | 1100 | 110 | 55 | 36.7 | 27.5 | 22 | 18.3333 | 15.7143 | 13.75 | 12.22222 | 11 | <11 |
| 12 | - | 1200 | 120 | 60 | 40 | 30 | 24 | 20 | 17.1429 | 15 | 13.33333 | 12 | <12 |
| 13 | - | 1300 | 130 | 65 | 43.3 | 32.5 | 26 | 21.6667 | 18.5714 | 16.25 | 14.44444 | 13 | <13 |
| 14 | - | 1400 | 140 | 70 | 46.7 | 35 | x | x | x | x | x | x | x |
| 15 | - | 1500 | 150 | 75 | 50 | 37.5 | x | x | x | x | x | x | x |
| 16 | - | 1600 | 160 | 80 | 53.3 | 40 | x | x | x | x | x | x | x |
| 17 | - | 1700 | 170 | 85 | 56.7 | 42.5 | x | x | x | x | x | x | x |
| 18 | - | 1800 | 180 | 90 | 60 | 45 | x | x | x | x | x | x | x |
| 19 | - | 1900 | 190 | 95 | 63.3 | 47.5 | x | x | x | x | x | x | x |
| 20 | - | 2000 | 200 | 100 | 66.7 | 50 | x | x | x | x | x | x | x |
| 21 | - | 2100 | 210 | 105 | 70 | 52.5 | x | x | x | x | x | x | x |
| 22 | - | 2200 | 220 | 110 | 73.3 | 55 | x | x | x | x | x | x | x |
| 23 | - | 2300 | 230 | 115 | 76.7 | 57.5 | x | x | x | x | x | x | x |
| 24 | - | 2400 | 240 | 120 | 80 | 60 | x | x | x | x | x | x | x |
| 25 | - | 2500 | 250 | 125 | 83.3 | 62.5 | x | x | x | x | x | x | x |
| 26 | - | 2600 | 260 | 130 | 86.7 | 65 | x | x | x | x | x | x | x |
| 27 | - | 2700 | 270 | 135 | 90 | 67.5 | x | x | x | x | x | x | x |
| 28 | - | 2800 | 280 | 140 | 93.3 | 70 | x | x | x | x | x | x | x |
| 29 | - | 2900 | 290 | 145 | 96.7 | 72.5 | x | x | x | x | x | x | x |
| 30 | - | 3000 | 300 | 150 | 100 | 75 | x | x | x | x | x | x | x |
| 31 | - | 3100 | 310 | 155 | 103 | 77.5 | x | x | x | x | x | x | x |
| 32 | - | 3200 | 320 | 160 | 107 | 80 | x | x | x | x | x | x | x |
| 33 | - | 3300 | 330 | 165 | 110 | 82.5 | x | x | x | x | x | x | x |
| 34 | - | 3400 | 340 | 170 | 113 | 85 | x | x | x | x | x | x | x |
| 35 | - | 3500 | 350 | 175 | 117 | 87.5 | x | x | x | x | x | x | x |
| 36 | - | 3600 | 360 | 180 | 120 | 90 | x | x | x | x | x | x | x |
| 37 | - | 3700 | 370 | 185 | 123 | 92.5 | x | x | x | x | x | x | x |
| 38 | - | 3800 | 380 | 190 | 127 | 95 | x | x | x | x | x | x | x |
| 39 | - | 3900 | 390 | 195 | 130 | 97.5 | x | x | x | x | x | x | x |
| 40 | - | 4000 | 400 | 200 | 133 | 100 | x | x | x | x | x | x | x |
| > 40 | - | >4000 | >400 | >200 | >134 | >100 | x | x | x | x | x | x | x |

FIG. 4I

| | vascular growth or negative remodeling potential (1=full potential) |||||||||||||
|---|---|---|---|---|---|---|---|---|---|---|---|---|---|
| | radiation rate [mGy/hours] |||||||||||||
| | 0 | below 25 | 25 | 50 | 100 | 200 | 300 | 400 | 500 | 600 | 700 | 800 | 900 | 1000 | over 1000 |
| below 0.1 | 0 | 0.05 | 0.1 | 0.1 | 0.1 | 0.1 | 0.1 | 0.1 | 0.1 | 0.1 | 0.1 | 0.1 | 0.1 | 0.1 | 0.1 |
| 0.1-1 | 0.05 | 0.13 | 0.2 | 0.2 | 0.2 | 0.2 | 0.2 | 0.2 | 0.2 | 0.2 | 0.2 | 0.2 | 0.2 | 0.2 | 0.2 |
| 1 | 0.0875 | 0.175 | 0.25 | 0.25 | 0.25 | 0.25 | 0.25 | 0.25 | 0.25 | 0.25 | 0.25 | 0.25 | 0.25 | 0.25 | 0.25 |
| 2 | 0.1 | 0.2 | 0.4 | 0.4 | 0.4 | 0.4 | 0.4 | 0.4 | 0.4 | 0.4 | 0.4 | 0.4 | 0.4 | 0.4 | 0.4 |
| 3 | 0.125 | 0.25 | 0.5 | 0.5 | 0.5 | 0.5 | 0.5 | 0.5 | 0.5 | 0.5 | 0.5 | 0.5 | 0.5 | 0.5 | 0.5 |
| 4 | 0.15 | 0.3 | 0.6 | 0.6 | 0.6 | 0.6 | 0.6 | 0.6 | 0.6 | 0.6 | 0.6 | 0.6 | 0.6 | 0.6 | 0.6 |
| 5 | 0.175 | 0.35 | 0.7 | 0.7 | 0.7 | 0.7 | 0.7 | 0.7 | 0.7 | 0.7 | 0.7 | 0.7 | 0.7 | 0.7 | 0.7 |
| 6 | 0.2 | 0.4 | 0.8 | 0.8 | 0.8 | 0.8 | 0.8 | 0.8 | 0.8 | 0.8 | 0.8 | 0.8 | 0.8 | 0.8 | 0.8 |
| 7 | 0.225 | 0.45 | 0.9 | 0.9 | 0.9 | 0.9 | 0.9 | 0.9 | 0.9 | 0.9 | 0.9 | 0.9 | 0.9 | 0.9 | 0.9 |
| 8 | 0.25 | 0.75 | 1 | 1 | 1 | 1 | 1 | 1 | 1 | 1 | 1 | 1 | 1 | 1 | 1 |
| 9 | 0.25 | 0.75 | 1 | 1 | 1 | 1 | 1 | 1 | 1 | 1 | 1 | 1 | 1 | 1 | 1 |
| 10 | 0.25 | 0.75 | 1 | 1 | 1 | 1 | 1 | 1 | 1 | 1 | 1 | 1 | 1 | 1 | 1 |
| 11 | 0.25 | 0.75 | 1 | 1 | 1 | 1 | 1 | 1 | 1 | 1 | 1 | 1 | 1 | 1 | 1 |
| 12 | 0.25 | 0.75 | 1 | 1 | 1 | 1 | 1 | 1 | 1 | 1 | 1 | 1 | 1 | 1 | 1 |
| 13 | 0.25 | 0.75 | 1 | 1 | 1 | 0.9 | 0.5 | 0.5 | 0.5 | 0.5 | 0.5 | 0.5 | 0.5 | 0.5 | 0.5 |
| 14 | 0.25 | 0.75 | 1 | 1 | 1 | 0.8 | 0.5 | 0 | 0 | 0 | 0 | 0 | 0 | 0 | 0 |
| 15 | 0.25 | 0.75 | 1 | 1 | 1 | 0.8 | 0.5 | 0 | 0 | 0 | 0 | 0 | 0 | 0 | 0 |
| 16 | 0.25 | 0.75 | 1 | 1 | 1 | 0.8 | 0.5 | 0 | 0 | 0 | 0 | 0 | 0 | 0 | 0 |
| 17 | 0.25 | 0.75 | 1 | 1 | 1 | 0.8 | 0.5 | 0 | 0 | 0 | 0 | 0 | 0 | 0 | 0 |
| 18 | 0.25 | 0.75 | 1 | 1 | 1 | 0.8 | 0.5 | 0 | 0 | 0 | 0 | 0 | 0 | 0 | 0 |
| 19 | 0.25 | 0.75 | 1 | 1 | 1 | 0.8 | 0.5 | 0 | 0 | 0 | 0 | 0 | 0 | 0 | 0 |
| 20 | 0.25 | 0.75 | 1 | 1 | 1 | 0.8 | 0.5 | 0 | 0 | 0 | 0 | 0 | 0 | 0 | 0 |
| 21 | 0.25 | 0.75 | 1 | 1 | 1 | 0.8 | 0.5 | 0 | 0 | 0 | 0 | 0 | 0 | 0 | 0 |
| 22 | 0.25 | 0.75 | 1 | 1 | 1 | 0.8 | 0.5 | 0 | 0 | 0 | 0 | 0 | 0 | 0 | 0 |
| 23 | 0.25 | 0.75 | 1 | 1 | 1 | 0.8 | 0.5 | 0 | 0 | 0 | 0 | 0 | 0 | 0 | 0 |
| 24 | 0.25 | 0.75 | 1 | 1 | 1 | 0.8 | 0.5 | 0 | 0 | 0 | 0 | 0 | 0 | 0 | 0 |
| 25 | 0.25 | 0.75 | 1 | 1 | 1 | 0.8 | 0.5 | 0 | 0 | 0 | 0 | 0 | 0 | 0 | 0 |
| 26 | 0.25 | 0.75 | 1 | 1 | 1 | 0.8 | 0.5 | 0 | 0 | 0 | 0 | 0 | 0 | 0 | 0 |
| 27 | 0.25 | 0.75 | 1 | 1 | 1 | 0.8 | 0.5 | 0 | 0 | 0 | 0 | 0 | 0 | 0 | 0 |
| 28 | 0.25 | 0.75 | 1 | 1 | 1 | 0.8 | 0.5 | 0 | 0 | 0 | 0 | 0 | 0 | 0 | 0 |
| 29 | 0.25 | 0.75 | 1 | 1 | 1 | 0.8 | 0.5 | 0 | 0 | 0 | 0 | 0 | 0 | 0 | 0 |
| 30 | 0.25 | 0.75 | 1 | 1 | 1 | 0.8 | 0.5 | 0 | 0 | 0 | 0 | 0 | 0 | 0 | 0 |
| 31 | 0.25 | 0.75 | 1 | 1 | 1 | 0.8 | 0.5 | 0 | 0 | 0 | 0 | 0 | 0 | 0 | 0 |
| 32 | 0.25 | 0.75 | 1 | 1 | 1 | 0.8 | 0.5 | 0 | 0 | 0 | 0 | 0 | 0 | 0 | 0 |
| 33 | 0.25 | 0.75 | 1 | 1 | 1 | 0.8 | 0.5 | 0 | 0 | 0 | 0 | 0 | 0 | 0 | 0 |
| 34 | 0.25 | 0.75 | 1 | 1 | 1 | 0.8 | 0.5 | 0 | 0 | 0 | 0 | 0 | 0 | 0 | 0 |
| 35 | 0.25 | 0.75 | 1 | 1 | 1 | 0.8 | 0.5 | 0 | 0 | 0 | 0 | 0 | 0 | 0 | 0 |
| 36 | 0.2375 | 0.7125 | 0.95 | 0.95 | 0.95 | 0.76 | 0.475 | 0 | 0 | 0 | 0 | 0 | 0 | 0 | 0 |
| 37 | 0.225 | 0.675 | 0.9 | 0.9 | 0.9 | 0.72 | 0.45 | 0 | 0 | 0 | 0 | 0 | 0 | 0 | 0 |
| 38 | 0.2125 | 0.6375 | 0.85 | 0.85 | 0.85 | 0.68 | 0.425 | 0 | 0 | 0 | 0 | 0 | 0 | 0 | 0 |
| 39 | 0.2 | 0.6 | 0.8 | 0.8 | 0.8 | 0.64 | 0.4 | 0 | 0 | 0 | 0 | 0 | 0 | 0 | 0 |
| 40 | 0.1875 | 0.5625 | 0.75 | 0.75 | 0.75 | 0.6 | 0.375 | 0 | 0 | 0 | 0 | 0 | 0 | 0 | 0 |
| 40-60 | 0.175 | 0.525 | 0.7 | 0.7 | 0.7 | 0.56 | 0.35 | 0 | 0 | 0 | 0 | 0 | 0 | 0 | 0 |
| 60-80 | 0.15 | 0.45 | 0.6 | 0.6 | 0.6 | 0.48 | 0.3 | 0 | 0 | 0 | 0 | 0 | 0 | 0 | 0 |
| 80-120 | 0.0875 | 0.2625 | 0.35 | 0.35 | 0.35 | 0.28 | 0.175 | 0 | 0 | 0 | 0 | 0 | 0 | 0 | 0 |
| over 120 | 0 | 0 | 0 | 0 | 0 | 0 | 0 | 0 | 0 | 0 | 0 | 0 | 0 | 0 | 0 |

(row labels column = total radiation [Gy])

FIG. 4J

METHODS AND DEVICES FOR TREATING VASCULAR RELATED DISORDERS

RELATED APPLICATIONS

This application is a National Phase of PCT Patent Application No. PCT/IB2017/057989 having International filing date of Dec. 15, 2017, which claims the benefit of priority under 35 USC § 119(e) of U.S. Provisional Patent Application Nos. 62/434,629 filed on Dec. 15, 2016 and 62/481,500 filed on Apr. 4, 2017. The contents of the above applications are all incorporated by reference as if fully set forth herein in their entirety.

FIELD AND BACKGROUND OF THE INVENTION

The present invention, in some embodiments thereof, relates methods and devices for radiative treatment of tissue and, more particularly, but not exclusively, to methods and devices for radiative treatment of blood vessels.

Brachytherapy is a form of radiotherapy, where, generally, a radiative source (isotope) is encapsulated and manually placed within or at the vicinity of an anatomical area to be treated.

Brachytherapy is commonly used oncologically and generally involves treatment of cervix, prostate, breast, skin cancers.

The encapsulated source emits x-ray, gamma, beta, or alpha radiation at prescribed doses and thereby inflicting radiation related injuries[11] at tumors and shrinking or obliterating the tumor.

The biological controlling mechanism is thought to be direct damage to the tissue, which causes scarring and fibrotic tissue formation at the injury sites.

These biological mechanisms are similar to those activated in the AVM treatment state of the art Stereotactic Surgery (Radioactive surgery for AVM's), where a focal beam locally ablates a blood vessel's tissue and causes injury and blockage by fibrotic tissue.

The doses in Brachytherapy can be roughly divided into two segments: chronic radiation[11,12] (superscript numbers direct in this document to numbered reference in the section entitled "Field And Background Of The Invention") and acute radiation,[12] brachytherapy methods. The first method includes seed placement at the desired area, where slow release of radiation from the seed to the surrounding tissue, produces the desired outcome over weeks/months. The latter method includes temporary seed placement at the desired area, where the entire dose of the desired radiation amount is released within minutes to hours after which the seed is extracted.

It is important to note that, in both treatment strategies, the desired biological effect is injury and scarring of the tissue. Where chronic radiation relies on continuous injury and fibrosis cycle that will, eventually, kill the tumor and acute radiation relies on concentrated damage and focused trauma to the tumor structure.

Background Art Includes:

1. Nishida N. Angiogenesis in cancer. 2006; 2(3):213-219.

2. Kleibeuker E A, Griffioen A W, Verheul H M, Slotman B J, Thijssen V L. combining angiogenesis inhibition and radiotherapy: A double-edged sword. *Drug Resist. Updat.* 2012; 1S(3):173-182. doi:10.1016/j.drup.2012.04.002.

3. Greene A K. Vascular Anomalies: Current Overview of the Field. 2011; (Lm). doi:10.1016/j.cps.0.2010.08.004.

4. Weiss R, James W D, Lessnau K-D, Izguirre D, Lanza J. Venous Insufficiency. *Medscape* 201S:1-14. Available at: www(dot)emedicine(dot)medscape(dot)com/article/108S412-overview.

5. Maleti O, Perrin M. Reconstructive surgery for deep vein reflux in the lower limbs: Techniques, results and indications. *Eur. J. Vasc. Endovasc. Surg.* 2011; 41(6):837-848. doi:10.1016/j.ejvs.2011.02.013.

6. Goel R R aj, Abidia A, Hardy S C. Surgery for deep venous incompetence. *Cochrane database Syst. Rev.* 2015; 2(2):CD001097. doi:10.1002/146S18S8.CD001097.pub3.

7. Mayo Clinic. Valvular Heart Disease Overview. Available at: www(dot)mayoclinic(dot)org/diseases-conditions/heart-valve-disease/symptoms-causes/dxc-2030S6S8.

8. Kim E J, Vermeulen S, Li F J, Newell D W. A review of cerebral arteriovenous malformations and treatment with stereotactic radiosurgery. *Transl. Cancer Res.* 2014; 3(4): 399-410. doi:10.3978/j.issn.2218-676X.2014.07.07.

9. L. Da Costa, M. C. Wallace, K. G. T. Brugge, C. O'Kelly, R. A. Willinsky and MT. "The natural history and predictive features of hemorrhage from brain arteriovenous malformations," 2009.

10. Souvik Sen, MD, MPH, MS F. Arteriovenous Malformations Treatment & Management.

11. Koukourakis G, Kelekis N, Armonis V, Kouloulias V. Brachytherapy for Prostate Cancer: A Systematic Review. 2009; 2009. doi:10.11SS/2009/32794S.

12. Rivard M J, Ph D, Melhus C. Brachytherapy Dose Calculation Formalism, Dataset Evaluation, and Treatment Planning System Implementation. *System* 2009; (June).

13. Kim E J, Vermeulen S, Li F J, Newell D W. A review of cerebral arteriovenous malformations and treatment with stereotactic radiosurgery. *Transl. Cancer Res.* 2014; 3(4): 399-410. doi:10.3978/j.issn.2218-676X.2014.07.07.

14. Lunsford, D. L.; Kondziolka, D.; Niranjan, A.; Lindquist, C.; Loeffler, J.; McDermott, M.; Sisti, M.; Flickinger, J. C.; Maltz, A.; Horowitz, M.; Ledbetter, T. K.; Emerick R L. Stereotactic Radiosurgery for Patients with Intracranial Arteriovenous Malformations (AVM). *Report* 2009; (March): 1-22.

15. van Der Giessen W J, Regar E, Harteveld M S, et al. "Edge Effect" of (32)p radioactive stents is caused by the combination of chronic stent injury and radioactive dose falloff. *Circulation* 2001;104(18):2236-41. Available at: www(dot)ncbi(dot)nlm(dot)nih(dot)gov/cgi-bin/Entrez/referer? www(dot)circulationaha(dot)org/cgi/content/full/104/18/2236.

16. Kim H S, Waksman R, Cottin Y, et al. Edge stenosis and geographical miss following intracoronary gamma radiation therapy for in-stent restenosis. *J. Am. Coll. Cardiol.* 2001; 37(4):1026-1030. doi:10.1016/50735-1097(01)01112-3.

17. Hansen A, Hehrlein C, Hardt S, et al. Is the "candy-wrapper" effect of 32P radioactive β-emitting stents due to remodeling or neointimal hyperplasia: Insights from intravascular ultrasound. *Catheter. Cardiovasc. /nterv.* 2001; 54(1):41-48. doi:10.1002/ccd.123S.

18. Do Y S, Yakes W F, Shin S W, et al. Ethanol embolization of arteriovenous malformations: interim results. *Radiology* 200S; 23 S (2): 674-682. doi:10.1148/radiol.23S2040449.

21. Wiedermann G. Dose Response for the of Restenosis in Swine. *Physics (College. Park. Md)*. 1996; 3016 (June).

22. van Der Giessen W J, Regar E, Harteveld M S, et al. "Edge Effect" of (32)p radioactive stents is caused by the combination of chronic stent injury and radioactive dose falloff. Circulation 2001;104(18):2236-41. Available at:

23. Liang X, So Y H, Cui J, et al. The low-dose ionizing radiation stimulates cell proliferation via activation of the MAPK/ERK pathway in rat cultured mesenchymal stem cells. *J. Radiat. Res.* 2011; 52(3):380-6. doi:10.1269/jrr.10121.

24. Kim C S, Kim J-M, Nam S Y, et al. Low-dose of Ionizing Radiation Enhances Cell Proliferation Via Transient ERK1/2 and p38 Activation in Normal Human Lung Fibroblasts. *J. Radiat. Res.* 2007; 48(5):407-415. doi: 10.1269/jrr.07032.

25. Hansen A, Hehrlein C, Hardt S, et al. Is the "candy-wrapper" effect of 32P radioactive-emitting stents due to remodeling or neointimal hyperplasia: Insights from intravascular ultrasound. *Catheter. Cardiovasc. Interv.* 2001; 54(1):41-48. doi:10.1002/ccd.1235.

26. Wardeh A J, Kay I P, Sabate M, et al. Beta-Particle-emitting radioactive stent implantation. A safety and feasibility study. *Circulation* 1999; 100(16):1684-1689. Available at: http://www(dot)ncbi(dot)nlm(dot)nih(dot)gov/cgi-bin/Entrez/referer? http://www(dot)circulationaha(dot)org/cgi/content/full/100/16/1684.

27. Albiero R, Adamian M, Kobayashi N, et al. Clinical Investigation and Reports Short- and Intermediate-Term Results of 32 P Radioactive ß-Emitting Stent Implantation in Patients With. 2000:18-27.

28. Kim H S, Waksman R, Cottin Y, et al. Edge stenosis and geographical miss following intracoronary gamma radiation therapy for in-stent restenosis. *J. Am. Coll. Cardiol.* 2001; 37(4): 1026-1030. doi: 10.1016/S0735-1097(01) 01112-3.

31. Van Der Giessen W J, Regar E, Harteveld M S, et al. "Edge Effect" of (32)p radioactive stents is caused by the combination of chronic stent injury and radioactive dose falloff. *Circulation* 2001; 104(18):2236-41. Available at:
www(dot)ncbi(dot)nlm(dot)nih(dot)gov/cgi-bin/Entrez/referer?
www(dot)circulationaha(dot)org/cgi/content/full/104/18/2236.

32. Costa M A, Kozuma K, Kay I P, et al. Geographic Miss. 2000: 2467-2472.

33. JUDAH WEINBERGER, M.D., PH.D., * HOWARD AMOLS, PH.D.," RONALD D. ENNIS, M.D.,' ALLAN SCHWARTZ, M.D.,* JOSEPH G. WIEDERMANN, M.D.* AND CHARLES MARBOE M D. INTRACORONARY IRRADIATION: DOSE RESPONSE FOR THE PREVENTION OF RESTENOSIS IN SWINE. 1996.

34. Albiero R, Adamian M, Kobayashi N, et al. Clinical Investigation and Reports Short- and Intermediate-Term Results of 32 P Radioactive-Emitting Stent Implantation in Patients With. 2000:18-27.

Albiero R, Nishida T, Adamian M, et al. Edge restenosis after implantation of high activity (32)P radioactive beta-emitting stents. Circulation 2000; 101(21):2454-2457. Available at: www(dot)ncbi(dot)nlm(dot)nih(dot)gov/pubmed/10831516.

SUMMARY OF THE INVENTION

Following are examples of some embodiments of the invention. Features of one example may be combined with features of one or more other examples, unless expressly prohibited and form additional examples of some embodiments of the invention.

Example 1

Use of low level ionizing radiation for the gradual constriction of one or more blood vessel of one or more blood vessel.

Example 2

The use of low level ionizing radiation according to Example 1 wherein radioactive material provides said low level ionizing radiation.

Example 3

The use of low level ionizing radiation according to any one of Examples 1-2, wherein said constriction is to an extent that closes said one or more blood vessel.

Example 4

The use of low level ionizing radiation according to any one of Examples 1-3, wherein said low level ionizing radiation is selected to promote said constriction by hyperproliferation of cells of said one or more blood vessel.

Example 5

The use of low level ionizing radiation according to Example 4, wherein said hyperproliferation includes hyperproliferation of smooth muscle cells of said one or more blood vessel.

Example 6

The use of low level ionizing radiation according to any one of Examples 1-5, wherein said low level ionizing radiation is selected to promote said gradual constriction by negative remodeling of said one or more blood vessel.

Example 7

The use of low level ionizing radiation according to any one of Examples 1-6, wherein said gradual constriction is over a time period of 1 day to 6 months.

Example 8

The use of low level ionizing radiation according to any one of Examples 1-7, wherein said gradual constriction is over a time period of 1 week to 3 months.

Example 9

The use of low level ionizing radiation according to any one of Examples 1-8, wherein said low level ionizing radiation is one or more of: a dose of 1-40 Gy at a rate of 25-400 mGy/hour; a dose of 1-13 Gy at a rate of 500-1000 mGy/hour.

Example 10

The use of low level ionizing radiation according to any one of Examples 1-9, wherein said low level ionizing radiation is one or more of a dose of 8-35 Gy at a rate of 50-200 mGy/hour; a dose of 8-12 Gy at a rate of 50-1000 mGy/hour.

Example 11

The use of low level ionizing radiation according to any one of Examples 1-10, wherein said low level ionizing radiation includes acute irradiation.

Example 12

The use of low level ionizing radiation according to Example 11, wherein said acute irradiation includes a total dose of: 0.1-13 Gy at a rate of over 500 mGy/hour; or 0.1-13 Gy at a rate of 500-1500 mGy/hour.

Example 13

The use of low level ionizing radiation according to any one of Examples 1-12, wherein said radiation includes chronic irradiation.

Example 14

The use of low level ionizing radiation according to Example 13, wherein said chronic irradiation includes a total dose of 0.1-80 Gy to a rate of 5 m-500 mGy/hour.

Example 15

The use of low level ionizing radiation according to any one of Examples 1-14, wherein said gradual constriction is for the treatment of one or more of: tumor feeding blood vessels; angiogenesis; vascular anomaly; vascular malformation (AVM); hemangioma; chronic venous insufficiency (CVI); valve malfunction; deep vein thrombosis; varicocele; aneurysm.

Example 16

The use of low level ionizing radiation according to Example 15, wherein said tumor feeding blood vessels are one or more of tumor feeding blood vessels via vasculogenesis, tumor feeding blood vessels via angiogenesis.

Example 17

The use of low level ionizing radiation according to Example 15, wherein said hemangioma is one or more of ophthalmic hemangioma, hepatic hemangioma, cardiac hemangioma.

Example 18

The use of low level ionizing radiation according to Example 15, wherein said valve malfunction includes one or more of regurgitation and insufficiency.

Example 19

The use of low level ionizing radiation according to Example 15 or Example 18 wherein said valve malfunction is of one or more venous valve or a heart valve.

Example 20

The use of low level ionizing radiation according to any one of Examples 1-19, wherein said radiation is supplied by one or more seed comprising encapsulated radioactive material.

Example 21

The use of low level ionizing radiation according to any one of Examples 1-20, wherein said radiation is at a level which does not cause above 10% cellular death rate in target tissue.

Example 22

A method of treatment comprising:
selecting tissue to be exposed to radiation for gradual closure of one or more blood vessel within said tissue to be exposed radiation;
selecting radiation levels to promote gradual constriction of said one or more vessel;
exposing said tissue to be exposed radiation to selected radiation levels.

Example 23

The method according to Example 22, wherein said constriction is to an extent that promotes closure of said one or more vessel.

Example 24

The method according to any one of Examples 22-23, wherein said selecting comprises selecting said radiation levels to promote said constriction by hyperproliferation of cells of said one or more blood vessel.

Example 25

The method according to any one of Examples 22-24, wherein said selecting comprises selecting said radiation levels to promote said gradual closure by negative remodeling of said one or more blood vessel.

Example 26

The method according to any one of Examples 22-25 wherein said selecting radiation levels comprises planning a spatial distribution of one or more sources to provide radiation within a therapeutic window over a geometry of said selected tissue.

Example 27

The method according to any one of Examples 22-26, wherein said gradual closure is over a time period of 1 week to 3 months.

Example 28

The method according to any one of Examples 22-27, wherein said selecting comprises selecting radiation level including one or more of: a dose of 1-40 Gy at a rate of 25-400 mGy/hour; a dose of 1-13 Gy at a rate of 500-1000 mGy/hour.

Example 29

The method according to any one of Examples 22-28, wherein said selecting comprises selecting radiation level including one or more of a dose of 8-35 Gy at a rate of 50-200 mGy/hour; a dose of 8-12 Gy at a rate of 50-1000 mGy/hour.

Example 30

The method according to any one of Examples 22-29, wherein said selecting comprises selecting acute irradiation of total dose of: 0.1-13 Gy at a rate of over 500 mGy/hour; or 0.1-13 Gy at a rate of 500-1500 mGy/hour.

Example 31

The method according to any one of Examples 22-30, wherein said selecting comprises selecting chronic irradiation of a total dose of 0.1-40 Gy at a rate of 25 m-500 mGy/hour.

Example 32

The method according to any one of Examples 22-31, wherein said gradual closure is for the treatment of one or more of: tumor feeding blood vessels; angiogenesis; vascular anomaly; vascular malformation (AVM); hemangioma; chronic venous insufficiency (CVI); valve malfunction; deep vein thrombosis; varicocele; aneurysm.

Example 33

The method according to any one of Examples 22-32, wherein said radiation is supplied by one or more seed comprising encapsulated radioactive material.

Example 34

The method according to any one of Examples 22-33, comprising injuring said tissue to be exposed radiation.

Example 35

The method according to any one of Examples 22-34, comprising:
selecting tissue to be injured; and
injuring said tissue to be injured, where said tissue to be exposed to radiation has a different extent to said tissue to be exposed to radiation.

Example 36

The method according to any one of Examples 34-35, wherein said injuring comprises one or more of injuring via: application of one or more sclerosing agent;
mechanical injury; temperature change; irradiation.

Example 37

The method according to any one of Examples 22-36, wherein said exposing comprises positioning at least one source comprising radioactive material in proximity to said tissue to be exposed to radiation.

Example 38

The method according to Example 37, wherein said at least one source comprises a seed comprising encapsulated radioactive material.

Example 39

The method according to any one of Examples 35-38, comprising anchoring said at least one source to tissue.

Example 40

The method according to Example 39, wherein said anchoring comprises expanding a structure coupled to said at least one source within a vessel to be treated or a vessel proximal to tissue to be treated.

Example 41

The method according to any one of Examples 39-40, wherein one or more of said positioning and said anchoring is by endovascular catheter delivery.

Example 42

The method according to any one of Examples 37-41, wherein said at least one source includes a plurality of sources.

Example 43

The method according to Example 42, wherein said plurality of sources are coupled to a single expandable structure.

Example 44

The method according to Example 42, wherein said plurality of sources are coupled to more than one expandable structure.

Example 45

The method according to any one of Examples 22-44, wherein said selecting of said radiation levels comprises selecting one or more of selecting a volume of extent of said radiation levels suitable for said selected tissue.

Example 46

The method according to any one of Examples 22-43, wherein said exposing comprises positioning a plurality of sources in a topography selected to expose said tissue to said radiation levels.

Example 47

The method according to any one of Examples 40-46, wherein one or more of:
said structure exerts an outwards force on 0.1-20% of a portion of an inner wall circumference of said vessel in which said structure is located; and
said structure provides support to said vessel in which it is located for 1-5% of a length of the device long axis.

Example 48

A device comprising:
at least one element configured to anchor said device to a lumen;
at least one radiation source coupled to said element, where said source is configured to emit radiation levels suitable to cause gradual closure of said lumen at a distance of less than 30 mm from said source.

Example 49

The device according to Example 48, wherein said at least one radiation source comprises 0.01-20 mCi.

Example 50

The device according to Example 49, wherein said at least one radiation source comprises 1-15 µCi.

Example 51

The device according to any one of Examples 48-50, wherein said at least one radiation source is part of said element or is said element.

Example 52

The device according to any one of Examples 48-51, wherein said at least one radiation source is a seed comprising encapsulated radioactive material.

Example 53

The device according to Example 52, wherein said seed has an elongate shape.

Example 54

The device according to any one of Examples 48-53, wherein said at least one element is an expandable element.

Example 55

The device according to Example 54, wherein said expandable element is elastically expandable.

Example 56

The device according to any one of Examples 54-55, wherein said expandable element is plastically expandable.

Example 57

The device according to any one of Examples 48-56, wherein said at least one element comprises at least one loop connected to and extending from said source.

Example 58

The device according to any one of Examples 48-56, wherein said at least one element shaped to anchor said device at axially separated locations along a lumen allowing at least 3 mm between these locations for luminal collapse on the element.

Example 59

The device according to Example 58, wherein said at least one loop is elastically bendable with respect to said source.

Example 60

The device according to any one of Examples 48-59 wherein said device includes at least one hook.

Example 61

The device according to any one of Examples 48-60, wherein said radiation source emits one or more of alpha, beta and gamma radiation.

Example 62

The device according to any one of Examples 48-61, wherein said radiation source comprises one or more of; 13SIodine gamma radiating isotope, 192Irridium gamma emitting isotope and 32Phosphorus beta emitting isotope.

Example 63

The device according to any one of Examples 48-62, wherein said radiation source comprises one or more of; 198gold, 125iodine, 137cesium, 55ocobalt, 55cobalt, 56cobalt, 57cobalt, 57magnesium, 55iron, 32phosphorus, 90strontium, 81rubidium, 2O6bismuth, 67gallium, 77bromine, 129cesium, 73selenium, 72selenium, 72arsenic, 1O3palladium, 2O3lead, 111ilindium, 52iron, 167thulium, 57nickel, 62Zinc, 63copper, 201thallium and 123iodine.

Example 64

The device according to any one of Examples 48-63, wherein a tubular shape of minimum diameter containing said device contacts said device is less than 20% of a surface area of said tubular shape

Example 65

The device according to any one of Examples 48-64, wherein a maximum cross sectional area of said device is 10% of a cross sectional area of a minimum diameter tubular shape containing said device.

Example 66

An expandable device comprising:
at least one expandable element configured to anchor said device to a lumen; and
at least one radioactive source coupled to said expandable element;
wherein a tubular shapes containing said device contacts said device over less than 20% of an outside surface area of said tubular shape.

Example 67

The expandable device according to Example 66, wherein said tubular shapes containing said device are when said device is expanded configurations.

Example 68

An expandable device comprising:
at least one expandable element configured to anchor said device to a lumen; and
at least one radioactive source coupled to said expandable element;
where said source is positioned to irradiate at most 20% of a device long axis length with radiation levels according to any one of Examples 1-22.

Example 65

An expandable device comprising:
at least one expandable element configured to anchor said device to a lumen;
at least one radioactive source coupled to said expandable element;
wherein a maximum cross sectional area of said device is 10% of a cross sectional area of a tubular shape containing said device.

Example 66

The expandable device according to Example 65, wherein said tubular shapes containing said device are when said device is expanded configurations.

Example 67

An expandable device comprising:
at least one expandable element configured to anchor said device to a lumen;
at least one radioactive source coupled to said expandable element;
wherein said device provides support to a lumen in which it is located for at most 5% of a length of the device long axis.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as collecting dental measurements, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. In some cases elements in corresponding figures have corresponding numbers (e.g. element 218 in FIG. 2A corresponds to element 1118 in FIG. 11), which are not necessarily explicitly described.

Figure 2A:
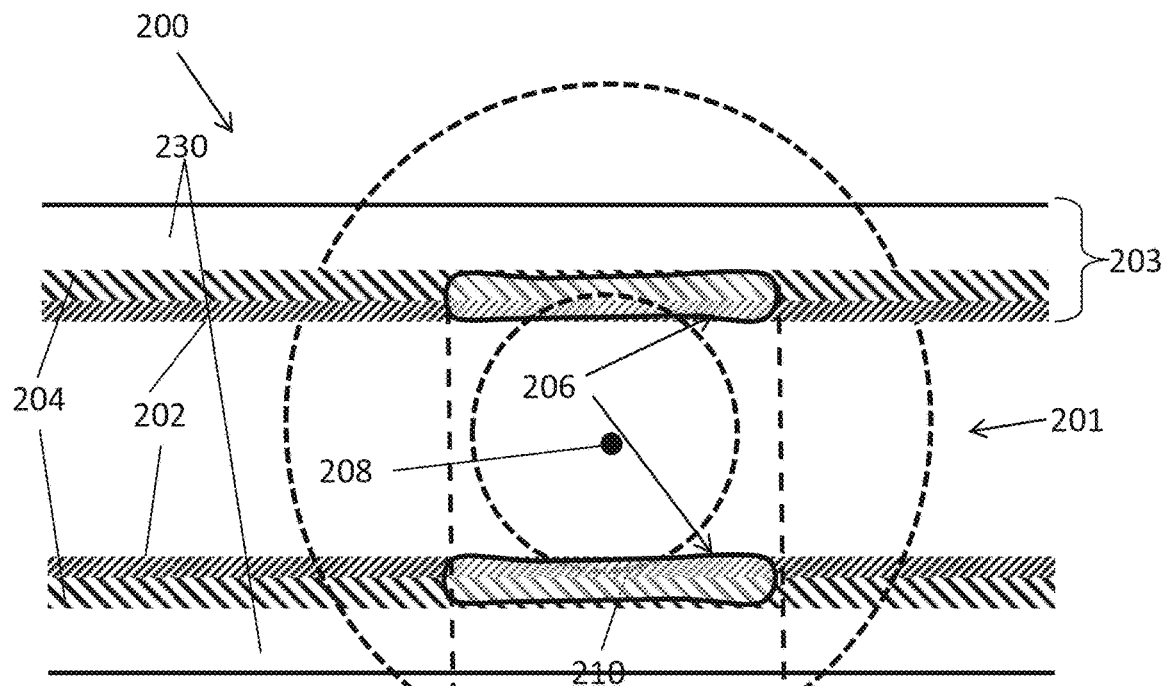
Figure 2B:
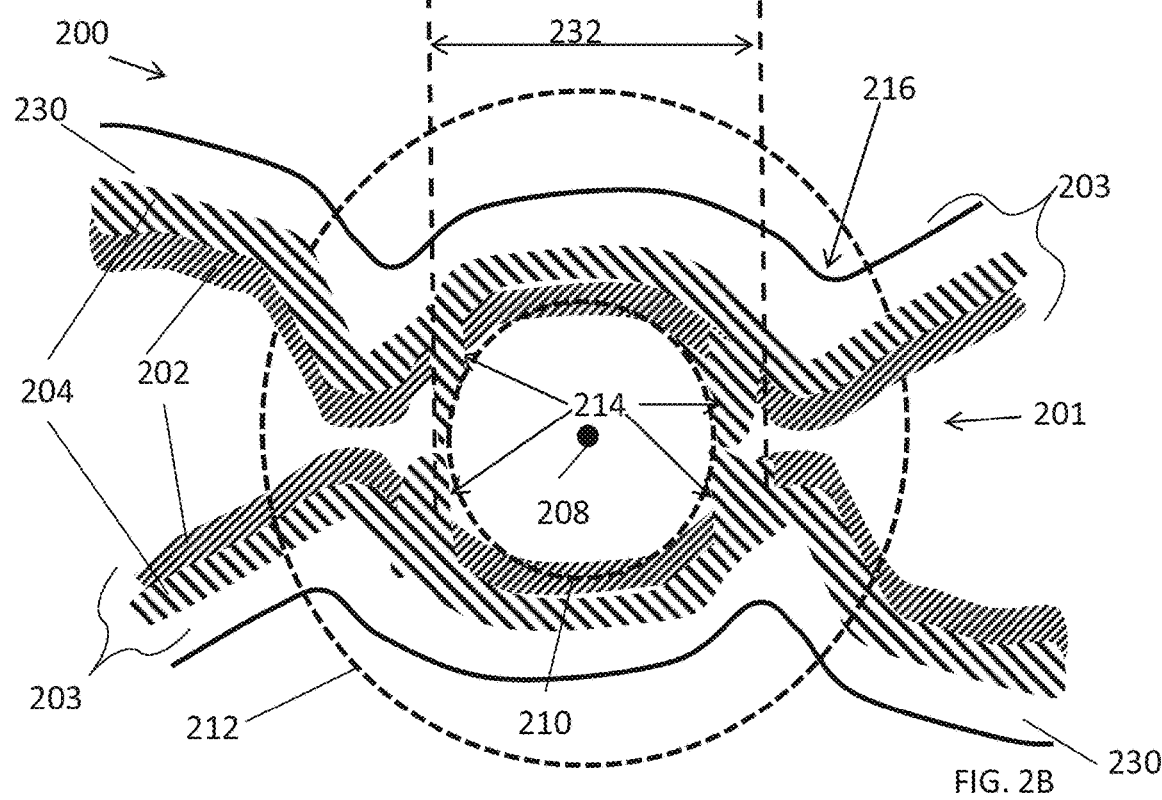
Figure 3:
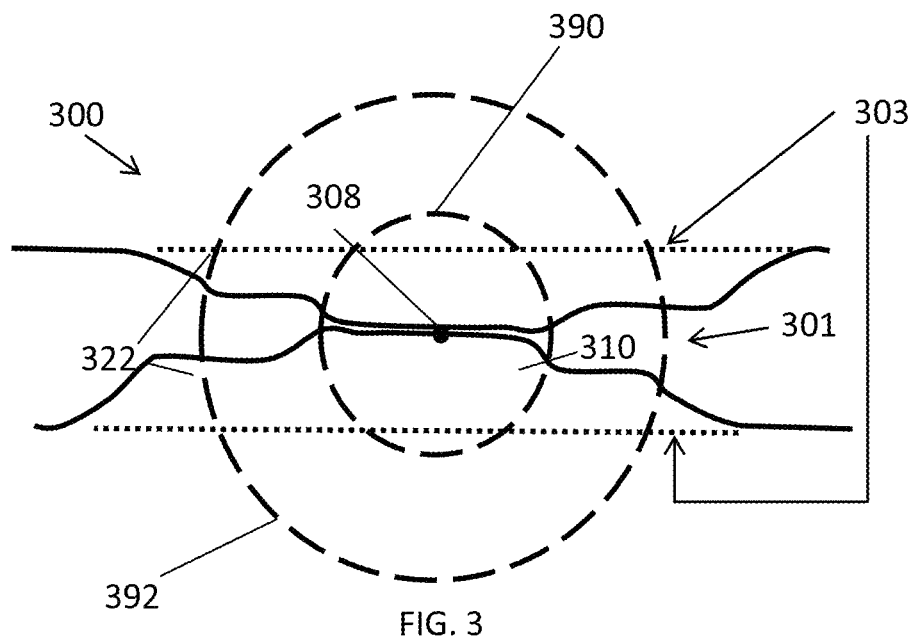
Figure 4A:
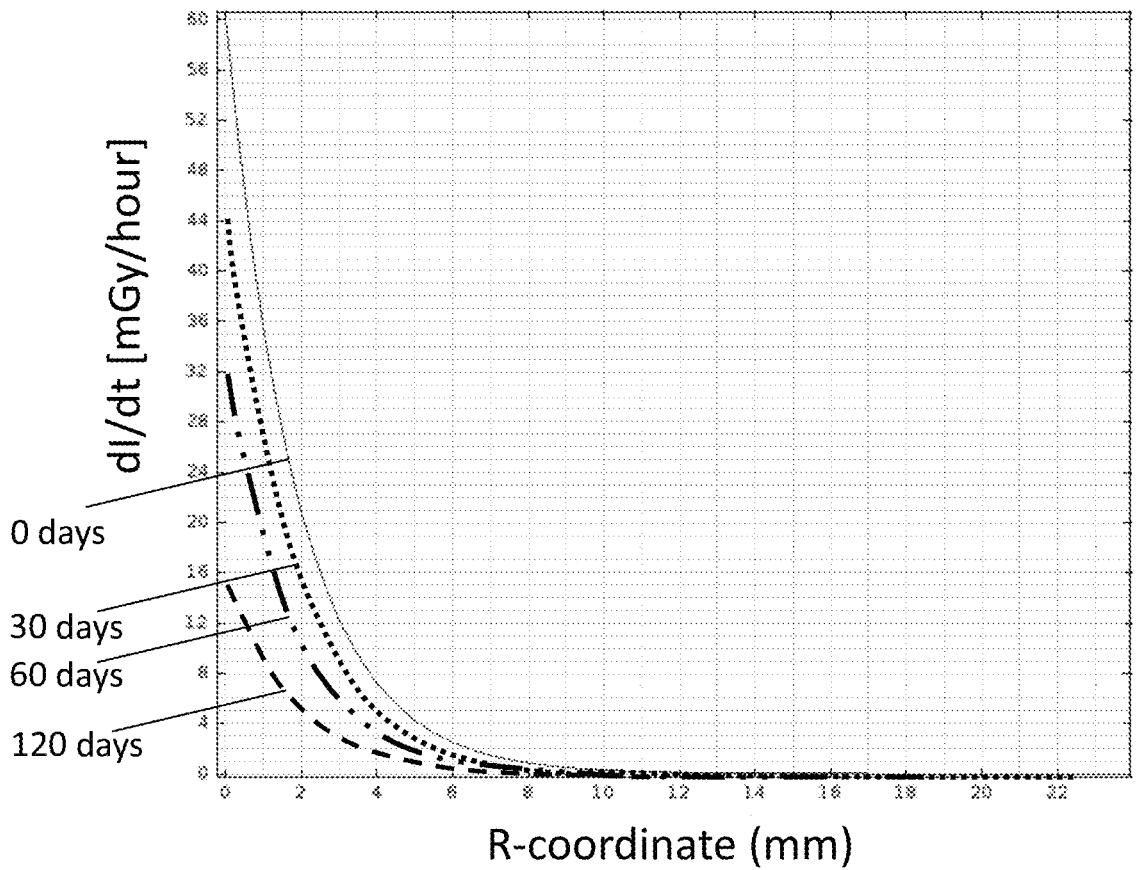
Figure 4B:
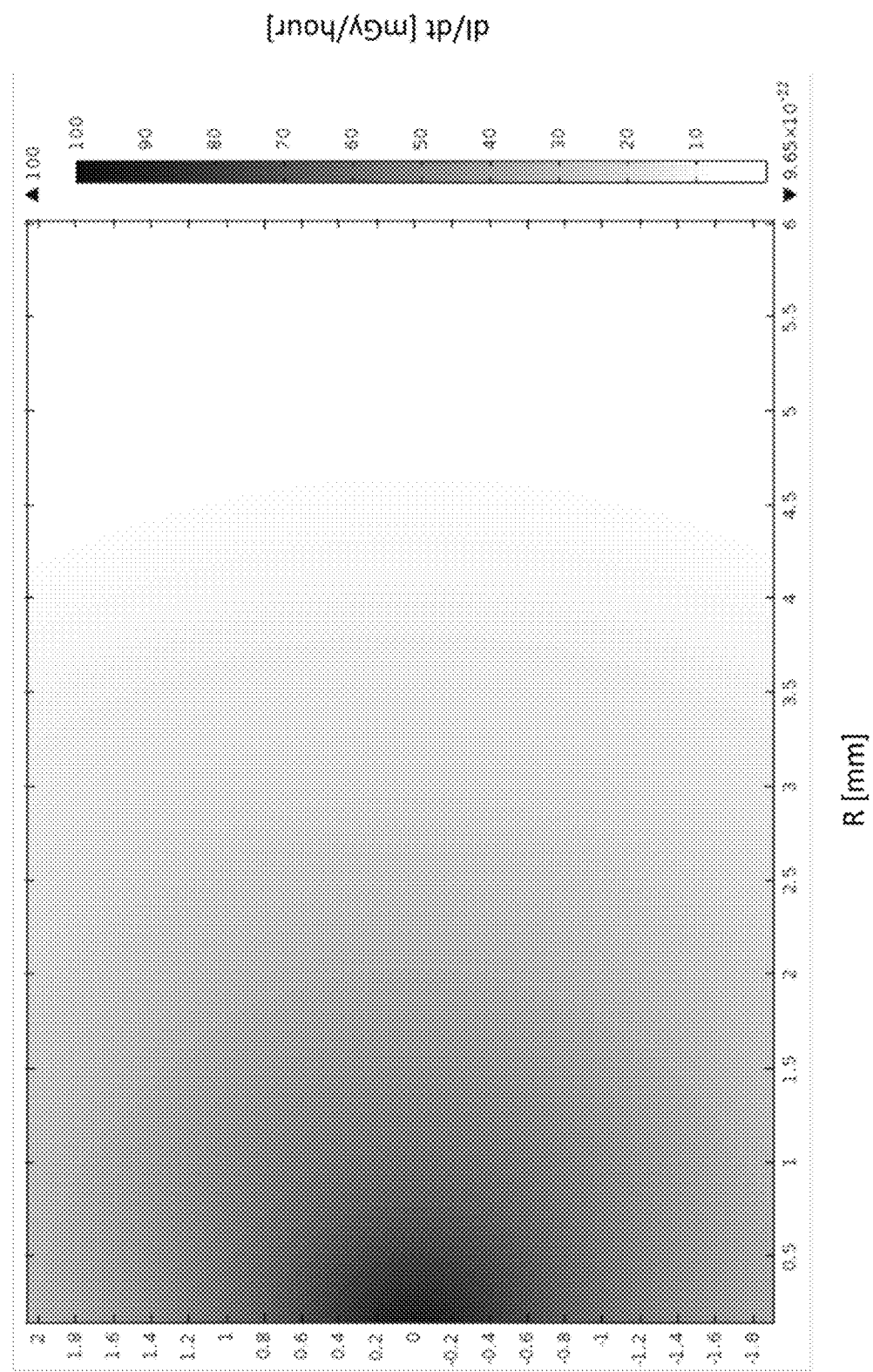
Figure 4C:
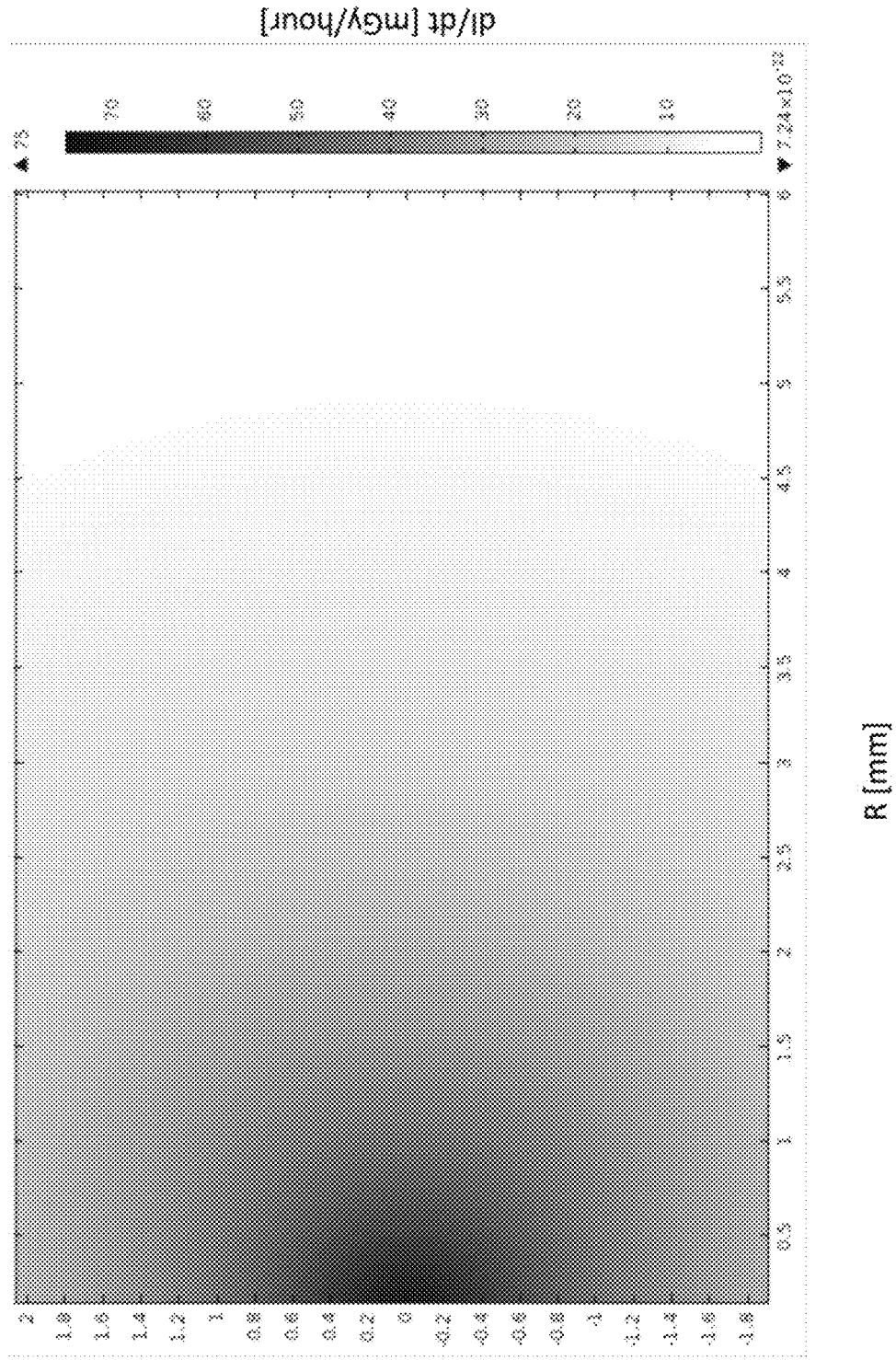
Figure 4D:
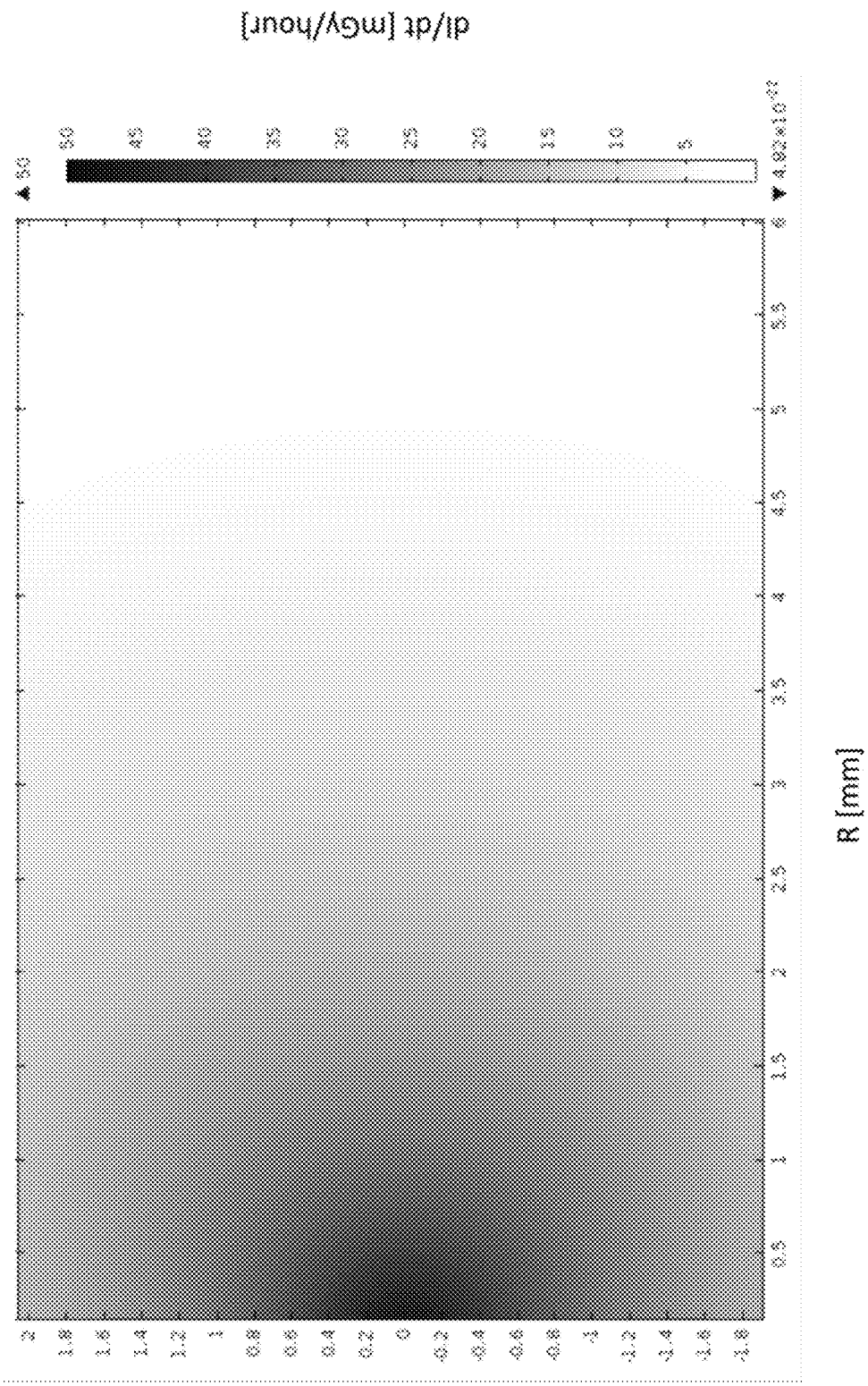
Figure 4E:
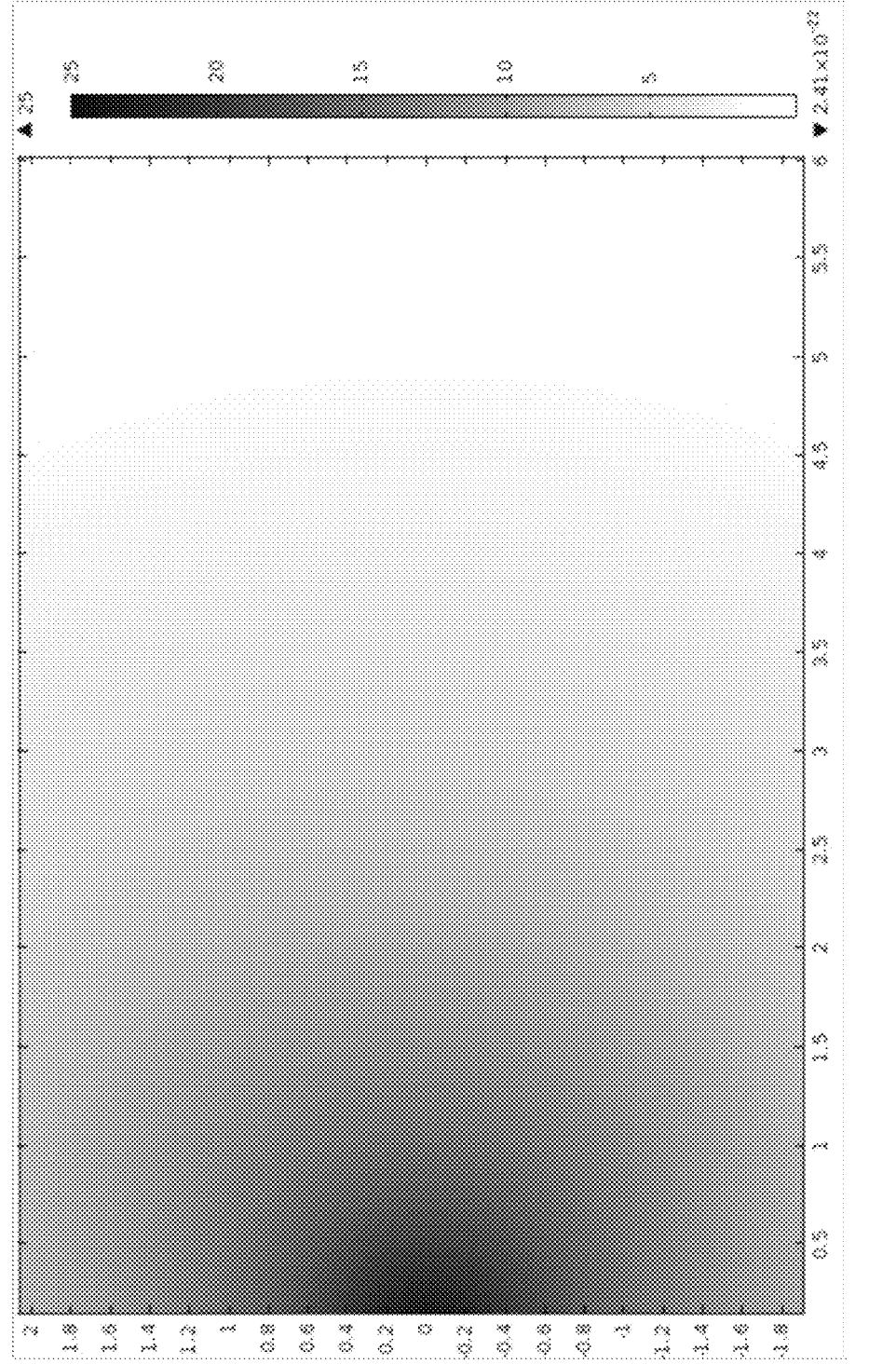
Figure 4F:
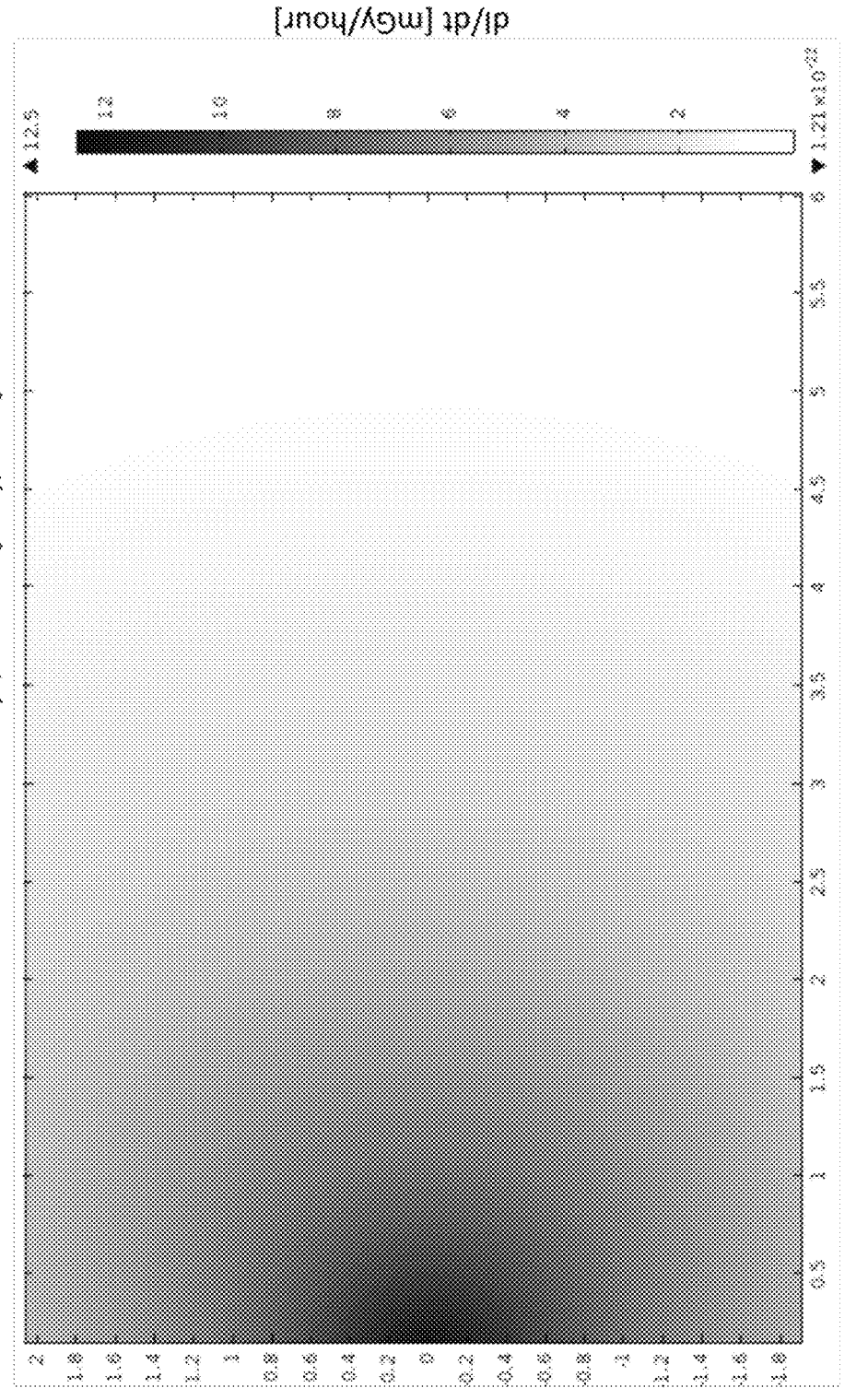
Figure 4G:
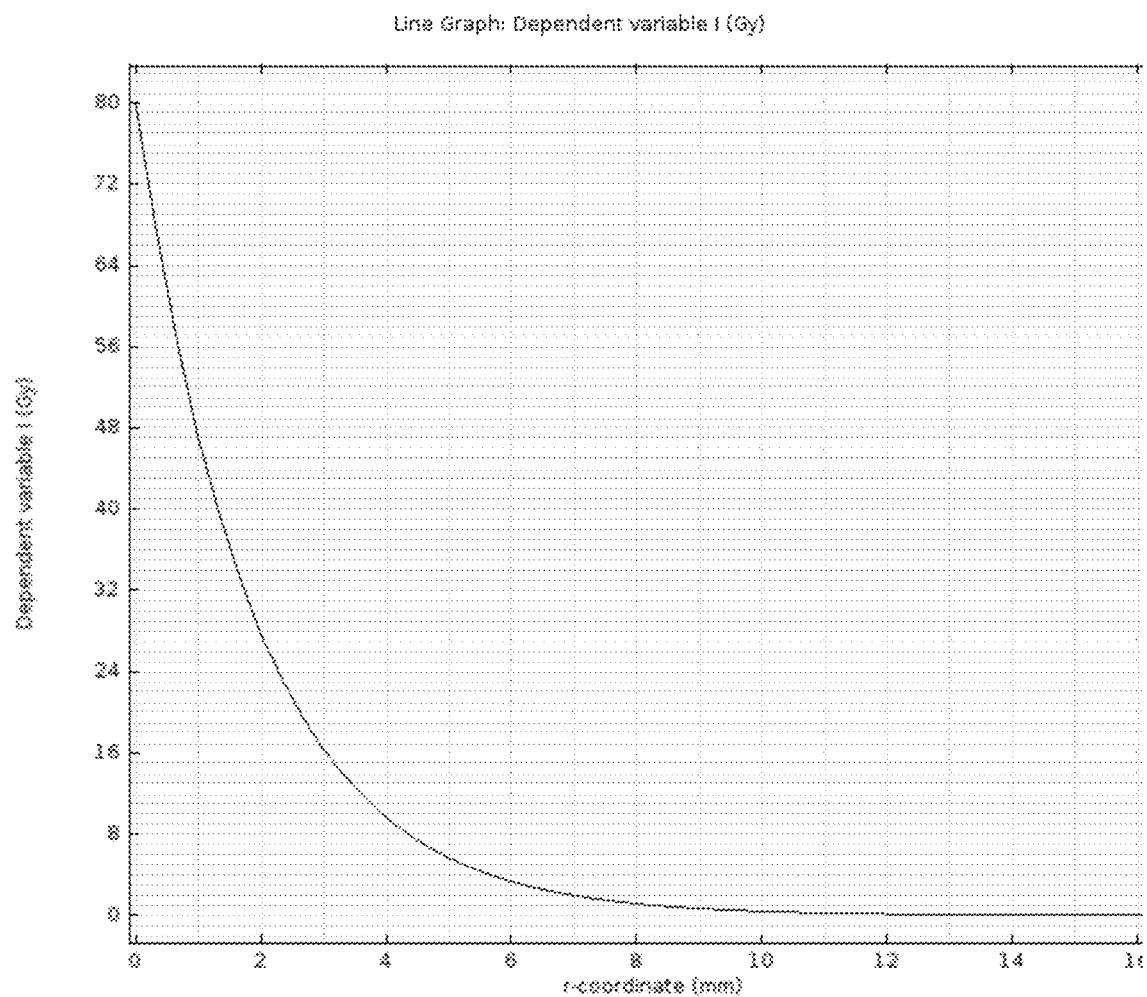
Figure 4H:
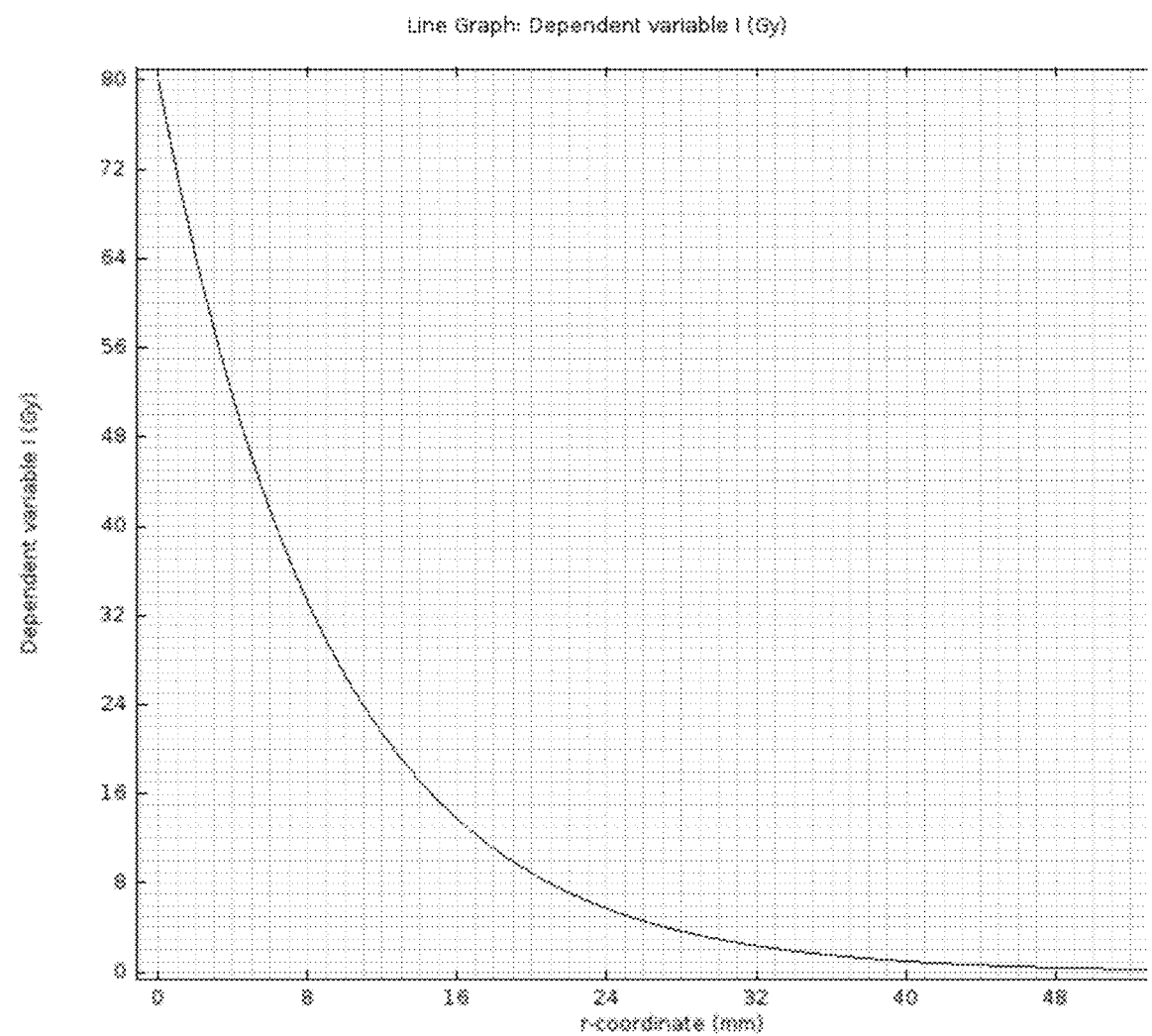
Figure 4K:
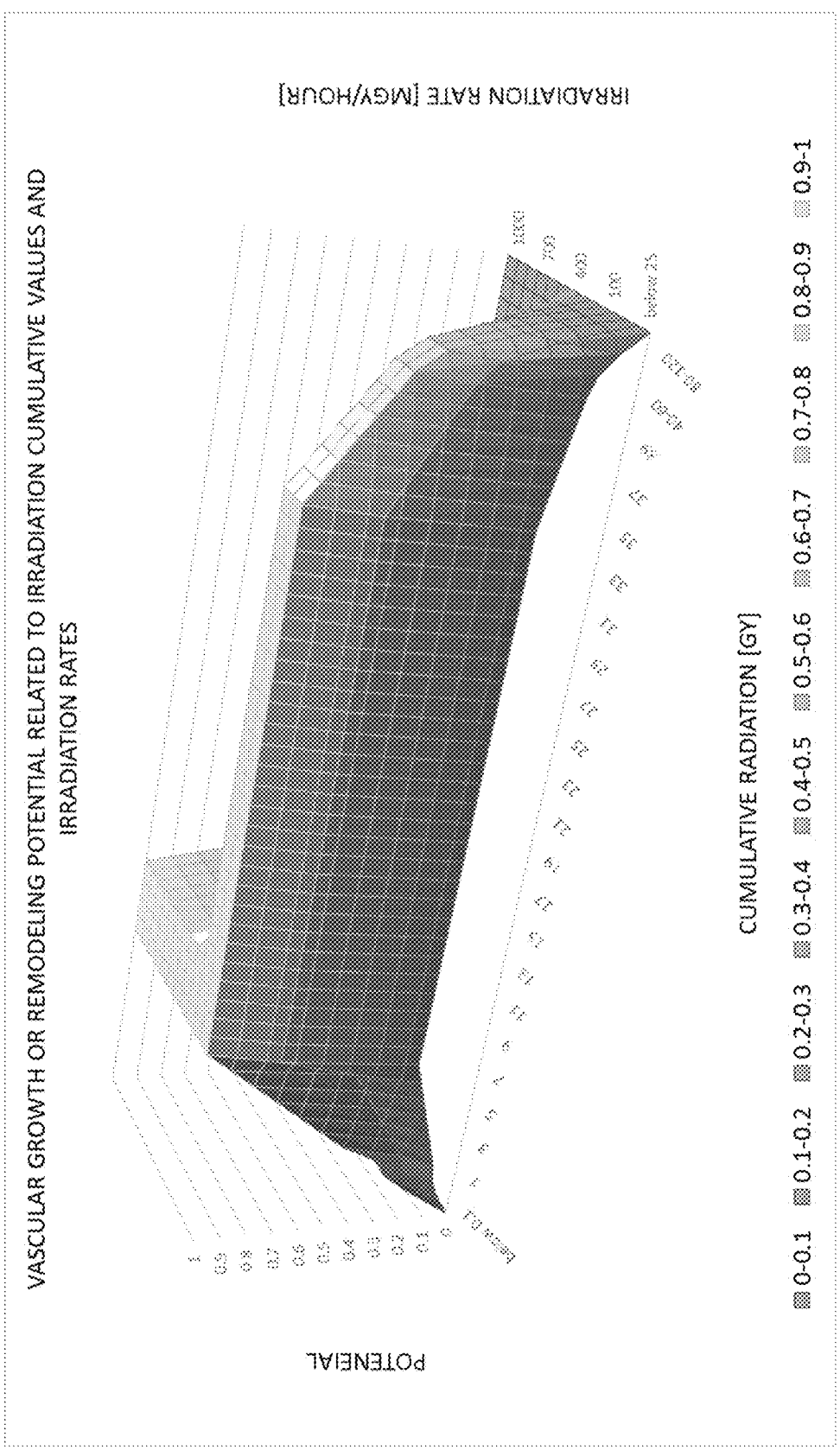
Figure 5A:
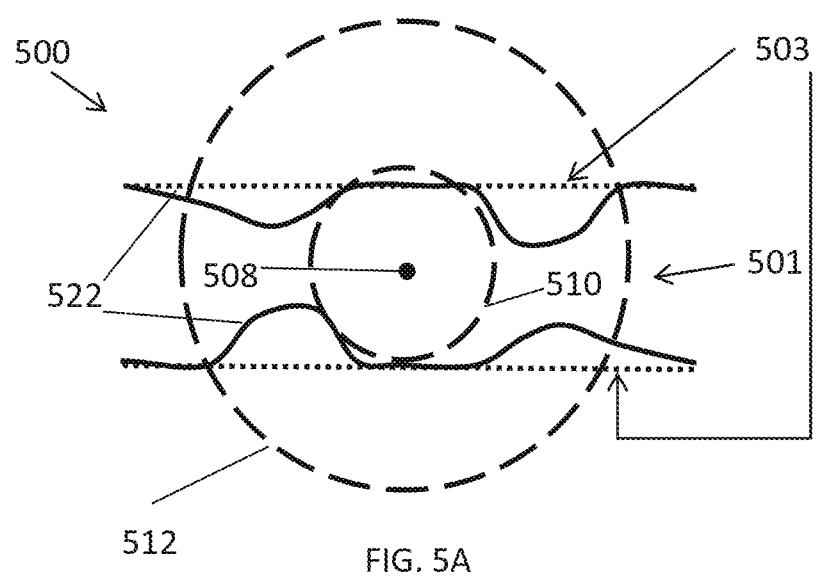
Figure 5B:
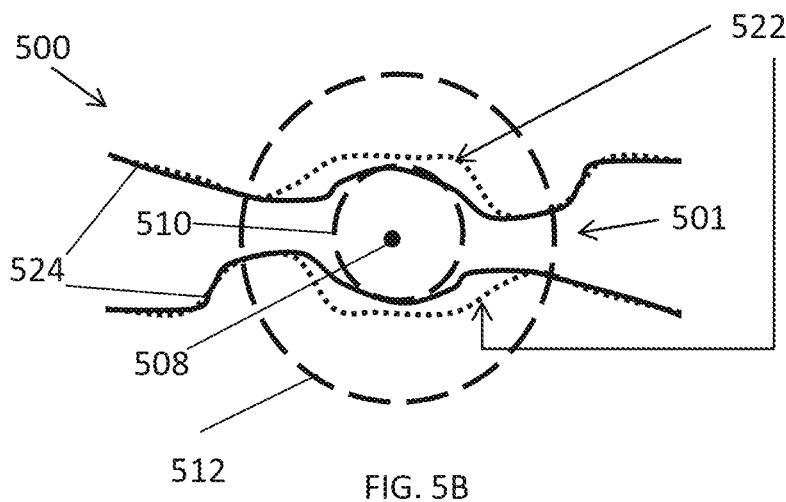
Figure 5C:
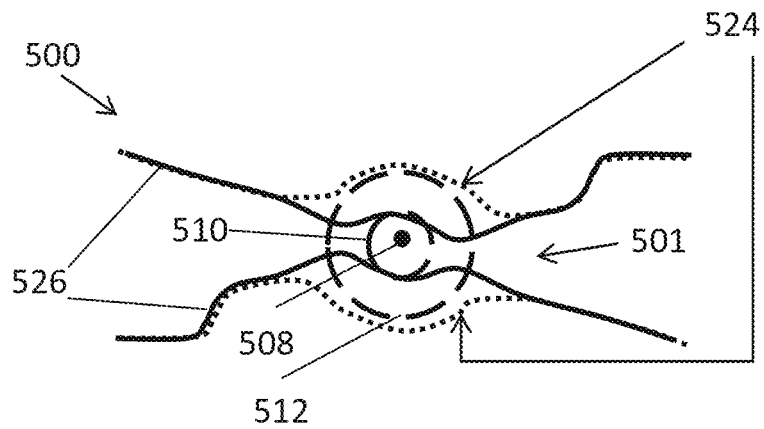
Figure 6A:
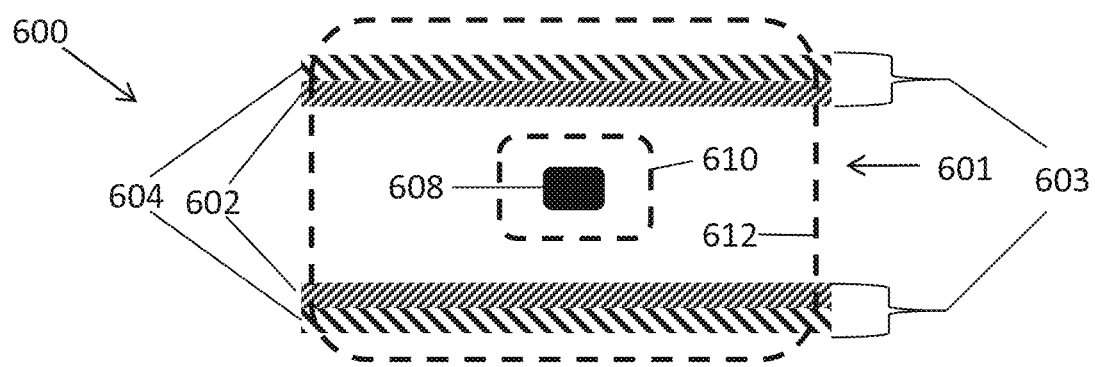
Figure 6B:
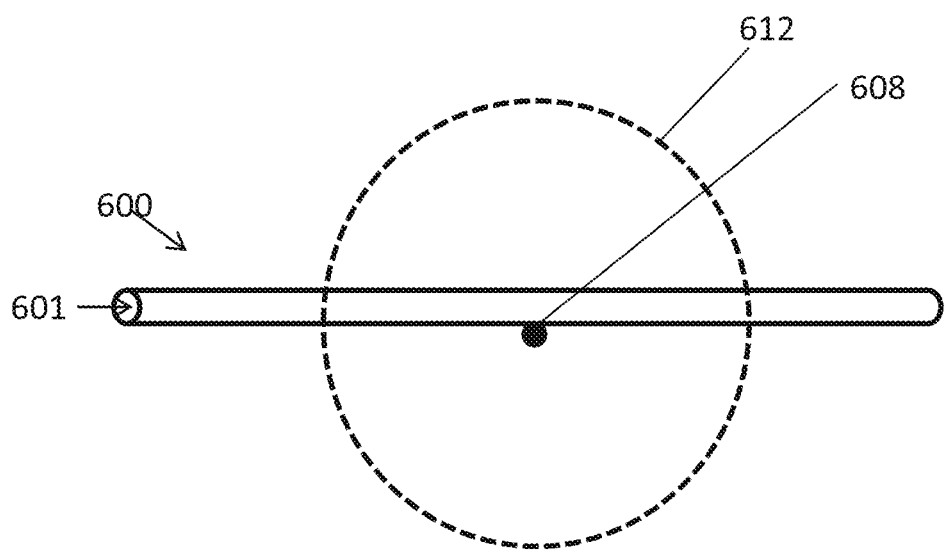
Figure 6C:
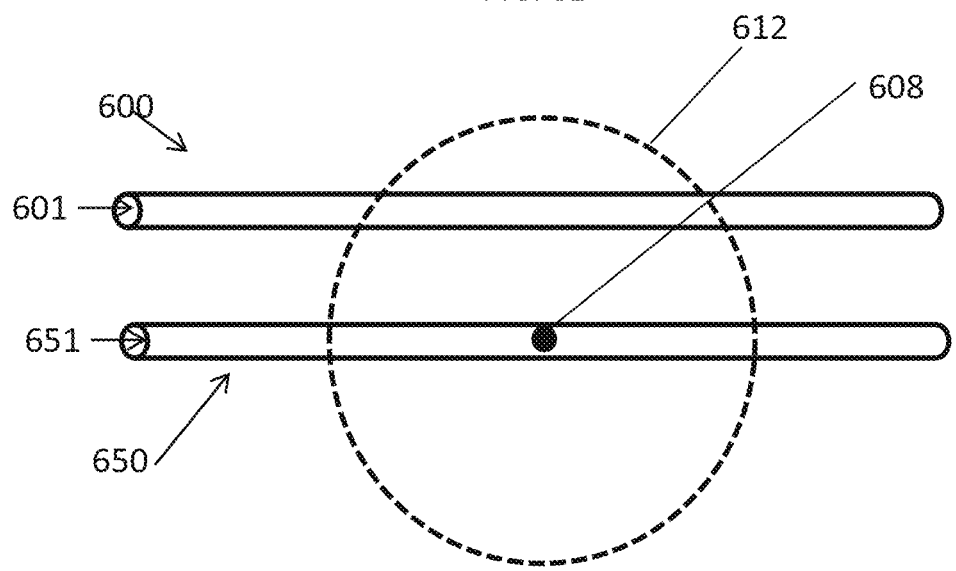
Figure 7:
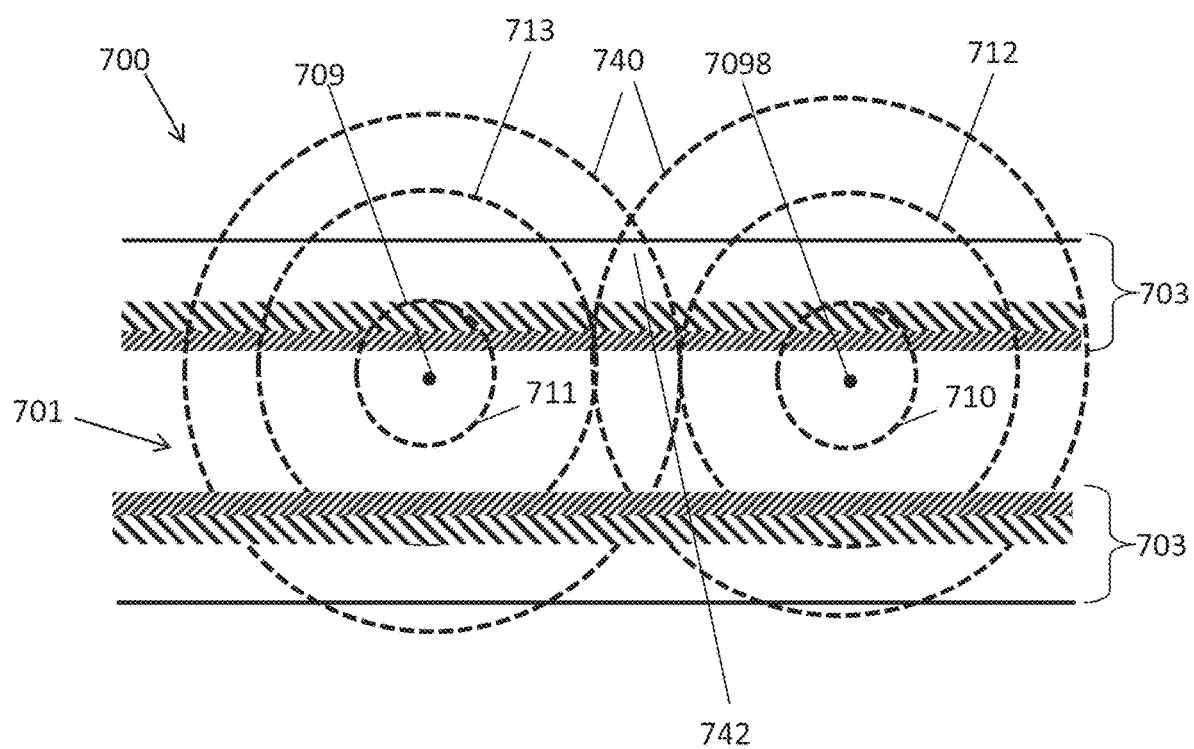
Figure 8A:
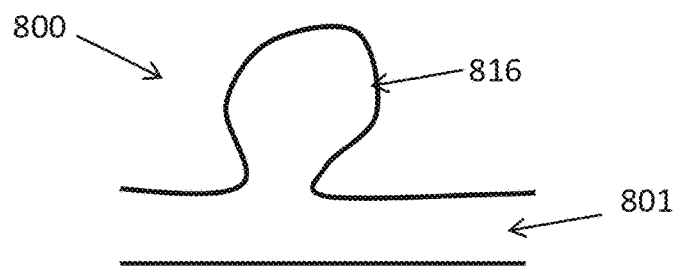
Figure 8B:
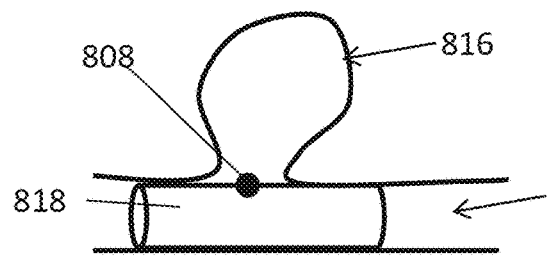
Figure 10:
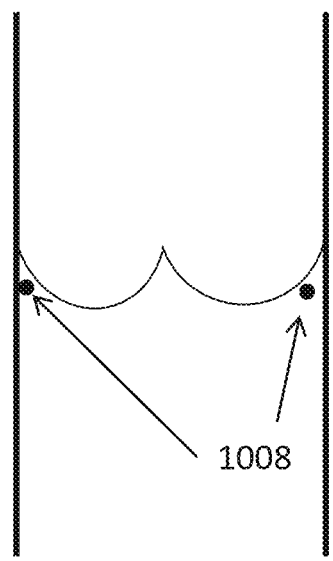
Figure 11:
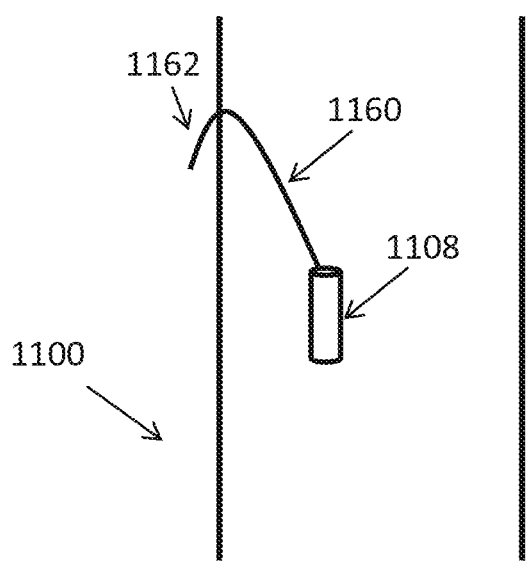
Figure 12:
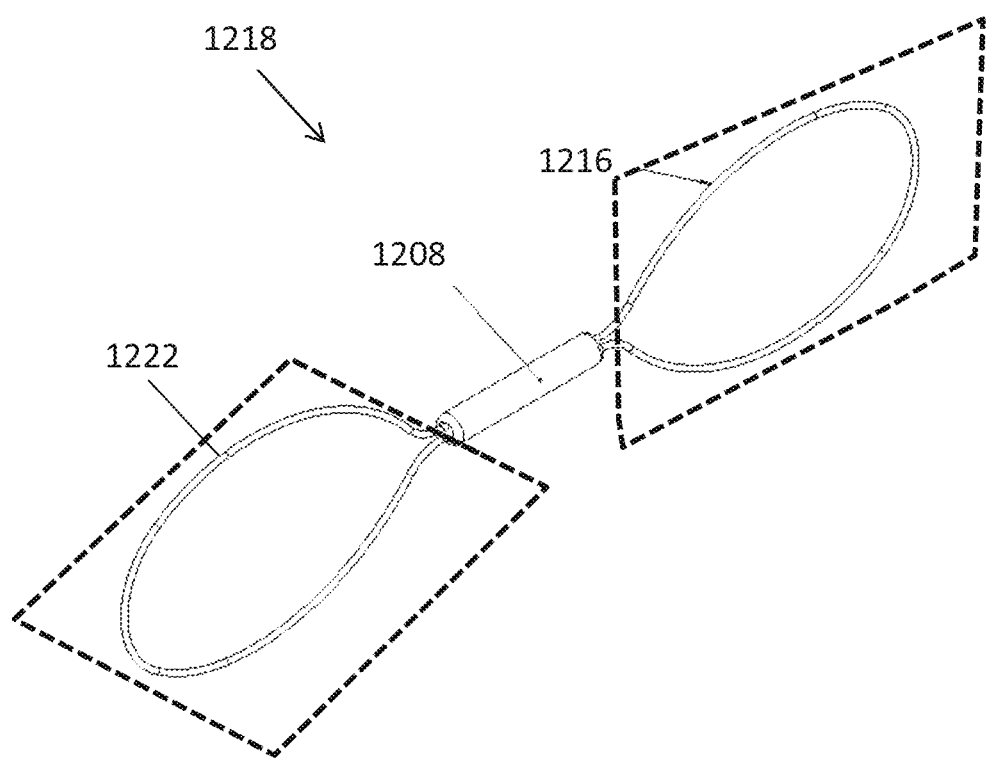
Figure 13:
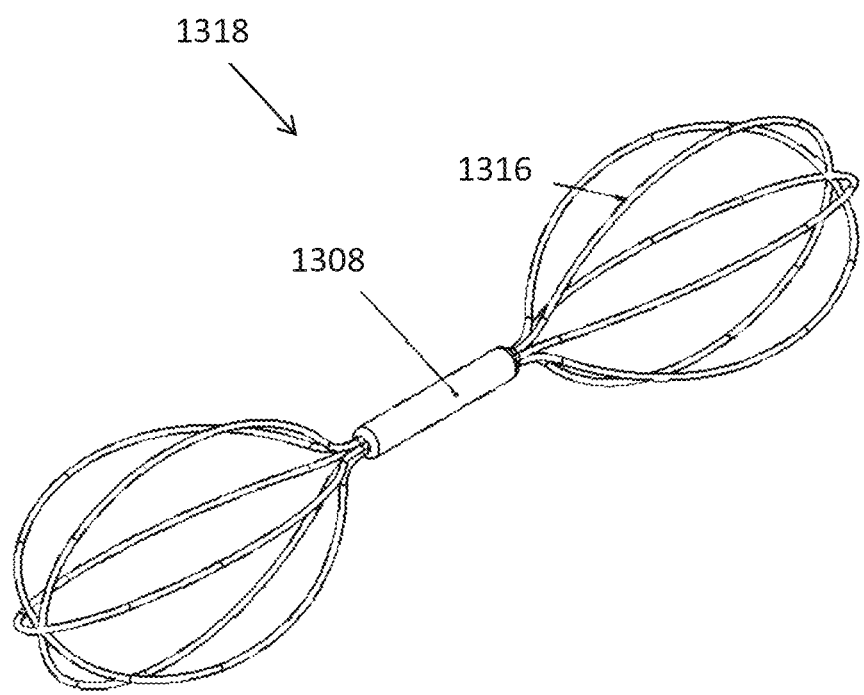
Figure 14A:
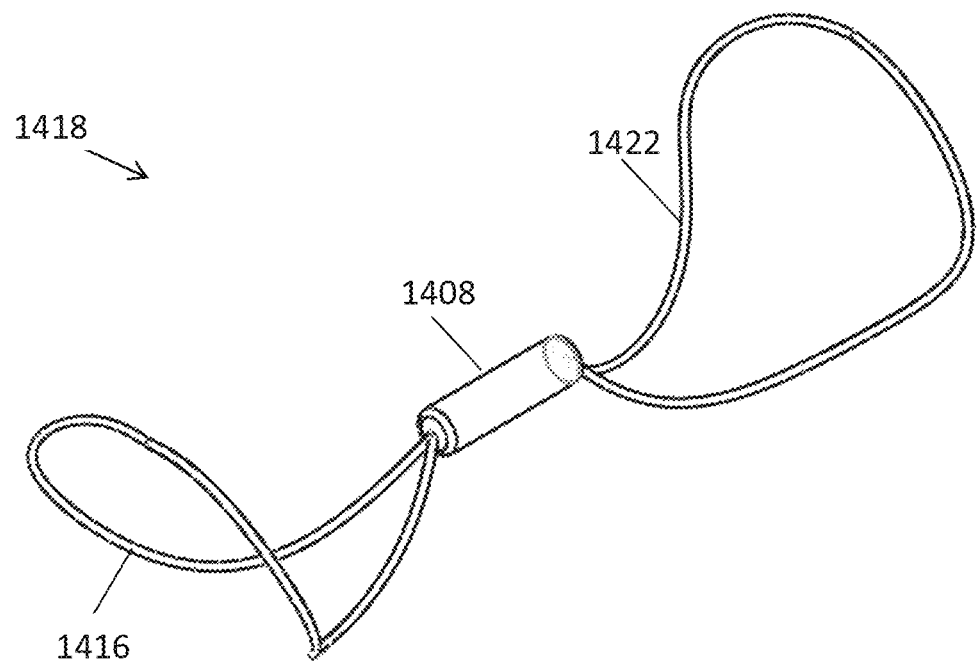
Figure 14B:
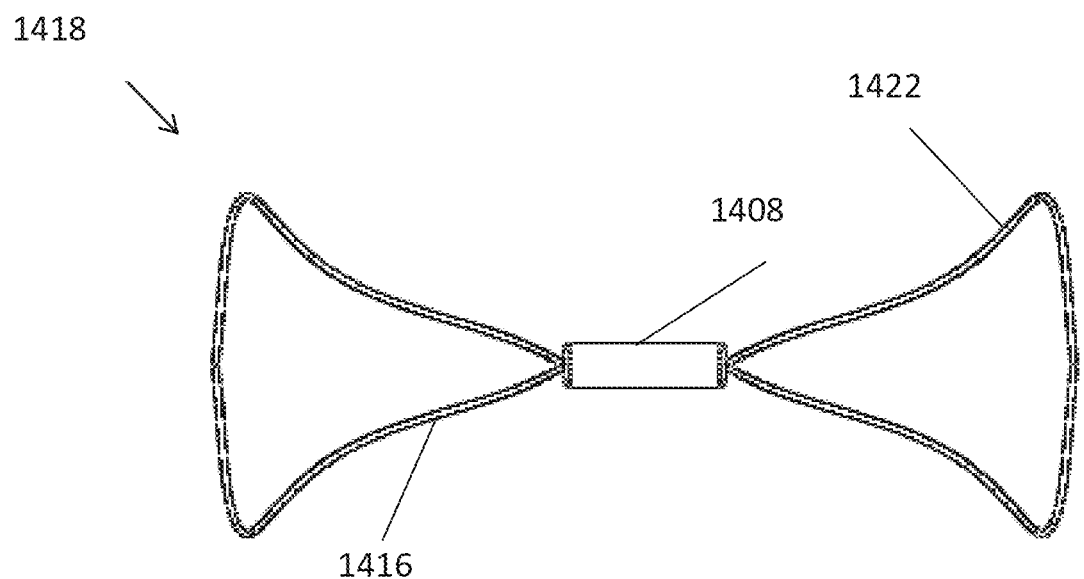
Figure 14C:
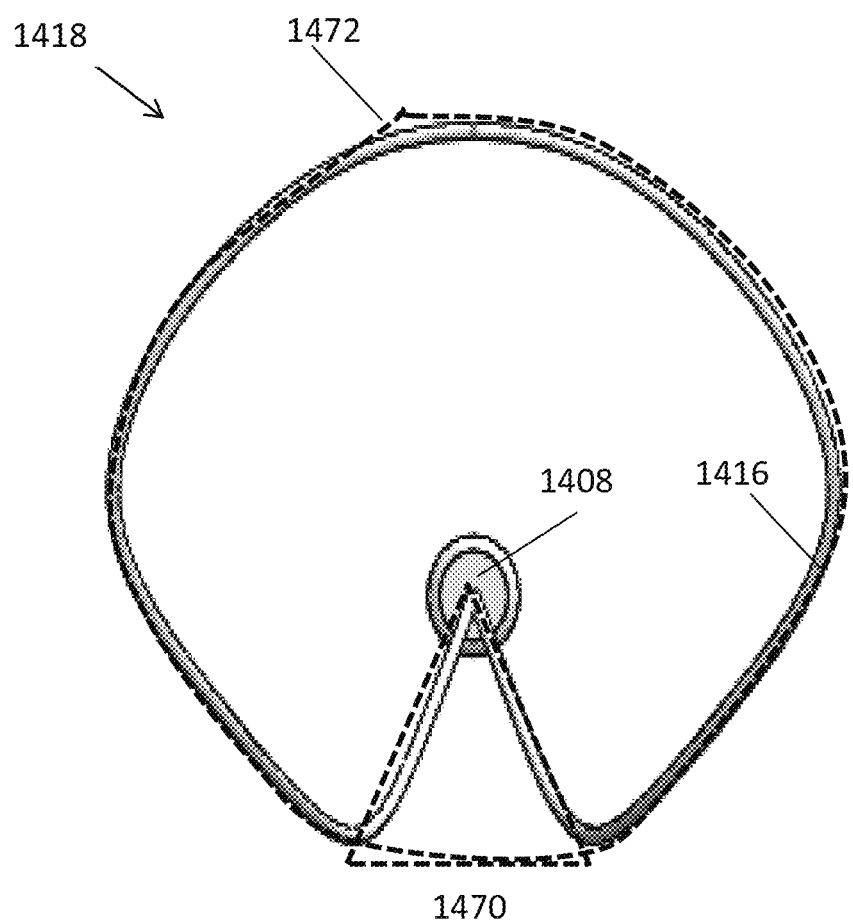
Figure 15:
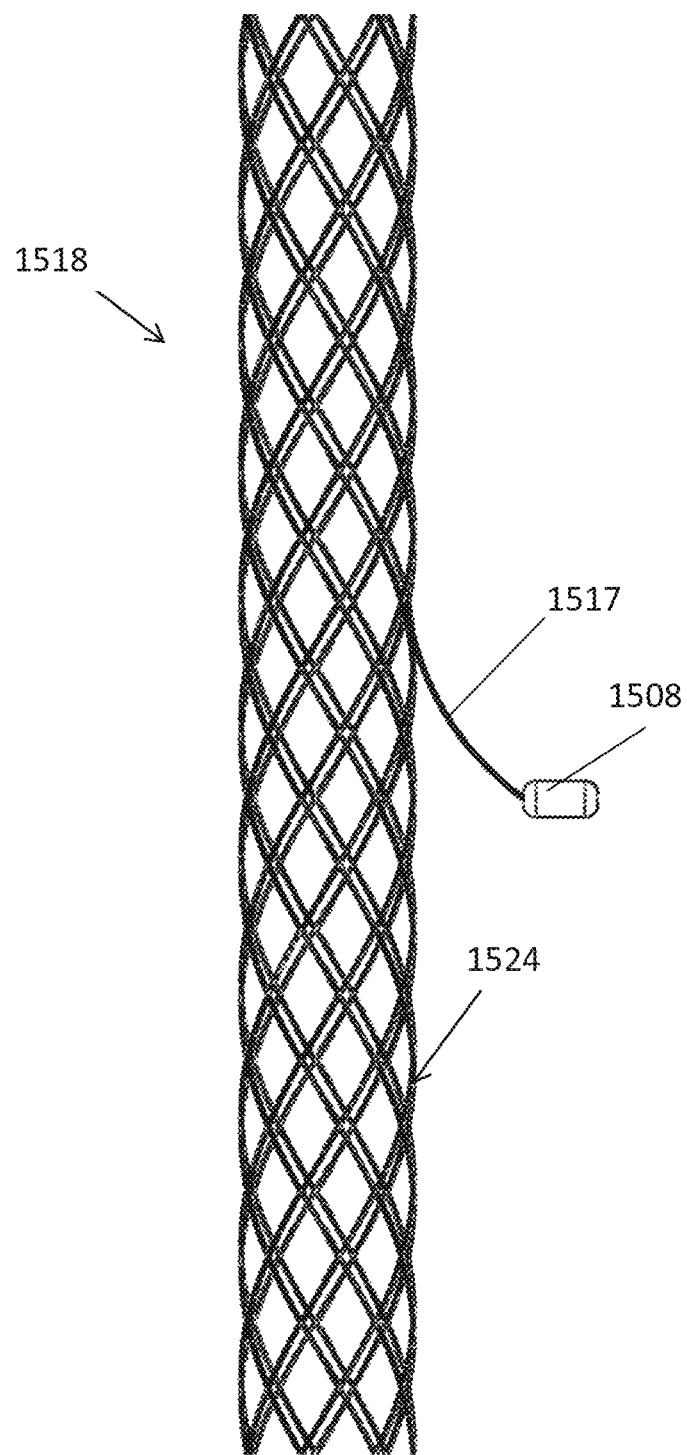
Figure 16A:
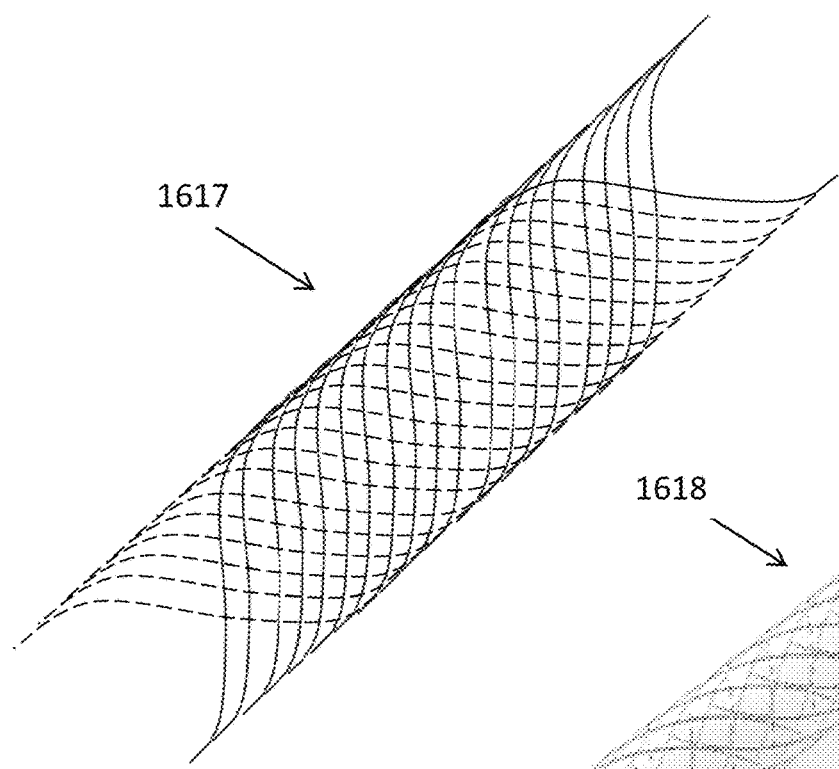
Figure 16B:
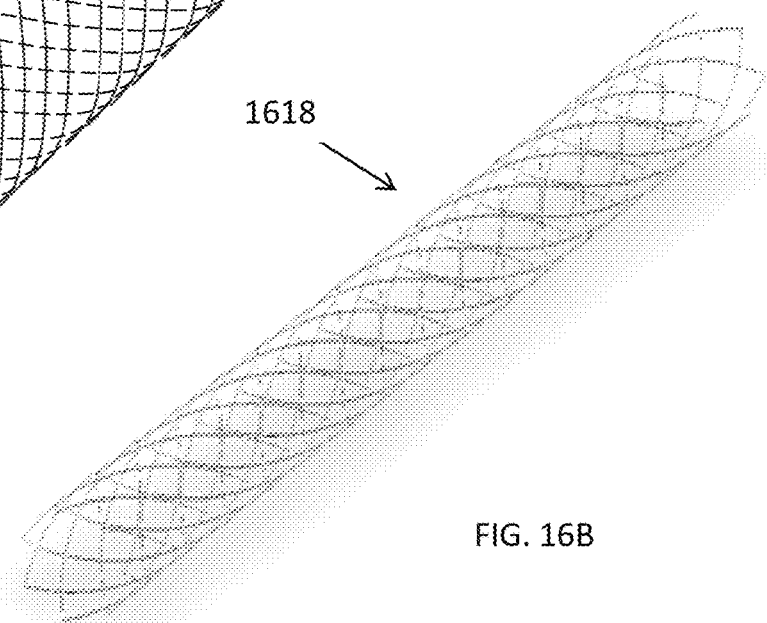
Figure 16C:
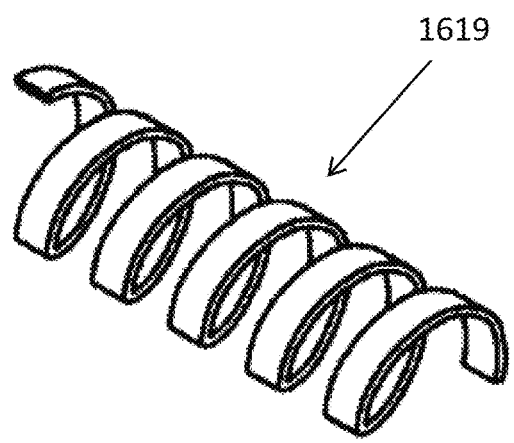
Figure 17A:
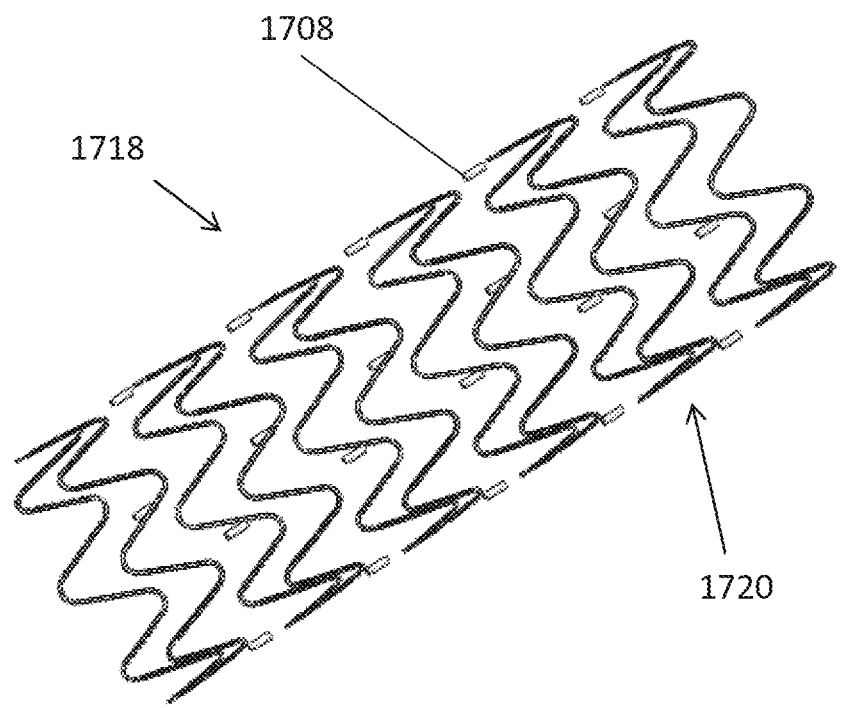
Figure 17B:
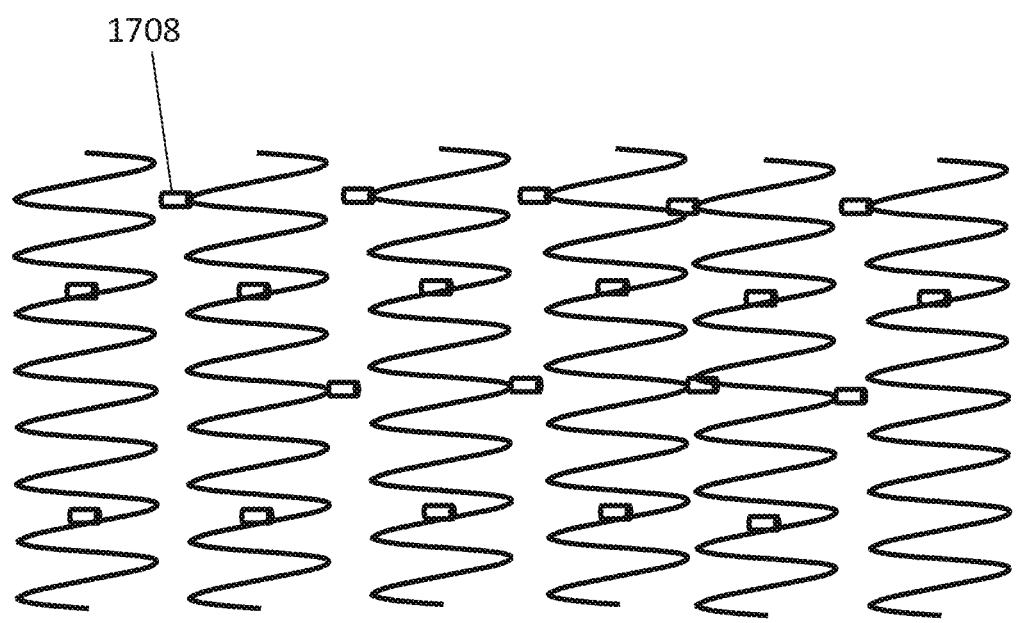
Figure 18:
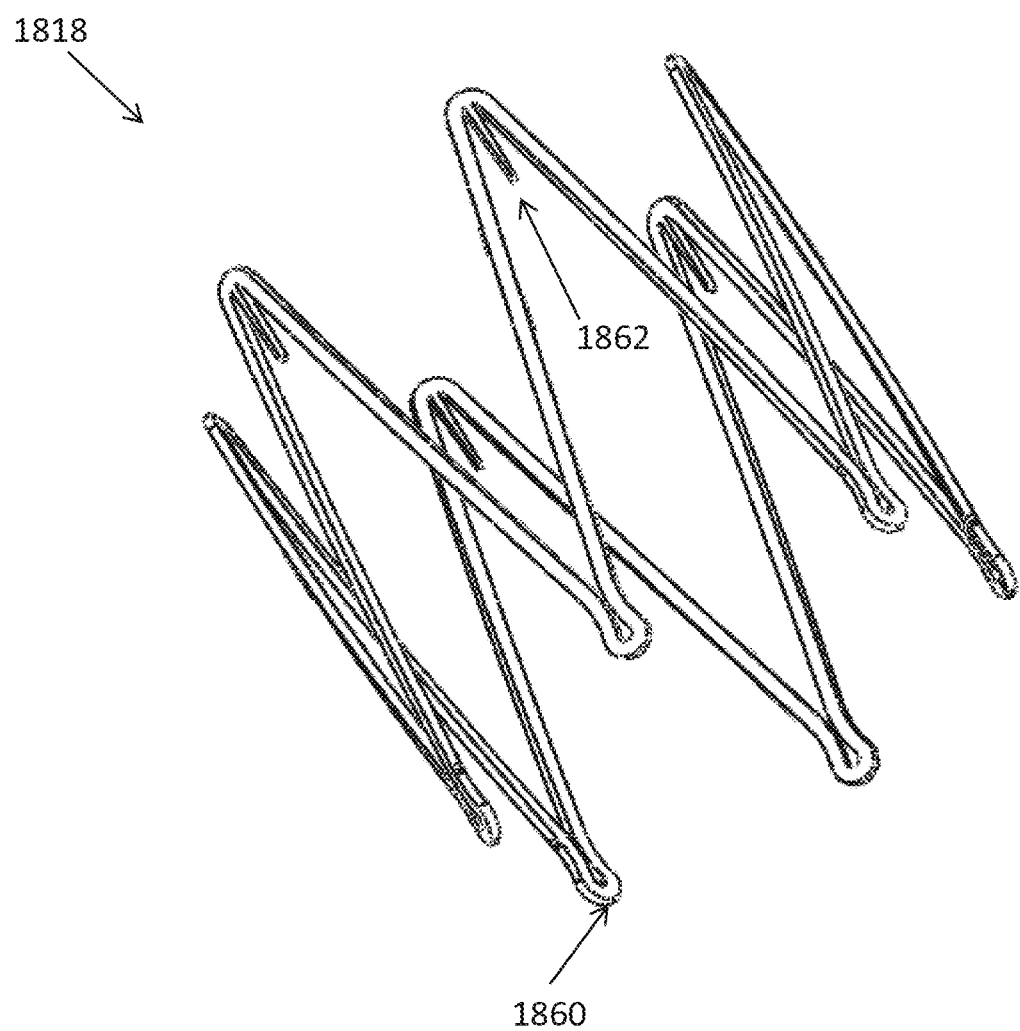
Figure 19A:
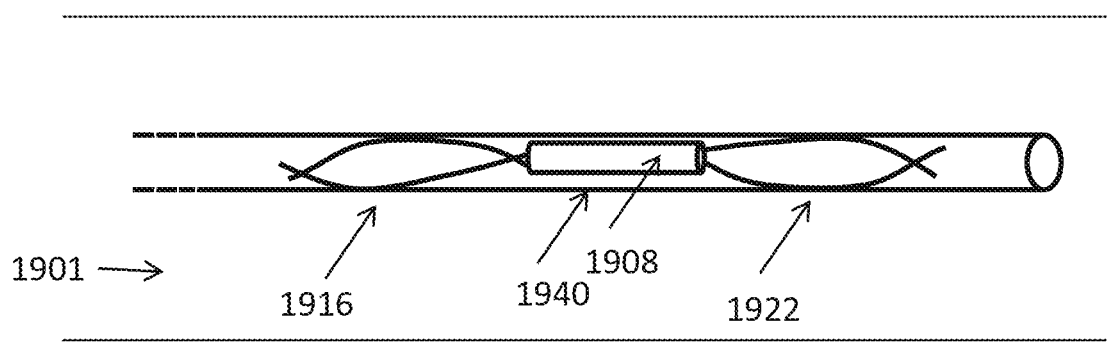
Figure 19B:
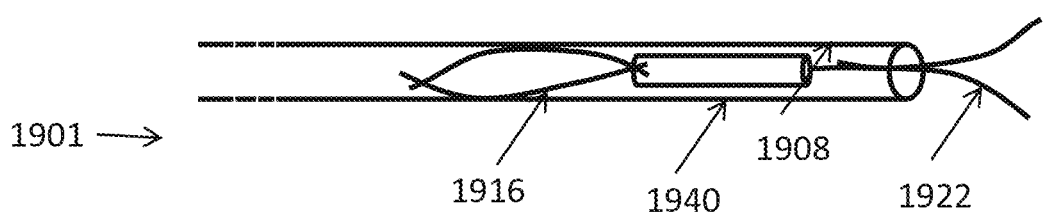
Figure 19C:
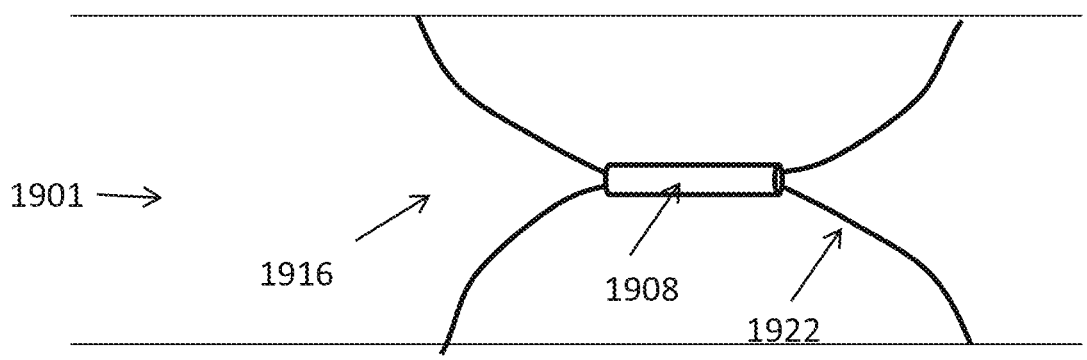
Figure 20:
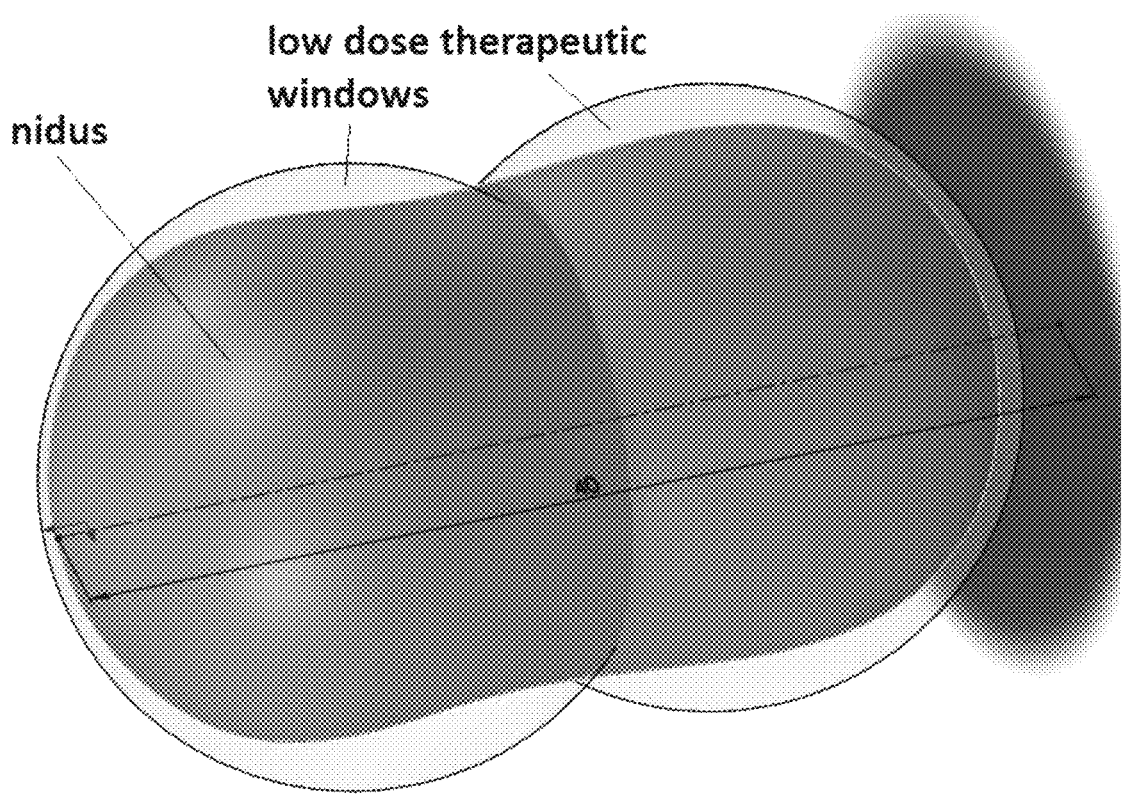
Figure 21:
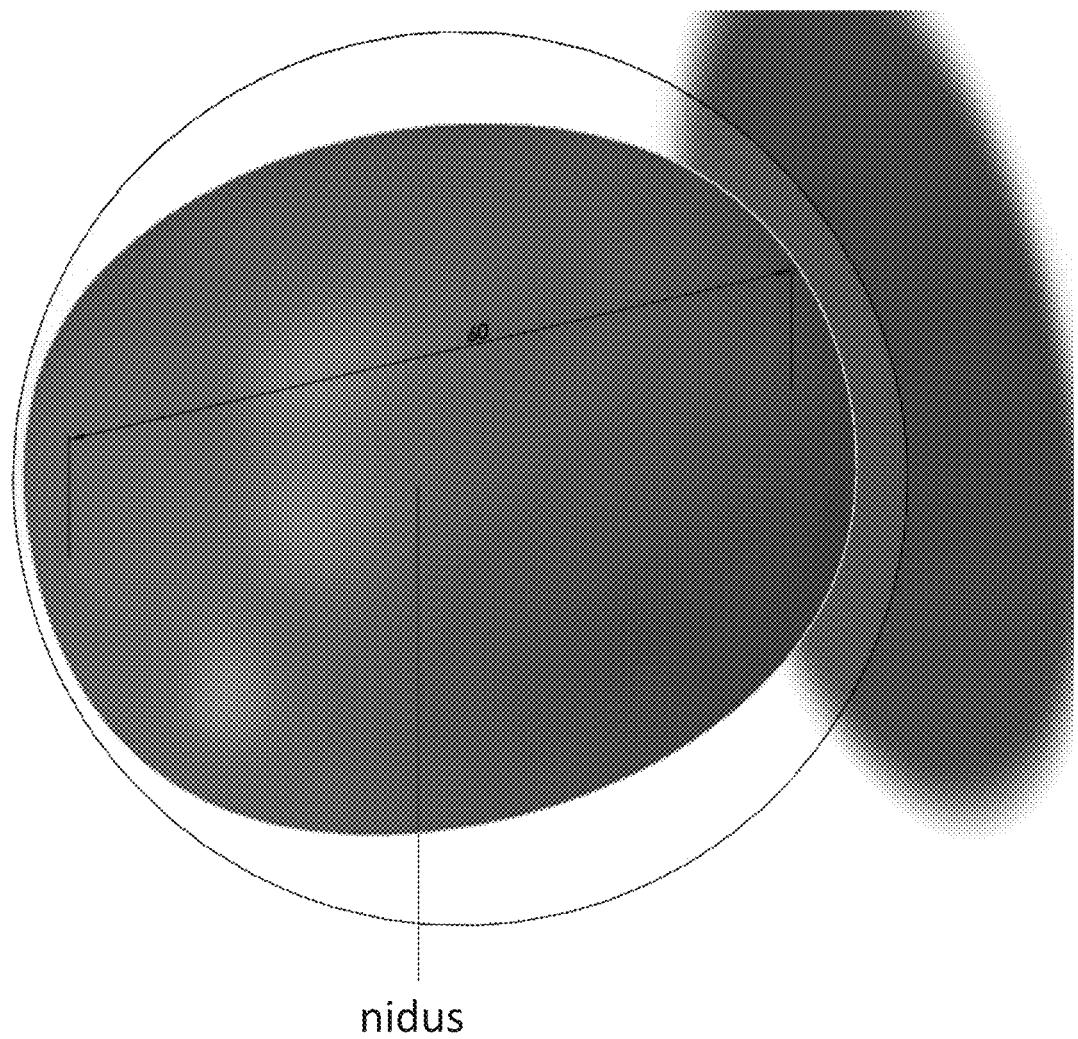
Figure 22:
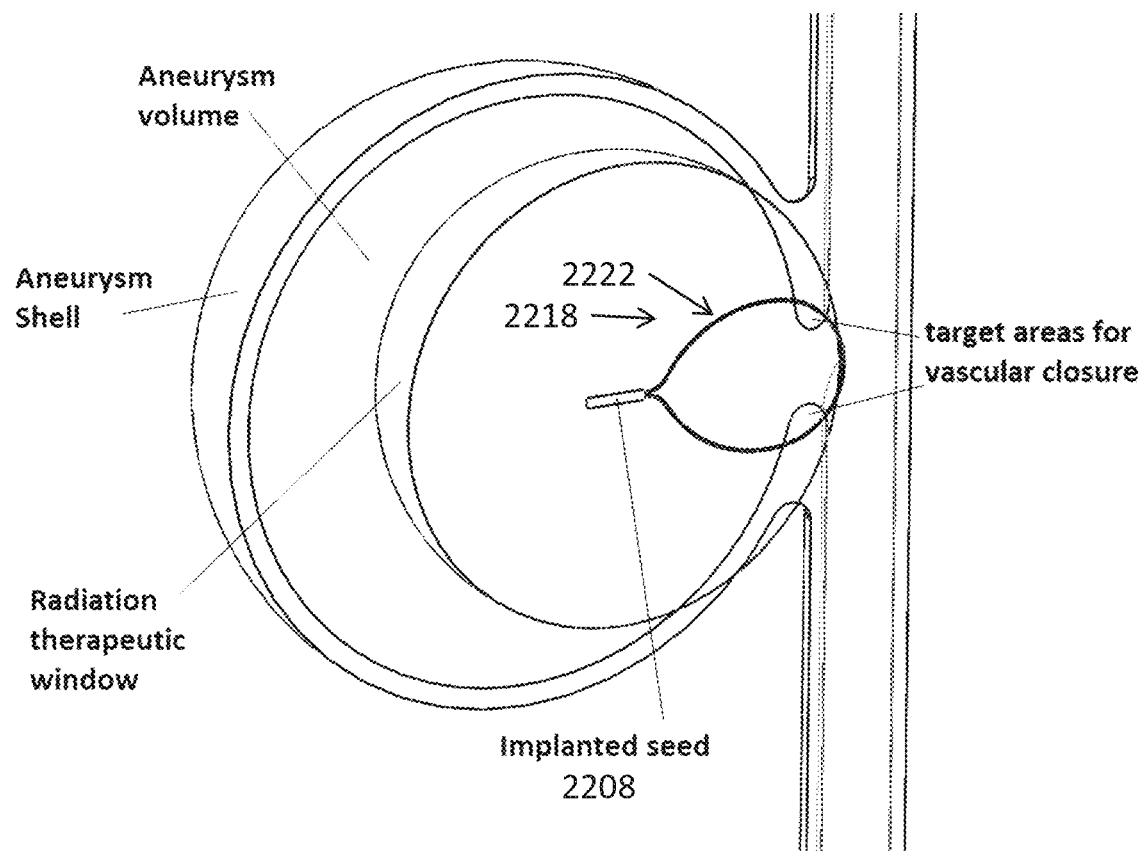
Figure 23:
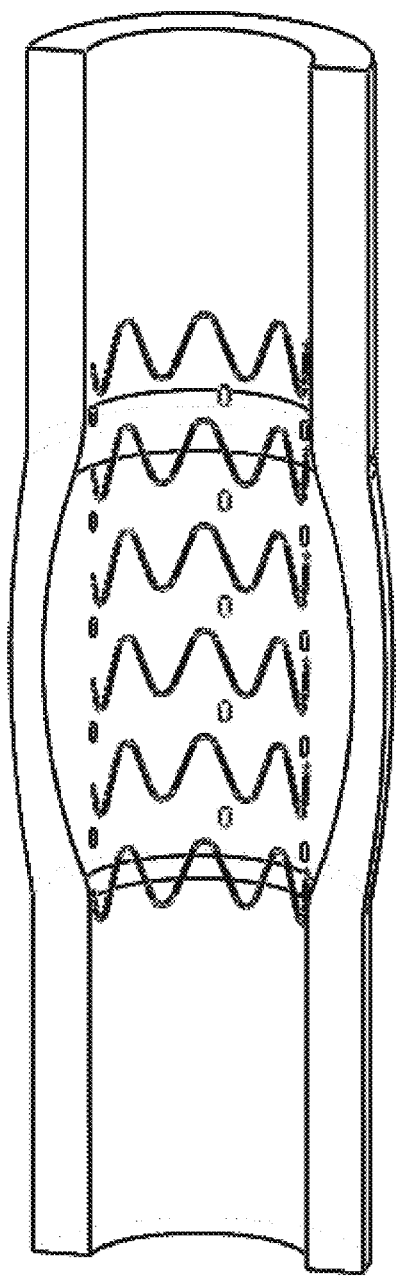
Figure 24A:
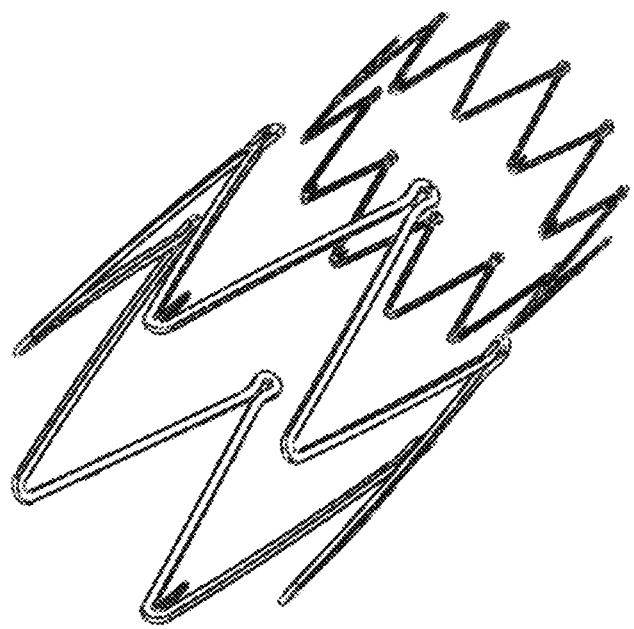
Figure 24B:
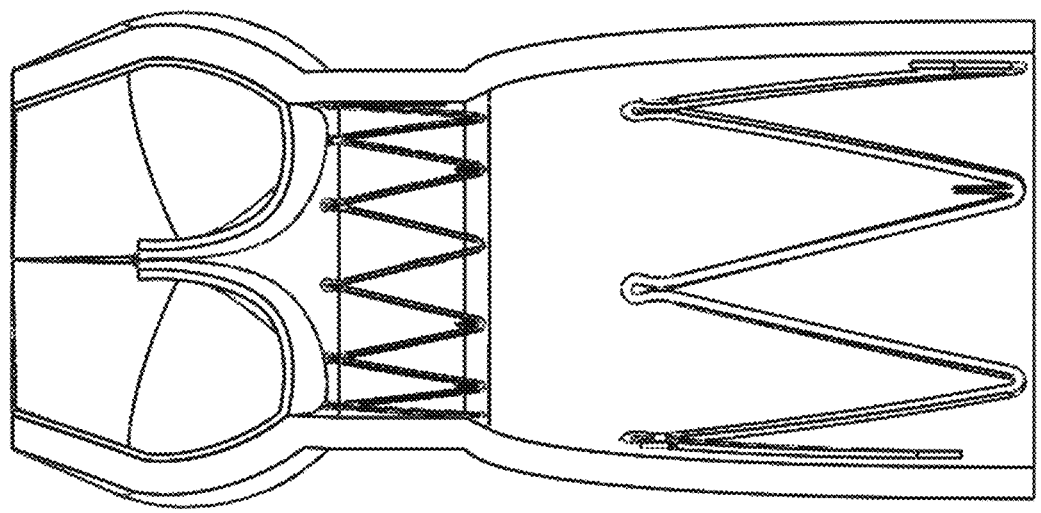
Figure 25:
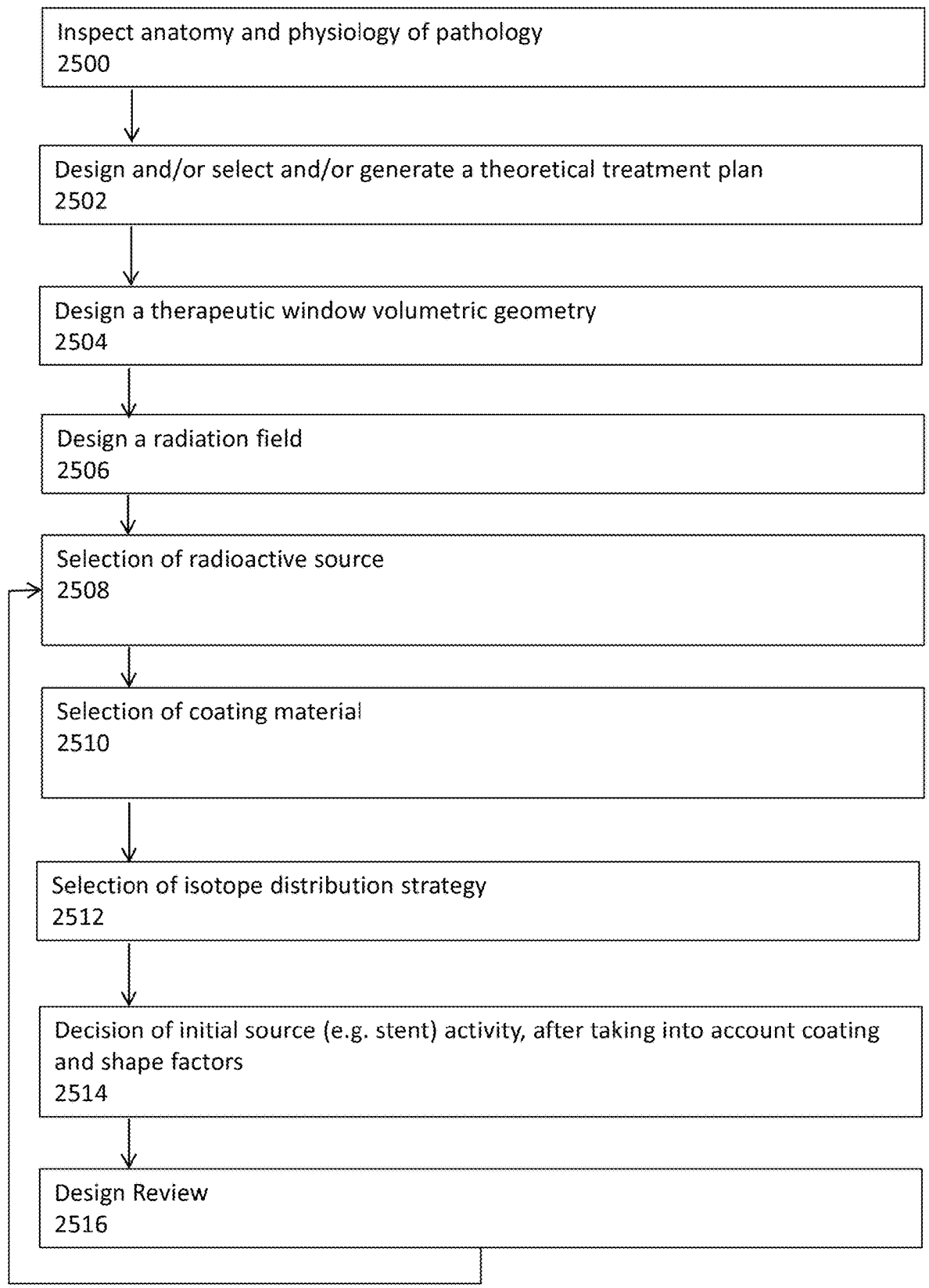
Figure 26:
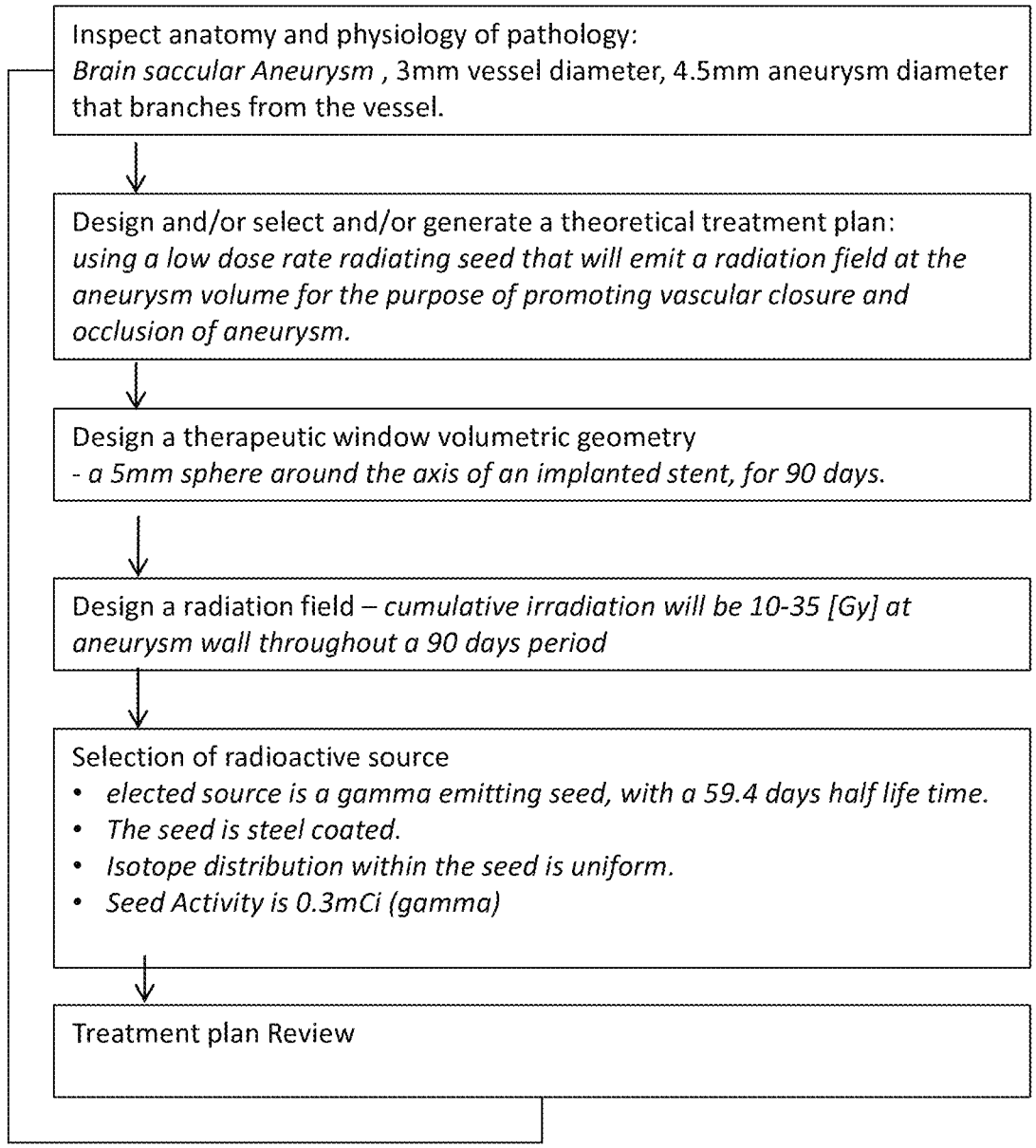
Figure 27:
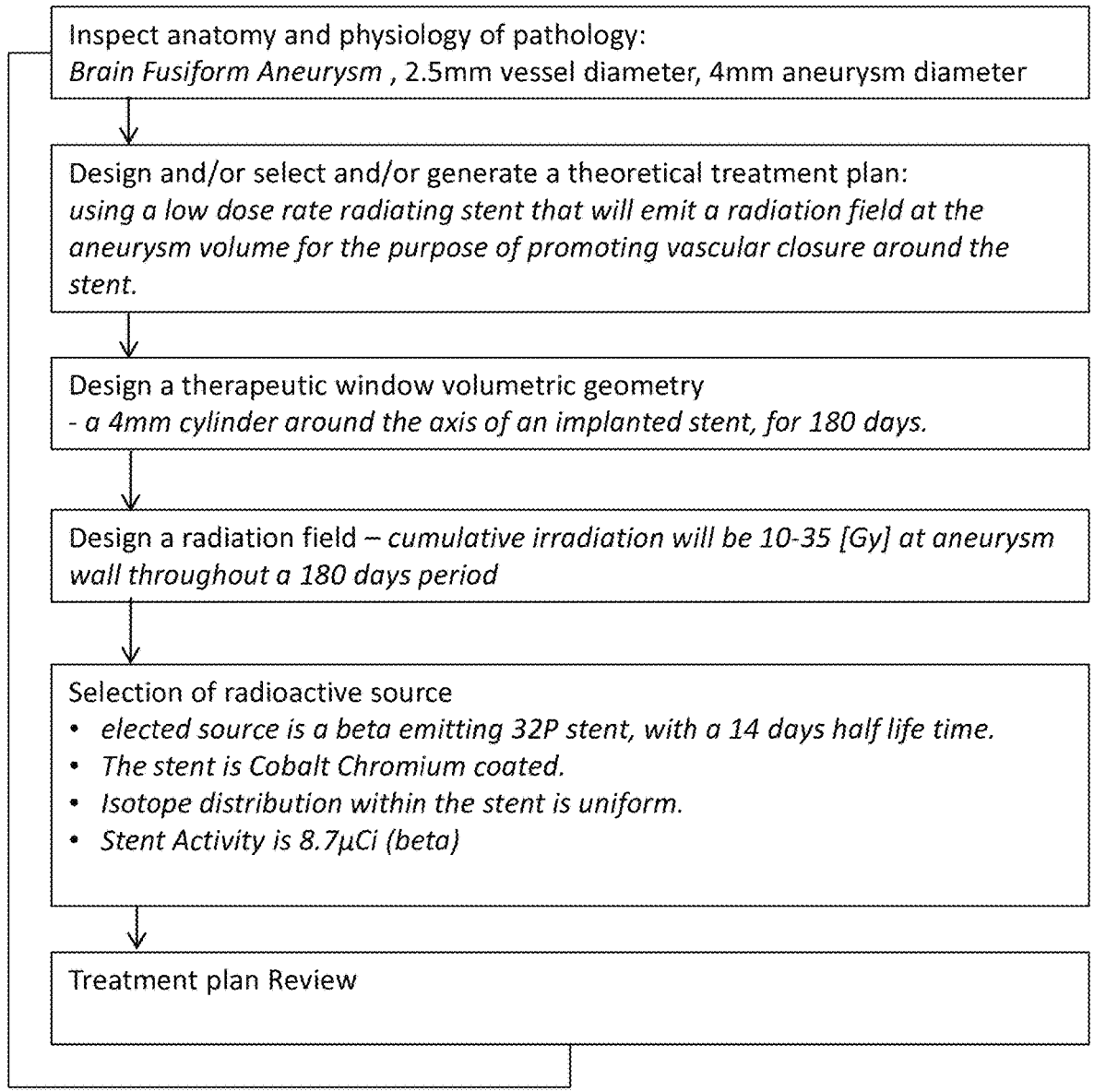
Figure 28:
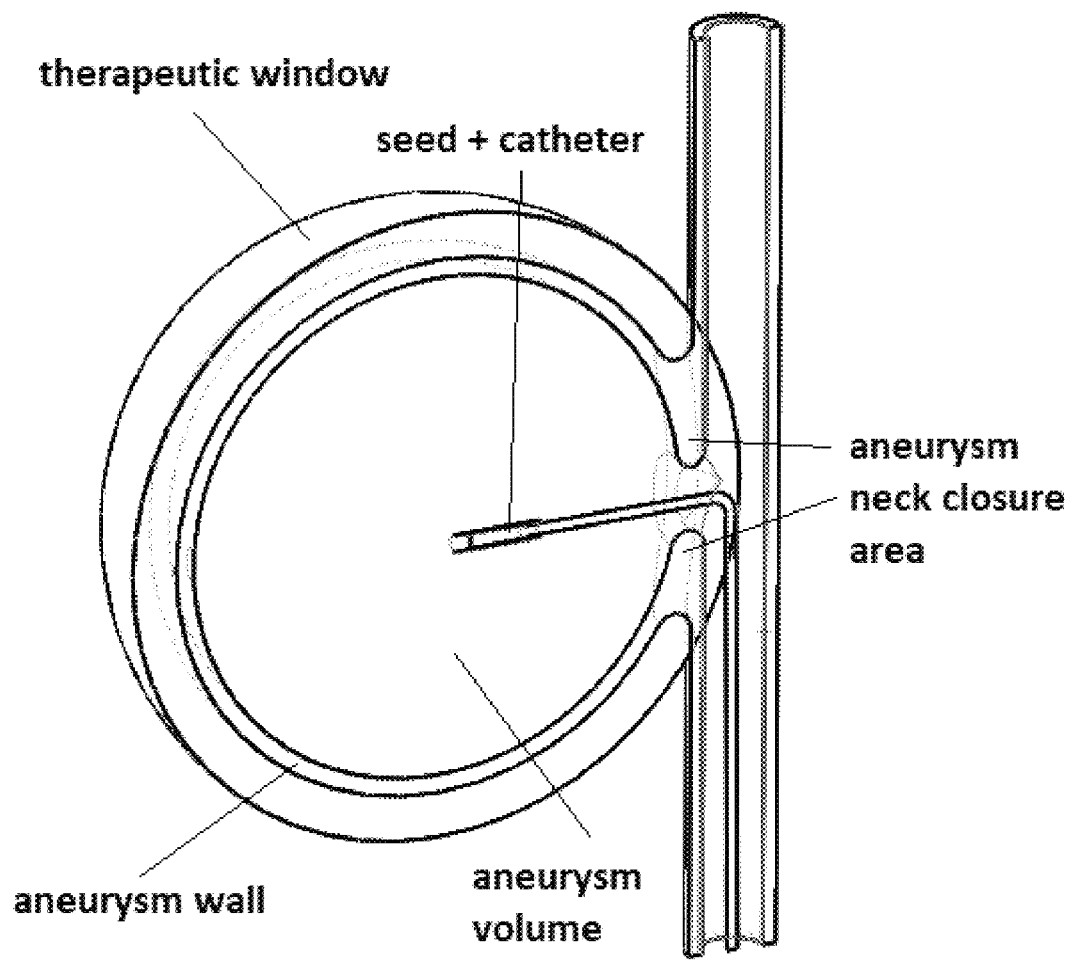
Figure 29:
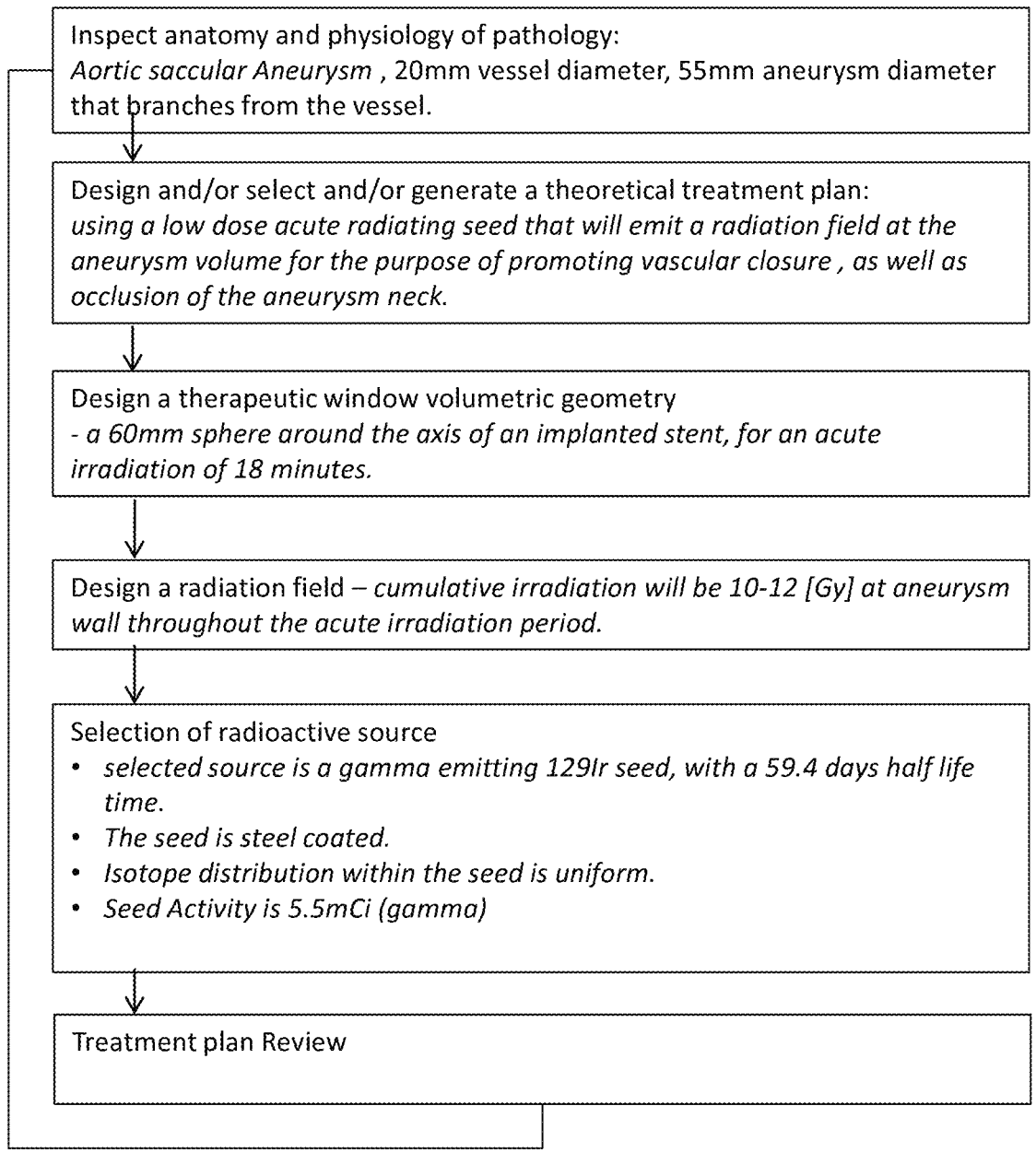

FIGS. 2A-B are simplified schematic cross sections of a vessel undergoing treatment, according to some embodiments of the invention;

FIG. 2C is a simplified schematic cross section of a vessel where the cross section is taken perpendicular to a long axis of the vessel;

FIGS. 2D-F are simplified schematics of the vessel cross sections illustrated in FIG. 2C illustrating injury, according to some embodiments of the invention;

FIG. 3 is a simplified schematic of vessel treated with acute radiation, according to some embodiments of the invention;

FIG. 4A illustrates simulated radiation rate levels with distance from a point radiation source at different times after source implantation, according to some embodiments of the invention;

FIGS. 4B-F illustrate simulated radiation rate radiation levels with distance from point sources, according to some embodiments of the invention;

FIGS. 4G-H illustrate simulation results of exemplary emitted cumulative radiation received by tissue, with distance from a source, for exemplary isotopes, according to some embodiments of the invention;

FIG. 4I is a table showing exemplary radiation rates and total radiation doses, according to some embodiments of the invention;

FIG. 4J is a table showing potential for hyperproliferative vascular growth and/or negative remodeling potential with respect to total radiation dose and irradiation rates, according to some embodiments of the invention;

FIG. 4K is a graphical representation of the table of FIG. 4J, according to some embodiments of the invention;

FIGS. 5A-C are simplified schematic cross sections of treatment of a vessel over time, according to some embodiments of the invention;

FIG. 6A is a simplified schematic cross section of a radiation source within a vessel, according to some embodiments of the invention;

FIGS. 6B-C are a simplified schematics section of radiation sources positioned outside a vessel to be treated, according to some embodiments of the invention;

FIG. 7 is a simplified schematic cross section of a vessel being treated with a plurality of radiation sources, according to some embodiments of the invention;

FIG. 8A is a simplified schematic of a blood vessel including an aneurysm;

FIGS. 8B-E are simplified schematics illustrating treatment of the aneurysm of FIG. 8A, according to some embodiments of the invention;

FIGS. 9A-D are simplified schematics illustrating treatment of a vascular malformation, according to some embodiments of the invention;

FIG. 10 is a simplified schematic illustrating treatment of a valve, according to some embodiments of the invention;

FIG. 11 is a simplified schematic of an anchoring device including a connector, according to some embodiments of the invention;

FIG. 12 is a simplified schematic of an anchoring device, according to some embodiments of the invention;

FIG. 13 is a simplified schematic of an anchoring device, according to some embodiments of the invention;

FIGS. 14A-C are simplified schematics of an anchoring device, according to some embodiments of the invention;

FIG. 15 is a simplified schematic of an anchoring device, according to some embodiments of the invention;

FIG. 16A-B are a simplified schematics anchoring devices, according to some embodiments of the invention;

FIG. 16C is a simplified schematic of an anchoring device, according to some embodiments of the invention;

FIG. 17A is a simplified schematic of an anchoring device, according to some embodiments of the invention;

FIG. 17B is a simplified schematic plan view of the anchoring device of FIG. 17A, according to some embodiments of the invention;

FIG. 18 is a simplified schematic of an anchoring device, according to some embodiments of the invention;

FIGS. 19A-C are simplified schematic illustrating delivery of an anchoring device to a treatment area, according to some embodiments of the invention;

FIG. 20 is a simplified schematic of treatment of a vascular malformation nidus by a plurality of sources, according to some embodiments of the invention;

FIG. 21 is a simplified schematic of treatment of a vascular malformation, according to some embodiments of the invention;

FIG. 22 is a simplified schematic of treatment of an aneurysm, according to some embodiments of the invention;

FIG. 23 is a simplified schematic of a treatment using an irradiating supporting structure, according to some embodiments of the invention;

FIG. 24A is a simplified schematic of an anchoring device, according to some embodiments of the invention;

FIG. 24B is a simplified schematic of treatment of a valve, according to some embodiments of the invention;

FIG. 25 is a flow chart of a method, according to some embodiments of the invention;

FIG. 26 is a flow chart of an method of an exemplary treatment, according to some embodiments of the invention;

FIG. 27 is a flow chart of a method of an exemplary treatment, according to some embodiments of the invention;

FIG. 28 is a simplified schematic of acute treatment, according to some embodiments of the invention; and FIG. 29 is a flow chart of a method of an exemplary treatment, according to some embodiments of the invention.

DESCRIPTION OF SPECIFIC EMBODIMENTS OF THE INVENTION

The present invention, in some embodiments thereof, relates methods and devices for radiative treatment of tissue and, more particularly, but not exclusively, to methods and devices for radiative treatment of blood vessels.
Overview A broad aspect of some embodiments of the invention relates to methods and devices for treatment of vascular related disorders using low level radiation (where exemplary radiation levels as described in this document are also herein termed "therapeutic window" and/or "therapeutic range"). In some embodiments, vascular related disorders include treating of vascular disease, valvular disease (e.g. heart valve/s, vein valve/s) and vasculature associated with tumors.

In some embodiments, treatment includes constriction of one or more vessel which, in some embodiments, extends to closure of one or more vessel and/or lumen. Although, typically treatment is used to constrict and/or close blood vessel/s associated with a malformation, it should be appreciated that, in some embodiments, treatment includes and/or consists of closure of healthy vessel formation/s. In some embodiments, treatment is of mammals e.g. humans.

In some embodiments, vessel types treated include one or more of arteries elastic arteries, distributing arteries, arterioles, capillaries, venules, veins, large collecting vessels (e.g. subclavian vein, jugular vein, renal vein, iliac vein, venae cavae).

In some embodiments, different radiation levels effect different stenosis rates and/or extents in different types of tissue. In some embodiments, a vessel type or type/s are selected for stenosis by the selection of radiation levels e.g. to target a vessel type within a target region.

In some embodiments, the radiation level and/or dose is selected to encourage vessel cell hyperproliferation e.g. hyperproliferation of smooth muscle cells (SMCs) in blood vessel/s. Additionally or alternatively, in some embodiments, the radiation level and/or total quantity is selected to encourage negative remodeling of one or more vessel (e.g. where inflammatory activity e.g. as result of radiation, results in adventitial fibrosis"] and/or vessel shrinkage). It is noted that fibrosis due to inflammation may be a more gradual process than fibrosis due to scarring due to radiation damage.

In some embodiments, the radiation is ionizing radiation. In some embodiments, the radiation level and/or total quantity is selected to cause partial (e.g. 50-98%, or 70%, or 80%, or 90%, or 95%, or 98%, or lower or higher or intermediate percentages closure of a diameter of the vessel) or full closure of one or more blood vessel.

In some embodiments, radiation levels are selected to at most damage the endothelial layer, for example causing minimal or no damage to vessel tunica media and/or tunica adventitia. In some embodiments, radiation levels are selected to cause minimal or no damage to vessel tunica intima. In some embodiments, radiation levels are selected to cause minimal or no damage to the endothelial layer of vessel/s being treated, where, for example, radiation applied causes minimal or no fenestration e.g. of the endothelial layer of vessel/s being treated. In some embodiments, damage to the vessel wall is of small extent, for example, to a portion of the depth of the endothelial layer and/or for a short duration.

In some embodiments, radiation levels are selected to result in less than 50%, or less than 30%, or less than 10%, or less than 5% cell death and/or lower or higher or intermediate percentages or ranges, in tissue (e.g. of lumen tissue and, in some embodiments, not of lumen fluid e.g. blood) treated with therapeutic window radiation levels.

This is a potential benefit over traditional brachytherapy and/or radio surgery where damage to the endothelial layer (e.g. fenestration), for example, associated with high radiation levels, where, in some cases continued high radiation levels mean that injuries (e.g. associated with mechanical and/or radiation injury, e.g. fenestration/s) do not heal or heal slowly. For example increasing risk of coagulation and/or atherosclerotic plaque and/or aneurysm genesis. Where, for example, high radiation levels also may contribute to fibrosis and/or necrosis e.g. of healthy tissue. For example, high radiation may contribute to edema formation within the tissue.

A further potential benefit of low radiation levels is reduced risk of positive vascular remodeling.

A further potential advantage of treatment using low level radiation e.g. as opposed to radiosurgery, is the ability to treat larger areas of tissue and/or to effect complete treatment using less procedures than traditional multi-modal techniques (e.g. radiosurgical techniques).

Potentially this reduces time taken for a complete treatment e.g. of a vascular malformation such as AVM, for example, in contrast to existing treatment techniques. For example, generally multi-modal treatment techniques such as traditional radiosurgery take 2-3 years to treat vascular formations.

In some embodiments, the radiation level is configured to gradually effect partial and/or full closure, for example, in a time span of one day to one week, for example, in a time span of one week to one month, or in a time span of one month to six months. For example in a time span of 1-12 months, or 2-10 months, or 2-8 months or 3-6 months, or about 4 months, or lower or higher or intermediate times or ranges. In some exemplary embodiments of the invention, the closure is measured as reduction in diameter, for example, being between 0.2 and 4 mm/week, for example, between 0.4 and 2 mm/week.

A potential advantage of gradual closure of the vessel/s being treated is that changes to pressure and/or flow are gradual, potentially resulting in less risk of coagulation and/or hemorrhage and/or rupture e.g. than embolization and/or surgical resection techniques which alter pressure and/or flow values rapidly e.g. instantly after treatment. A further potential advantage of the gradual closure is that the vascular physiology adapts to the closure (e.g., by generating collaterals, which may be especially valuable in the brain or other critical tissue).

A further potential advantage of gradual closure of the vessels is the ability to treat large regions e.g. larger regions than may be treated in one endovascular embolization treatment session and/or to effect complete treatment in fewer treatments (e.g., 1, 2 or 3) than traditional multi-modal embolization and/or radiosurgical techniques.

A potential benefit of gradual closure of vessel/s and/or low radiation level/s is that, in some embodiments, treatment of a vascular malformation, is achieved using fewer procedures (e.g. invasive treatments) than possible with embolization and/or radiosurgery and/or surgical resection technique/s. For example, in some embodiments, a vascular malformation is treated in 1-5 treatments, or 1-3 treatments (where one or more of the treatments is an invasive treatment e.g. a cauterization procedure) or in a single treatment, for example, a single invasive treatment, e.g. a single catheterization procedure, or in lower or higher or intermediate numbers or ranges of treatments.

In some embodiments, the treatment includes exposure of one or more treatment area to acute administration of radiation. Additionally or alternatively, in some embodiments, the treatment includes exposure of one or more treatment area to chronic administration of radiation, optionally using an implant.

In some embodiments, one or more radiation source (also herein termed "source") is delivered to a treatment site and/or to a location in proximity to a treatment site such that where radiation from the source's is received by the treatment site. In some embodiments, one or more source is delivered endovascularly e.g. using catheterization techniques. Alternatively or additionally, in some embodiments, one or more radiation source is delivered subcutaneously and non-vascularly e.g. directly via needle e.g. to the treatment site and/or a region in proximity to the treatment site.

In some embodiments, radiation treatment includes one or more features as known in the art of brachytherapy, for example, material, geometry, implant shape, delivery system, extraction system and/or planning methods and/or software but with radiation level/s set according to aspects of some embodiments of the invention e.g. as described within this document. In some exemplary embodiments of the invention, the geometry of an implant or implant carrying structure is selected to allow vascular collapse, for example, as described herein below In some embodiments, one or more radiation source is configured to be removed, for example, including one or more retrieval device (e.g. including one or more feature as known in the art of retrieving and/or relocating vascular device/s and/or brachytherapy device/s). For example, in some embodiments, a source is connected to and/or an elongated element (e.g. string, wire) by pulling on, in some embodiments, the source is moved e.g. extracted from the patient and/or relocated to additional treatment site/s.

In some embodiments, the radiation source is a mesh e.g. a mesh graft which includes radiative isotope/s e.g. as known in the art of grafting and/or radiotherapies but with radiation levels e.g. as described within this document. In some embodiments, the mesh (or other structure) is planar. In some embodiments, the mesh is sufficiently thin and/or malleable for the mesh to be shaped to a shape of a treatment area e.g. lumen wall. In some embodiments, the graft includes and/or is composed of polymer which contains radiative isotope/s. In some embodiments, the graft is configured to be dissolvable in vivo e.g. after a treatment time period.

Optionally, in some embodiments, the source is removed after treatment, e.g. by removal of the needle e.g. by extracting the source through a catheter (e.g. source attached to a string). Alternatively or additionally, in some embodiments, the radiation source is polymer that contains a radiative isotope or isotopes e.g. a polymer configured to dissolve and/or dissipate in vivo e.g. a dissolvable graft.

In some embodiments, the radiation source is a seed where radioactive isotope/s are encapsulated e.g. by a non-radioactive encapsulation material.

In some embodiments, delivery of source's (e.g. seed/s) enables targeted treatment of region/s of tissue. For example, the radiation treatment potentially affecting the vascular irregularity e.g. tumor volume e.g. tumor vascular malformation nidus e.g. aneurysm e.g. paravalvular leakage site e.g. valvular disease site, for example, while affecting surrounding tissue minimally or without affecting surrounding tissue. Accurate treatment of target tissue contrasts with existing techniques, for example, radiosurgery, which involves risk of irradiation and ablation of healthy tissue.

In some embodiments, low levels of radiation an associated small regions of affected tissue enable targeting of tissue to be treated, for example, while causing minimal or no stenosis to non-target region/s e.g. vessel/s and/or vessel area's.

An aspect of some embodiments of the invention relates to selection of therapeutic window radiation size and/or geometry for treatment of a target tissue area volume and/or topography. For example, in some embodiments, a source is selected (and/or designed) to affect a lumen in which it is positioned e.g. where therapeutic window radiation size extends to 1.1-10, or 1.5-5, or lower or higher or intermediate multiples or numbers of a maximum and/or average lumen cross sectional dimension at the location of the source. In some embodiments, one or more source is configured to irradiate an area of tissue adjacent and/or surrounding the lumen in which the source is positioned, for example a therapeutic window radiation extending to a volume of 3-50 times, 5-30, 10-20 or lower or higher or intermediate multiples or numbers of a maximum and/or average lumen cross sectional dimension at the location of the source. In some embodiments, one or more source emits radiation at a therapeutic window at higher levels to one or more region of the lumen e.g. for treatment of non-symmetries e.g. aneurysm, where, for example, in some embodiments, 5-30% of a portion of a lumen wall receives 35-90% or 70-90% of the radiation received by tissue.

It is noted that in some embodiments of the invention the therapeutic window starts at a distance greater than zero form the source. However, the only tissue in this region may be blood, which is replaced fast enough to reduce its total dosage. In some cases, planning or source placement is imperfect and some tissue lies within a radiated volume where cellular damage is caused, rather than within the therapeutic window described herein.

In some exemplary embodiments of the invention, as the source decays, the therapeutic window changes. Optionally, this is selected so as to match (e.g., within a factor of 2) the shrinkage of the vessel lumen.

In some embodiments, therapeutic window radiation levels are located asymmetrically to a device (e.g. anchoring device) to which they are connected and/or to a vessel in which they the source's emitting the radiation is located. In some embodiments, the radiation source's are positioned with respect to a device (e.g. anchoring device) and/or the lumen to produce a desired therapeutic window shape (e.g. based on treatment tissue volume shape).

Optionally, in some embodiments, at least a portion of a treatment region is injured, for example, by one or more of exposure to one or more of sclerosing agent/s, mechanical injury, high dose radiation, ablation (e.g. one or more of heat, ultrasound, cryogenic, laser, RF, microwave).

In some embodiments, injury is limited to a target region meaning that, potentially, radiation affecting non-injured area/s will cause minimal or no stenosis of non-target region/s e.g. vessel/s and/or vessel area/s. For example, in some embodiments, an injury extent (e.g. a volume of tissue) is enclosed by and/or smaller than that irradiated with exemplary levels of radiation. Alternatively, in some embodiments, an injury extent (e.g. a volume of tissue) is larger and/or extending beyond a region of tissue that irradiated with exemplary levels of radiation.

Optionally, in some embodiments, injury is endogenic (e.g. an aneurysm inner wall) and/or results in endothelial dysfunction and/or vascular environment inflammation.

In some embodiments, the injury is low level injury. For example, configured to affect the endothelial layer of one or more vessel (e.g. blood vessel). In some embodiments, injury includes micro-injury to a portion of an endothelial layer of vessel/s. Without necessarily wanting to be bound by theory, it is thought that injury, according to embodiment/s described in this document, initiates migration of SMCs to the endothelial layer and/or hyperproliferation e.g. of the SMCs. For example, the selected radiation levels accelerating and/or enhancing the extent and/or volume of cell hyperproliferation. In some embodiments, hyperproliferation increases the speed at which stenosis and/or closure of vessel/s being treated occurs.

In some embodiments, injury is minimal such that the effected layer/s heal within a short time span e.g. less than a week, e.g. 1-3 days. In some embodiments the injury is for short duration, e.g. with respect to a treatment duration, for example, where injury is applied for 0.01-500% or 0.01-20% or 0.01-10% or 1-10% of a treatment duration or lower or higher or intermediate ranges or percentages.

Alternatively or additionally, in some embodiments, injury is chronic, for example, for a longer time period and/or for a significant proportion of the treatment duration (e.g. 20-100% of the treatment duration, or lower or higher or intermediate percentages or ranges) e.g. by positioning and/or implanting a continuously injuring element (e.g. radiation source, material eluting sclerosing agent/s) at the treatment site.

In some embodiments, injury is selected and/or radiation levels are selected such that vessel stenosis and/or closure occurs at the injured site e.g. via hyperproliferation. Where, for example, in some embodiments, vessel stenosis drops outside the injured region (e.g. by 10-95%, or 20-90%, or lower or higher or intermediate ranges or values). Potentially, injury increases accuracy of targeting of treatment a potential benefit being the ability to target pathologies e.g. while minimally and/or without damaging healthy tissue.

In some embodiments, sclerosing agent/s for injuring a treatment site are applied with marking agent/s (e.g. radiopaque marking agent/s), for example, marking the injured area/s. In some embodiments, a concentration of sclerosing agent/s is sufficiently high to cause injury but at a low enough so that the agent/s do not cause significant coagulation and/or thrombosis.

A potential benefit of mild injury is reduced risk of vessel elastic recoil and/or vaspasm and/or positive vascular remodeling. A further potential benefit of mild injury is reduced risk of coagulation and/or atherosclerotic response to the injury.

In some exemplary embodiments of the invention, the injury is targeted to certain tissue, for example, within 0-3, for example, 0.3-2 mm of tissue to be affected, which lies within the therapeutic window. Optionally, damage outside of the therapeutic window of the radiation is allowed.

In some embodiments, one or more source is selected for suitability for a treatment (e.g. radiation levels with respect to geometry of the lumen and/or treatment area). In some embodiments, a source is selected to be suitable to cause gradual closure of a lumen in which it is located at a distance of less than 30 mm, or 20 mm, or 10 mm, or 5 mm or 1 mm from said source, for example, at a distance of 1-100 mm, or 1-10 mm, or 10-100 mm, 20-50 mm or lower or higher or intermediate ranges or distances from said source.

An aspect of some embodiments relates to positioning and/or anchoring one or more seed using an anchoring structure. In some embodiments, the structure is configured to anchor one or more seed to a central region of a lumen e.g. of a lumen being treated. Alternatively or additionally, in some embodiments, the structure is configured to anchor one or more seed to a region proximal to and/or in contact with a wall of the lumen. In some embodiments, the structure is delivered vascularly e.g. through a catheter.

In some embodiments, the structure is an expandable structure, where, for example, the structure is expanded within a vessel to anchor the structure to the vessel. Where, for example, one or more portion of the structure is configured to elastically expand (e.g. upon release from a crimped configuration). Where, for example, in some embodiments, one or more portion of the structure is configured for plastic expansion (e.g. sufficiently thin and/or malleable to be balloon expanded). Where, for example, in some embodiments, the structure includes one or more hinge about which portion/s of the device rotate to expand the device. In some embodiments, a single device includes one or more elastically expandable portion and/or one or more plastically expandable portion and/or one or more hinge.

In some embodiments, a device includes one or more element shaped to anchor the device at axially separated locations along a lumen allowing at least 1 mm or at least 2 mm or at least 3 mm, or at least 5 mm or at least 10 mm, or 1-20 mm, or lower or higher or intermediate distances or ranges or allowing a space of 0.1-20, or 0.5-10 times, or lower or higher or intermediate multiples or ranges of a lumen average diameter at the device implantation region of the lumen between these locations—for luminal collapse on the element.

In some embodiments, the expandable structure does not support the lumen and/or minimally interferes with the lumen. For example, in some embodiments, the structure, when anchored (e.g. expanded) within the lumen, exerting minimal outward force on the lumen and/or exerting outward force on a small proportion of the lumen for example, the structure exerting outwards force on 0.1-20% or 0.1-5%, or lower, or higher, or intermediate ranges or percentages, of a portion of a lumen wall circumference in which the structure is located.

In some exemplary embodiments of the invention, the device supports wall lumen by only at axially spaced apart (e.g., between 1 and 40 mm, for example, between 3 and 10 mm, for example, between 4 and 6 mm) locations, so the lumen can collapse on the device.

Alternatively, in some embodiments, one or more portion of the expandable structure provides support to the vessel, e.g. includes and/or is a stent. In some embodiments, stent geometric feature/s are those as known, for example, in one or more of the arts of angioplasty e.g. cerebral and/or cardiovascular and/or peripheral.

In some embodiments, an anchoring device (e.g. expandable structure) and/or source is sized and/or shaped and/or elastically biased such that the device when deployed within a lumen affects the lumen minimally (e.g. allowing the lumen to constrict and/or close onto the device). In some embodiments, an anchoring device (e.g. expandable structure e.g. anchoring device/s as described within this document) and/or source is sized and/or shaped and/or elastically biased such that the device when deployed within a lumen affects flow within the lumen minimally.

In some embodiments, the device (e.g. expandable structure) is configured to collapse, for example as treatment results in constriction and/or closure of a vessel in which the structure is located (e.g. anchored). For example, in some embodiments, the provides radial support to a lumen (and/or outwards force and/or contacts the lumen) at a small proportion of the structure length e.g. long axis length, for example of 0.1-20%, or 1-5% or the device long axis length. Exemplary device (e.g. anchoring structure and/or device) long axis lengths are 0.1-500 mm, or 1-300 mm, or 3-100 mm, or 3-10 mm or lower or higher or intermediate lengths or ranges. Exemplary source long axis lengths are 0.01-50 mm, or 0.5-10 mm, or lower or higher or intermediate lengths or ranges.

For example, in some embodiments, minimal diameter tubular shapes (e.g. cylindrical tubes) containing the device (e.g. in expanded configurations) where, in some embodiments, the tubular shape is a theoretical construct used to understand the properties of the device when placed within a lumen and/or catheter. In some embodiments, tubular shapes containing the device contact the device at less than 30% or less than 20% or less than 10% or 0.1-30%, or 0.1-10%, or 0.1-5%, or lower or higher or intermediate percentages or ranges. In some embodiments, a maximum cross sectional area of said device is 10% of the cross sectional area of minimal diameter tubular shapes containing the device. Where for example, in some embodiments, a single device has a range of expanded configurations e.g. the minimal diameter tubular shapes include a more than one diameter tube e.g. a range of diameter tubes. For example, in some embodiments, an anchoring device (e.g. anchoring device/s as described within this document) is configured to anchor to one or more size e.g. diameter vessel.

In some embodiments, a projection of the where projection is along a long central axis of the device (e.g. for expanded configuration/s of the device) has an area which is 1-50% or, 2-30%, or lower or higher or intermediate percentages or ranges of a smallest sphere containing the projection.

In some embodiments, the structure (e.g. including expandable structures) includes one or more connector (e.g. one or more hook, e.g. including one or more feature as illustrated and/or described regarding hook 1162 FIG. 11 and/or hook 1162 FIG. 11, and/or hooks 1862 FIG. 18) configured to attach the structure to the vessel.

In some embodiments, the structure is not an expandable structure, for example, in some embodiments, the structure includes a radioactive source coupled to a connector (e.g. hook). In some embodiments a connector (e.g. hook) includes radioactive material e.g. the connector itself is the source.

In some embodiments, one or more radiation source is attached to a lumen using sutures and/or glue (e.g. glue used in embolization technique/s).

In some embodiments, the structure includes a single seed. In some embodiments, the structure includes a plurality of seeds.

In some embodiments, the structure includes dissolvable material, for example, dissolvable material including radio-isotopes.

Potentially, lower risks associated with gradual closure and/or low radiation levels, enable treatment of pathologies e.g. using embodiment/s described in this document, which would not be considered candidates for interventional treatment under existing treatment modalities.

In some embodiments, treatment using low level radiation is combined as an alternative or addition to traditional treatment/s e.g. endovascular embolization, stereotactic surgery, surgical resection, radiosurgery.

For example, in some embodiments, radioisotopes are incorporated into material used for endovascular embolization (e.g. a polymer, e.g. material/s as described in the section entitled "Exemplary source and/or seed structure and/or materials". In some embodiments, low level radiation e.g. configured to promote hyperproliferation and/or negative remodeling is emitted by the embolization material e.g. after an initial embolization.

An aspect of some embodiments of the invention relates to repurposing device/s known in the art of radiotherapy (e.g. brachytherapy) and/or frame structure/s known in the art of vascular treatment/s and/or radiotherapy (e.g. brachytherapy) for method/s and/or treatments e.g. as described within this document e.g. include low level radiation exposure to tissue. In some exemplary embodiments of the invention, actual brachytherapy devices or seeds which have a too low radiation level for brachytherapy are used for treatment as described herein.

Exemplary Method of Treatment

Figure 1A:
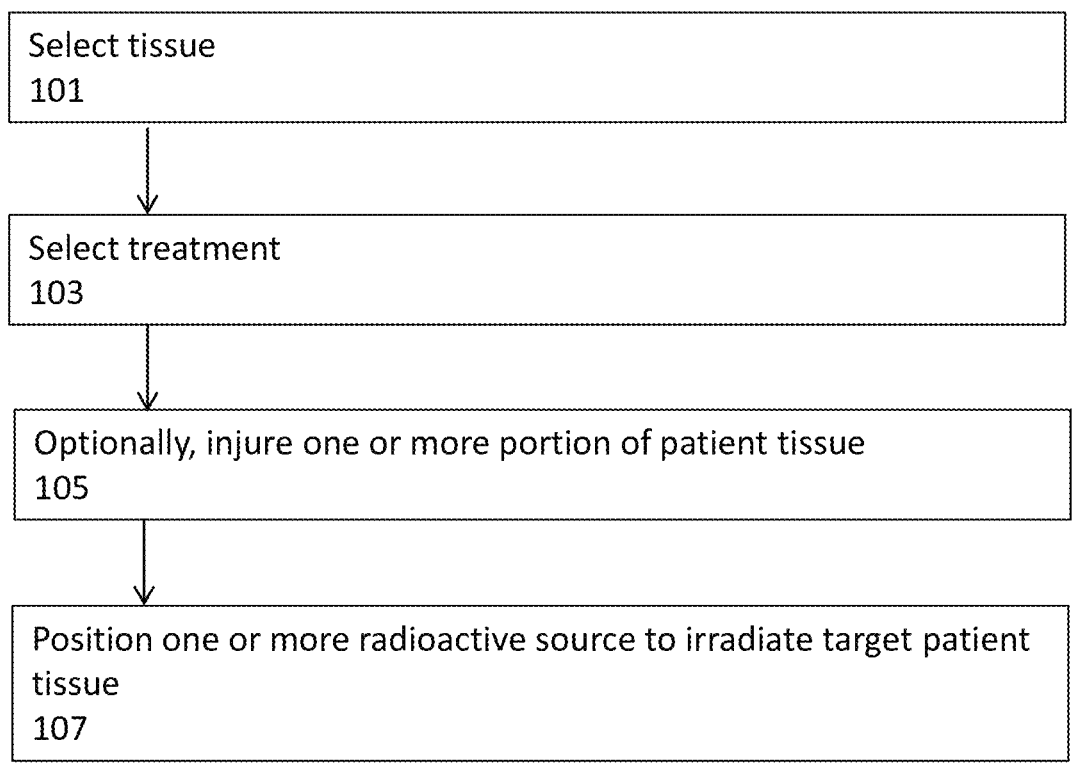
FIG. 1A is a flow chart of a method of treatment, according to some embodiments of the invention.

FIG. 1A is a flow chart of a method of treatment, according to some embodiments of the invention.

At 101, in some embodiments, tissue for treatment is selected. For example, based on a diagnosis e.g. step 100 FIG. 1B.

Figure 1B:
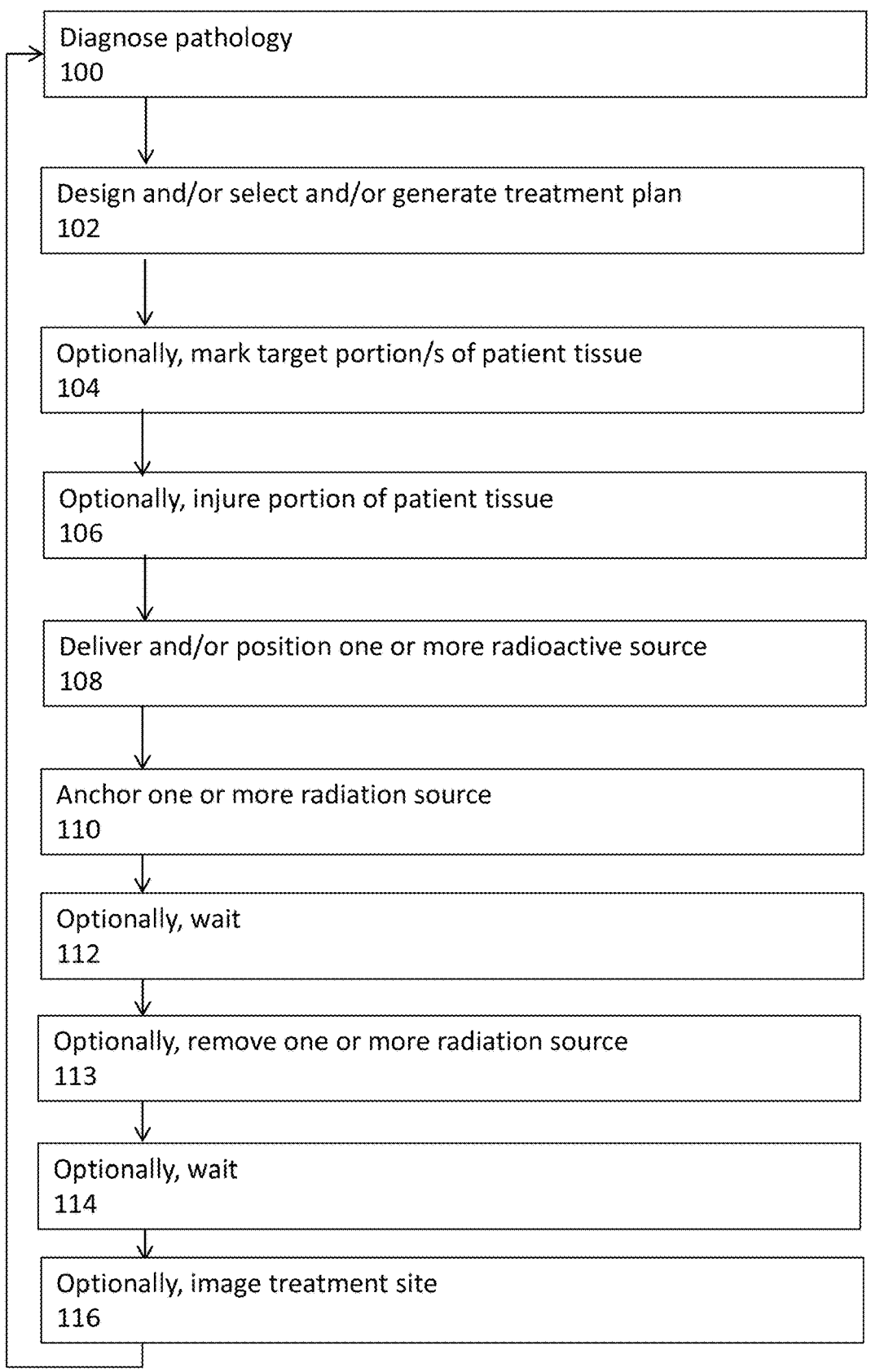
FIG. 1B is a flow chart of a method of treatment according to some embodiments of the invention.

At 103, in some embodiments, treatment is selected, for example, a treatment plan is selected and/or designed, for example, based on the diagnosis, e.g. including one or more feature as described regarding step 102 FIG. 1B.

At 105, optionally, in some embodiments, one or more portion of patient tissue is injured. For example, by one or more of application of chemical irritation agent/s, mechanical interaction with the tissue, ablation of tissue. For example, using one or more technique as described in the section of this document entitled "Exemplary endothelial injury" and/or the section of this document entitled "Exemplary embodiments".

At, 107, in some embodiments, one or more radioactive source is positioned such that one or more target portion of patient tissue is irradiated with low level irradiation (e.g. ionizing radiation). For example, the source/s containing one or more type of isotope which emit one or more of alpha, beta, gamma radiation. Where one or more feature of the radiation is, for example, as described in one or more of the sections of this document entitled "Exemplary Source", "Exemplary radiation", "Exemplary embodiments".

It should be noted that the steps of injury and positioning of radioactive source/s may be in any order. For example, positioning of the source/s after injury and/or positioning of the source/s before injury and/or the positioning itself involving injury and/or alternating injury with source placements for multiple injuries and/or source placements.

In some embodiments, a plurality of radioactive sources are positioned sequentially, optionally with time duration/s elapsing between positioning of two or more sources. For example, in some embodiments, after a source has undergone a level of radiation reduction (e.g. associated with decay of radioisotopes), in some embodiments, an additional source or sources are positioned and/or replace the decayed source.

In some embodiments, a target portion of tissue overlaps with injured tissue. For example, in some embodiments, an entire injured region of tissue (e.g. injured portion of a vessel) is irradiated with desired levels of radiation.

In some embodiments, radiation type and/or energy and/or intensity and/or total radiation quantity is configured to generate cell hyperproliferation (e.g. neointimal hyperproliferation) and/or vascular negative remodeling (VNR), for example, of one or more portion of one or more lumen.

In some embodiments, one or more radioactive source is implanted internally (e.g. subcutaneously and/or within a natural orifice) within a patient for example, within and/or adjacent to a lumen to be treated e.g. according to one or more feature as described regarding step 106 FIG. 1B.

In some embodiments, source/s are delivered and/or positioned in and/or in proximity to a target region endovascularly e.g. using a catheter. Alternatively or additionally, in some embodiments, one or more source is delivered and/or positioned via a needle. In some embodiments, one or more source is delivered and/or positioned in an open surgery and/or laparoscopic procedure.

Alternatively or additionally, in some embodiments, one or more radioactive source (e.g. emitting ionizing radiation) is positioned outside the patient e.g. a linear accelerator, e.g. stereotactic surgery where the linear accelerator is configured to expose target tissue to low level radiation e.g. including one or more feature as described and/or illustrated regarding the section of this document entitled "Exemplary radiation levels".

In some embodiments, positioning of source/s with respect to a pathology is according to the treatment plan and, in some embodiments, depends on the type of pathology.

In some embodiments, methods and/or devices e.g. as described within this document are used for treatment of one or more of:

Aortic aneurysms: Saccular aneurysms, Fusiform aneurysms, Pseudoaneurysms where each aneurysm type could be presented at exemplary locations including one or more of: proximal descending thoracic to proximal abdominal aorta, proximal descending thoracic to infrarenal, abdominal aorta, distal descending thoracic and abdominal aorta, abdominal aorta and including visceral vessel segments.

Intracranial aneurysms: for example, cerebral aneurysms, Berry (Saccular) aneurysms, Fusiform aneurysms, and Charcot-Bouchard aneurysms. For example located, anterior (carotid) circulation include the anterior communicating artery, the internal carotid artery (ICA) at the posterior communicating artery origin, and the MCA bifurcation, the ICA bifurcation and the pericallosal/callosomarginal artery bifurcation. Moreover they may arise on the posterior (vertebrobasilar) circulation. For example, at the basilar artery bifurcation, origin of the posterior inferior cerebellar artery (PICA).

The vertebrobasilar system, common carotid artery (CCA).

The vertebral artery (VA). superior cerebellar artery, anterior inferior cerebellar artery.

Venus aneurysms: in the lower extremities, the upper extremity, jugular vein. head and neck, abdominal veins, thoracic veins.

Chronic Venous insufficiency (CVI) in the lower extremities.

Heart valve insufficiency: aortic valve, tricuspid valve, mitral valve, pulmonary valve.

Para-valvular leakage: in the area of—aortic valve, tricuspid valve, mitral valve, pulmonary valve.

Vascular Anomaly Vascular Malformations: Arteriovenous Malformations (AVMs) and Arteriovenous Fistulas (AVFs), and/or Low Flow Malformations, which comprise of Venous Malformations (VMs), Capillary Malformations (CMs), and Lymphatic Malformations (LMs). For example located in cereberal, brain, spinal, heart, thoracic, extremities, renal, hepatic, abdominal.

Hemangiomas: Ophthalmic, Hepatic and Cardiac Hemangiomas.

FIG. 1B is a flow chart of a method of treatment according to some embodiments of the invention.

At 100, in some embodiments, a pathology is diagnosed. In some embodiments, diagnosis includes imaging of one or more affected site. Where imaging for example includes one or more of CT, MRI, ultrasound (e.g. intravascular ultrasound), nuclear imaging (e.g. SPECT and/or PET e.g. perfusion studies), eco-Doppler, angiography, echocardiogram, electroencephalogram. In some embodiments, one or more medical practitioner diagnoses one or more pathology by viewing collected image/s. Alternatively or additionally, a physician diagnoses one or more pathology using other diagnostic techniques e.g. medical history, blood pressure measurement/s (e.g. ankle-brachial index measurement), heart measurement statistic/s.

Alternatively or additionally, automatic diagnosis is performed using imaging data (and/or other patient data e.g. medical history, blood pressure measurement/s), for example, by a processor receiving the data. For example, where a processor, in some embodiments, performs automatic diagnosis (and/or generates at least a portion of a treatment plan) using one or more of artificial intelligence, neural networks, deep learning, machine learning, for example, of medical data (e.g. of one or more of type of imaging (e.g. CT, MRI, Ultrasound) and/or medical history.

At 102, in some embodiments, a treatment plan is designed by a physician (and/or other medical practitioner e.g. radiation oncology technician), for example, based on the diagnosis and/or other patient data e.g. patient anatomy. In some embodiments, one or more portion of a treatment plan is selected e.g. by the medical practitioner e.g. from a list of standard treatment plan features and/or from a list of automatically generated treatment plan feature/s. Where, for example, in some embodiments, the selection and/or display of the list is through one or more user interface. In some embodiments, one or more feature of a treatment plan, and/or option presented for user selection is generated automatically. For example, in some embodiments, a processor, for example, based on received imaging data and/or other patient data, generates a selection and/or recommendation for one or more portion of a treatment. Where the recommendation/s are presented to the medical practitioner/s e.g. through a user interface connected to the processor. For example, in some embodiments, planning software and/or feature/s of planning software, for radiation treatments, according to the art are used e.g. iPlan RT Brainlab, XiO, Monaco Elekta, Panther 3D Conformal Therapy System, Raystation Raysearch, Eclipse Varidan.

In some embodiments, a treatment plan includes whether injury is to be inflicted on patient tissue as part of the treatment. For example, in some embodiments (e.g. during diagnosis) the treatment site includes one or more innate and/or pre-existing injury and/or delivery and/or positioning of sources generates sufficient injury. In some embodiments, a treatment plan includes one or more of: a number of injury sites and in some embodiments, for one or more injury site, the location and/or extent and/or technique of tissue (e.g. vessel) injury. in some embodiments, different locations are injured using different techniques. Exemplary techniques are described, for example, in one or more of the sections of this document entitled "Exemplary endothelial injury", "Exemplary embodiments".

In some embodiments, a treatment plan includes one or more of; a number of radiation sources and, for one or more radiation sources, one or more of a radiation source size, shape, material, radiation type, a location, an intensity, a deployment type (e.g. deployment device) for the radiation source.

Optionally, at 104, in some embodiments, one or more portion of patient tissue is marked. For example, by positioning of one or more radiopaque marker and/or marker visible by another imaging method. In some embodiments marking is performed using more than one technique and/or at more than one point in a treatment.

Optionally, at 106, in some embodiments, one or more portion of patient tissue is injured e.g. chemically and/or mechanically, and/or by irradiation and/or by ablation e.g. according to the treatment plan e.g. including one or more feature as described regarding step 101 FIG. 1A.

In some embodiments, an injury is inflicted at and/or in proximity to target tissue. Where injury is, for example, to portion/s of a vessel endothelial layer and/or smooth muscle area (tunica intima and/or tunica media). In some embodiments, actual depth of injury varies, from treatment to treatment and/or within a single treatment area, for example, as different vessel types have different wall thicknesses and/or different layer thicknesses (e.g. veins generally have thinner smooth muscle layer than arteries).

Without necessarily wanting to be bound by theory it is though that injury of vessel tissue (e.g. endothelial tissue) initiates hyperproliferation under exposure of low level radiation, for example, the injury attracting migration of SMCs to the injury site/s where the radiation then encourages the migrated SMCs to hyperproliferate.

In some embodiments, injury is performed before positioning radioactive source/s (e.g. in a separate procedure and/or as a part of a single procedure). Alternatively or additionally, in some embodiments, injury is performed during (e.g. mechanical injury is sustained during positioning and/or anchoring of the source/s), and/or after positioning and/or anchoring of radioactive source/s (e.g. sclerosing agent/s applied afterwards).

In some embodiments, steps 104 and 106 are preformed concurrently e.g. where a marking material is applied concurrently to application of sclerosing material. For example, in some embodiments, fluid including sclerosing material and marking material is applied to a treatment site. For example, in some embodiments, sclerosing material and marking material are applied during a single procedure. In some embodiments, a material is applied which both marks and injures the site to which it is applied.

In some embodiments, at 108, one or more radiation source is delivered and/or positioned at a target region within the patient. Where, in some embodiments the radioactive source/s are positioned and/or have composition and/or radiation levels according to the treatment plan. In some embodiments, one or more source is a seed including encapsulated radioisotope material. In some embodiments one or more seed is coupled to an anchoring structure. Alternatively or additionally, in some embodiments, an anchoring structure includes radioisotope material.

In some embodiments, during and/or after treatment, anticoagulation medication is administered, for example, intravenously and/or orally and/or by implantation of one or more device e.g. which elutes anticoagulation medication. For example, to reduce risk of implantation-induced clot formation. In some embodiments, a radiation source includes and/or is connected to material including and/or eluting anticoagulation medication (and/or other medication).

In some embodiments steps 104 and 106 are performed concurrently where, in some embodiments, a seed and/or anchoring structure includes marking (e.g. radiopaque) material.

In some embodiments, at 110, source's are anchored in position e.g. within a vessel. For example, where a structure including source's is expanded into the vessel e.g. until a size of the structure anchors it in place within the vessel. In some embodiments, delivery and/or positioning is concurrent with anchoring.

In some embodiments, source includes technique/s known in the arts of Vascular Brachytherapy and/or Intravascular Brachytherapy and/or angioplasty and/or Vena cava filters, and/or endograft anchoring.

Alternatively or additionally to performing injury at step 106 e.g. before delivery and/or positioning of source/s, in some embodiments, tissue is injured after positioning of one or more source (e.g. where the injury/ies include one or more feature as described and/or illustrated regarding step 106 and/or FIGS. 2D-F).

In some embodiments, one or more of steps 104, 106, 108, 110 are performed during an operation. In an exemplary embodiment, the operation is a minimally invasive operation where, for example, target region/s are accessed through one or more blood vessel e.g. where a patient is catheterized through one or more femoral artery and/or radial artery.

At 112, optionally, in some embodiments, a time period is allowed to elapse. For example, sufficient time for a total desired radiation dose to be delivered to one or more portion of tissue.

At 113, optionally in some embodiments one or more radiation source is removed, for example, in some embodiments, treatment using acute radiation includes removal of the source after the total desired radiation dose and/or after a desired treatment time has elapsed. Where exemplary treatment times are illustrated, for example, in FIG. 4I. In some embodiments needle applied radiation source's are removed by removal of the needle. In some embodiments, source's located within a lumen e.g. using a catheter, are removed by withdrawal through a catheter (e.g. the same catheter that delivered the source or an additional catheter e.g. inserted a time period afterwards e.g. in another cathertization procedure).

At 114, optionally, in some embodiments a time period is allowed to elapse. For example, one week to one month or one month to six months or six months to 2 years.

At 116, optionally, in some embodiments, a postoperative follow-up is performed. For example, to verify the rate and end result that is given by the treatment. In some embodiments, follow up includes imaging performed by one or more method e.g. as described regarding step 100. In some embodiments, postoperative follow up is performed immediately after treatment. Additionally or alternatively, in some embodiments, postoperative follow up is performed at one or more time duration after treatment e.g. as described regarding step 112. In some embodiments, after the postoperative follow-up, at, 100, a new and/or previously diagnosed pathology is reevaluated and/or diagnosed.

FIGS. 2A-B are simplified schematic cross sections of a vessel 200 undergoing treatment, according to some embodiments of the invention. In some embodiments, the cross section of a vessel illustrated FIGS. 2A-B (and where cross section of vessel is otherwise not specified in this document) is a cross section of the vessel portion taken on the longitudinal axis of the vessel.

In some embodiments, vessel 200 includes a lumen 201 and vessel wall 203 (FIGS. 2A-B only illustrate one vessel wall). In some embodiments, FIG. 2A illustrates blood vessel 200 immediately after and/or shortly after placement of a radiation source 208. In some embodiments, FIG. 2B illustrates blood vessel 200 a time duration after placement of source 208.

In some embodiments, vessel 200 is a blood vessel, for example, a vein or artery. In some embodiments, vessel 200 is a lymphatic vessel.

In some embodiments, vessel wall 203 includes an tunica intima layer 202 (mainly composed of endothelial cells and also herein termed "endothelial layer") surrounded by a tunica media layer 204 (mainly composed of smooth muscle cells and also herein termed "smooth muscle layer") which is in turn surrounded by a tunica adventitia layer 230 (mainly composed of collagen also herein termed "collagen layer").

In some embodiments, injury/s 206 are inflicted on vessel wall 203. Where the injury, and/or injury technique, for example, includes one or more feature as described regarding step 101 FIG. 1A and/or step 106 FIG. 1B.

FIG. 2C is a simplified schematic cross section of a vessel 200 where the cross section is taken perpendicular to a long axis of the vessel.

FIGS. 2D-F are simplified schematics of the vessel cross sections illustrated in FIG. 2C illustrating injury, according to some embodiments of the invention.

FIGS. 2C-F, in some embodiments, illustrate cross section of the vessel and/or vessel portion taken on perpendicular to the longitudinal axis of the vessel.

In some embodiments, the injury is performed on a single portion of the blood vessel. In some embodiments, multiple injuries are inflicted on a plurality of different portions of the blood vessel e.g. as illustrated in FIG. 2F by injuries 206*f* and 207. In some embodiments, injury is to both endothelial layer 202 and to smooth muscle layer 204 (e.g. as illustrated in FIG. 2A, e.g. as illustrated by injury 206*e* FIG. 2E e.g. as illustrated by injury 206*f* FIG. 2F). Alternatively, in some embodiments, one or more injury (e.g. all injuries) injury are only to endothelial layer 202 e.g. as illustrated by injury 206*d*. In some embodiments, multiple injuries are, where different injuries, in some embodiments, are to different depths and/or on different portion/s of the vessel inflicted (e.g. as illustrated by injuries 206*f*, 207 FIG. 2F).

Returning now to FIGS. 2A-B. In some embodiments, one or more radioactive source 208 is positioned within the vessel e.g. within lumen 201 (e.g. including one or more feature as described by step 103 FIG. 1A and/or step 108 FIG. 1B).

In some embodiments, one or more source 208 is placed (e.g. by a device (e.g. expandable device) configured to anchor the source) within an axially central region (e.g. within an axially central 30-70%, or 40-60%, or lower or higher or intermediate ranges or percentages, of the lumen) of a portion of a length of a lumen e.g. including one or more feature as illustrated in FIGS. 2A-B, e.g. within an axially central 30-70%, or 40-60%, or lower or higher or intermediate ranges or percentages, of the lumen. Alternatively or additionally, in some embodiments, one or more seed is positioned in contact with and/or within the tunica intima and/or tunica media and/or tunica externa layers.

In some embodiments, source's are sized (and/or shaped) to prevent embolization of the lumen by the source and/or coagulation e.g. of blood flowing through the lumen. For example, in some embodiments, source axial dimension within a lumen are sized to be small with respect to axial dimension/s of the lumen in which they are placed e.g. less than 20%, or less than 10% or less than 5% or less than 1% or 1-20%, or 0.1-5%, or lower or higher or intermediate ranges or percentages of an maximum and/or average lumen dimension in a region of the lumen in which the source is positioned.

Alternatively or additionally, one or more source is configured to partially and/or fully obstruct a lumen. For example, where, in some embodiments, one or more source is large with respect to axial dimension/s of the lumen in which it is placed, for example, with 50-120%, or 50-100%, or 70-100%, or 70-95% or 80-90% of or lower or higher or intermediate ranges or percentages of an maximum and/or average lumen dimension in a region of the lumen in which the source is positioned.

In some embodiments, radiation level in a region of space between an inner boundary 210 and an outer boundary 212 is of a level to initiate and/or accelerate and/or increase hyperproliferation of SMCs and/or endothelial cells. Alternatively or additionally, in some embodiments, the radiation level between inner and outer boundaries 210, 212 is of a level to initiate and/or accelerate and/or increase negative remodeling of the lumen wall 203.

In some embodiments, FIG. 2B illustrates chronic irradiation. Where, in some embodiments, a region between source 208 and inner boundary 210 radiation is higher than the level between inner and outer boundaries 210, 212, for example at a level (initially and/or throughout treatment) which inhibits hyperproliferation and/or negative remodeling. Although acute radiation, in some embodiments, may also be associated with a region of space (e.g. adjacent to the source) where radiation levels are inhibitive to stenosis, in some embodiments, acute radiation includes one or more feature e.g. as illustrated and/or described regarding FIG. 3.

In some embodiments, the region of space between inner and outer boundary includes two regions, an inner region where radiation levels are suitable for hyperproliferation and/or negative remodeling and an outer region with lower radiation levels where the potential for hyperproliferation and/or negative remodeling is reduced and/or limited.

FIG. 2B illustrates hyperplasia regions 214, which, in some embodiments, occur within the region between inner and outer boundaries 210, 212.

Without necessarily wanting to be bound by theory, in some embodiments, e.g. as illustrated in FIG. 2B, hyperproliferation mainly occurs in vessel wall region/s 232 which have both undergone injury and are exposed to radiation levels between inner and outer boundaries 210, 212. Where, in some embodiments, hyperproliferation includes thickening of the tunica intima layer 202, with cells that migrate from tunica media layer 204. Without necessarily wanting to be bound by theory, it is theorized that injury 206 initiates and/or enhances the SMC migration to tunica intima layer 204, radiation then initiating and/or accelerating and/or enhancing multiplication of the SMCs (and/or endothelial cells) increasing the thickness of the vessel wall 203 which, in some embodiments causes stenosis of vessel 200.

In some embodiments, hyperproliferation is reduced outside the injury area, and, in some embodiments, is not present at 1-5 mm or 2-4 mm or about 3 mm outside the injured region.

Without necessarily wanting to be bound by theory, in some embodiments, e.g. as illustrated in FIG. 2B, negative remodeling mainly occurs in vessel wall region/s which have not undergone injury, but are between inner and outer boundaries 210, 212.

In some embodiments, negative remodeling occurs immediately outside and/or at a separation of 0.1-2 mm, or 0.5-1.5 mm or about 1 mm from the injury site.

In some embodiments, negative remodeling (and/or hyperproliferation) extends outside of region/s exposed to suitable radiation levels, e.g. the stenosis mechanism/s operating based on proximity to regions experiencing negative remodeling and/or hyperproliferation associated with received radiation.

In some embodiments, vessel stenosis associated with hyperproliferation is of a similar magnitude and/or has similar vessel closure potential (e.g. where the amount of stenosis differs by 0.1-20, or 0.1-10% or lower or higher or intermediate ranges or percentages) to that associated with negative remodeling.

In some embodiments, stenosis is via hyperproliferation within region/s exposed to radiation levels (e.g. as described within this document) and stenosis is via negative remodeling adjacent and outside the region/s experiencing hyperproliferation, the negative remodeling being thought to be due to (without wanting necessarily to be bound by theory) proximity to region/s experiencing hyperproliferation.

In some embodiments, injured and irradiated areas experience both hyperproliferation and negative remodeling.

In some embodiments, vessel closure by negative remodeling is slower than that by tissue growth, e.g. in some embodiments, vascular closure rate of the former is 40-60% of the latter. In some embodiments, region/s lacking injury and/or where injury is not sufficient to generate significant levels of hyperproliferation, stenosis and/or vessel closure, is due to negative remodeling e.g. within region/s exposed to exemplary level/s of radiation (e.g. as described in this document).

FIG. 3 is a simplified schematic simplified schematic cross section of a vessel 300 undergoing treatment, according to some embodiments of the invention.

In some embodiments, an inner wall 303 of the vessel before treatment is illustrated by a dotted line. Inner wall 322 of vessel 300 illustrates vessel 303 inner wall topography after treatment e.g. including positioning of a radiation source 308. In some embodiments, radiation levels are acute radiation application level/s (e.g. as described elsewhere in this document for example, within the section entitled "Exemplary radiation levels"). Where, in some embodiments, an inner region delineated by inner boundary 390 (e.g. adjacent to source 308) has radiation levels (rate and/or total dose) suitable for hyperproliferation and/or negative remodeling. Where, in some embodiments, an outer region between inner boundary 390 and outer boundary 392 has lower radiation (rate and/or total dose) which potentially causes limited hyperproliferation and/or negative remodeling. In some embodiments, correlating with radiation levels, higher stenosis e.g. as illustrated in FIG. 3 is exhibited inside the inner region e.g. than the region between boundaries 390, 392. In some embodiments, at stenosis occurs outside regions of suitable radiation, e.g. as illustrated in FIG. 3, for example, stenosis associated with tissue being effected by surrounding tissue.

Exemplary Radiation

Generally, intensity of radiation received by tissue from a radiation source reduces with distance from the source (reduction in intensity with distance) and with time (as the radioactive isotopes within the source decay) e.g. exponentially.

In some embodiments, "total dose" or "total radiation" refers to the total radiation for a treatment time span (e.g. for example in a time span of 1-12 months, or 2-10 months, or 2-8 months or 3-6 months, or about 4 months, or lower or higher or intermediate times or ranges) and/or the total radiation dose at therapeutic window dosage rates. In some embodiments, irradiation continues after the treatment time period e.g. at lower than therapeutic window radiation rates. In some embodiments, a percentage of the total dose received at therapeutic window radiation rates is 60-99%, or 80-95%, or lower or higher or intermediate percentages or ranges.

FIG. 4A illustrates simulated radiation rate levels with distance from a point radiation source at different times after source implantation, according to some embodiments of the invention. FIG. 4A illustrates momentary irradiation rate (mGy/hour) as a function of distance (mm) from a sealed source containing 125 Iodine isotopes, where an initial irradiation rate, (at t=0 days) is 60 mGy/hour.

It is to be understood that point sources, where the radiation source occupies no space are theoretical.

In some embodiments, a shape of radiation radiated by a source at exemplary levels is spherical, or cylindrical, or shell shaped. In some embodiments, a shape of radiation radiated by a source is asymmetrical.

FIGS. 4B-F illustrate simulated momentary radiation rate levels with distance from point sources, according to some embodiments of the invention.

FIGS. 4G-H illustrate simulation results of exemplary emitted cumulative radiation received by tissue, with distance from a source, for exemplary isotopes, according to some embodiments of the invention.

In some embodiments, FIGS. 4G-H illustrate simulation results for point source examples, for exemplary radiation isotopes. FIG. 4G illustrates 125I, 80 mGy/hour, 90 days point source radiation levels. FIG. 4H illustrates 169Yb, 80 mGy/hour, 90 days point source radiation levels.

Exemplary Radiation Application

FIGS. 5A-C are simplified schematic cross sections of treatment of a vessel 500 over time, according to some embodiments of the invention.

In some embodiments, amount of radiation emitted by a radiation source 508 changes sufficiently rapidly that different regions of vessel 500 experience different rates of stenosis (e.g. due to hyperproliferation and/or negative remodeling) at different times.

In some embodiments, FIGS. 5A-C show progressive stenosis of vessel 500 with time, where each figure shows a previous vessel inner wall position as a dotted line. Where, for example, FIG. 5A shows initial (e.g. before treatment) vessel inner walls 503 and vessel inner walls 522 after stenosis in response to radiation levels suitable for hyperproliferation and/or negative remodeling between an inner boundary 510 and an outer boundary 512.

FIG. 5B illustrates vessel 500 after a time period has elapsed, where radioactive isotopes within radiation source 508 have decayed and the area of radiation levels between boundaries 510, 512 is reduced in size and is closer to a location of source 580. Vessel 500 has further narrowed from vessel inner wall position 522 to vessel inner wall position 524.

FIG. 5C illustrates vessel 500 after another time period has elapsed, where the vessel exhibits yet further stenosis. In some embodiments, stenosis continues (e.g. as initiated and/or enhanced by radiation emitted from source 508) until vessel 500 is fully occluded.

FIG. 6A is a simplified schematic cross section of a radiation source 608 within a vessel 600, according to some embodiments of the invention. In some embodiments, radiation levels are selected such that inner boundary 610 is entirely and/or mainly contained with lumen 601 and the therapeutic region between inner and outer boundaries 610, 612 includes the lumen walls 603, for example, for at least a portion of the treatment time.

In some embodiments, a shape of source 608 is selected to affect a desired region of tissue. For example, in some embodiments, source 608 is elongate (e.g. including one or more feature as illustrated and/or described regarding source 1208 FIG. 12, 1308 FIG. 13, 1408 FIGS. 14A-C, 1508 FIG. 15). For example, in some embodiments, source 608 has a generally cylindrical shape. A potential benefit of an elongate source located where a long axis of the source is generally aligned with a topography of the lumen is that the source is able to irradiate a larger section of lumen (e.g. compared with a same volume source of spherical shape).

In some embodiments, source 608 is positioned and/or anchored such that a long axis of the source is parallel and/or with a small angle (e.g. 0-30°, or 0-10°, or 0-5°, or lower or higher or intermediate angles or ranges) to a long axis (e.g. central long axis) of the vessel and/or lumen in which the source is positioned and/or anchored.

FIGS. 6B-C are a simplified schematics section of radiation sources 608 positioned outside a vessel to be treated 600, according to some embodiments of the invention. In some embodiments, source 608 is positioned adjacent and/or in proximity to a target region (e.g. a vessel 600) where the source is positioned outside the vessel lumen 601. In some embodiments, e.g. as illustrated by FIG. 6C, source 608 is positioned within a vessel 650 (e.g. vessel lumen 651) adjacent and/or proximal to the target tissue, e.g. vessel 600. In some embodiments, for example, the source is delivered endovascularly to the vessel lumen and then advance through the lumen wall to a position outside the lumen. Where, boundary 612 in some embodiments, indicates an outer boundary of radiation configured to promote (e.g. stenosis through) hyperproliferation and/or negative remodeling.

Figure 9A:
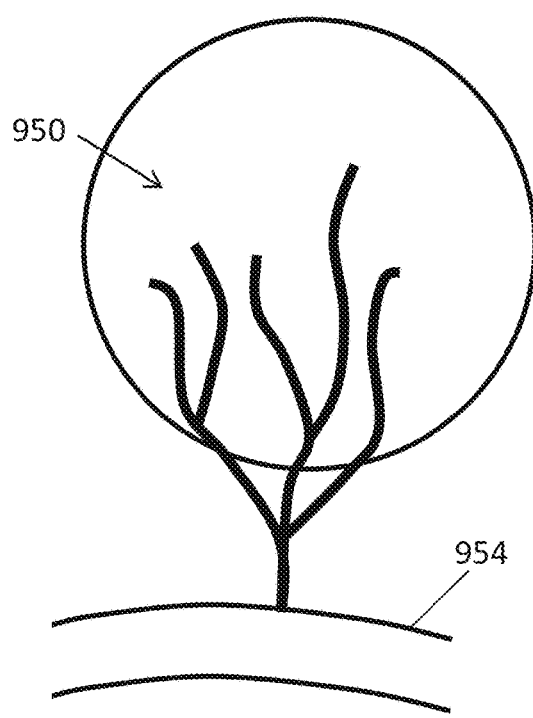
Figure 9B:
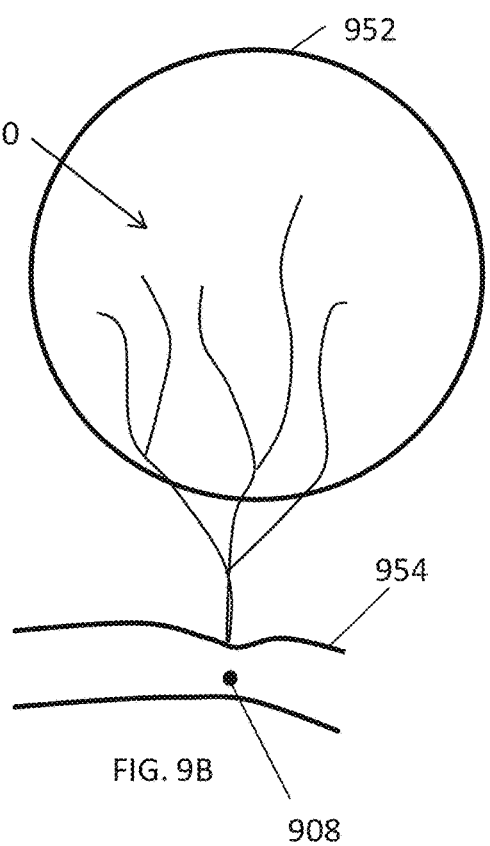
Figure 9C:
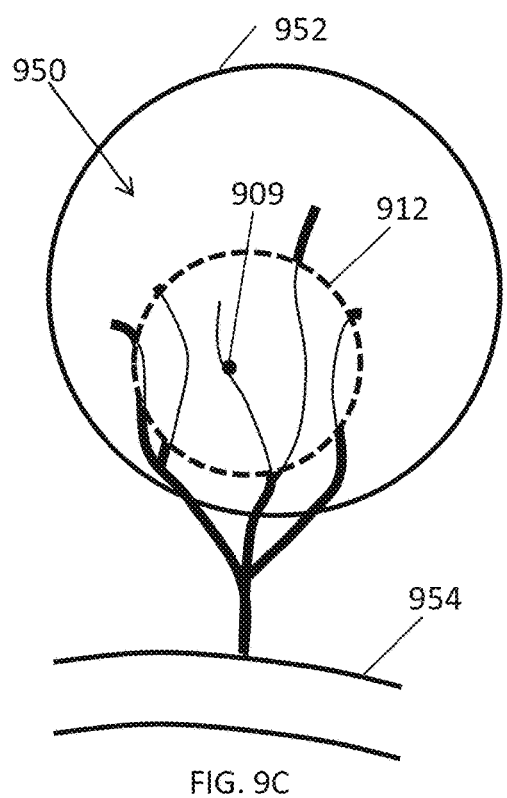
Figure 9D:
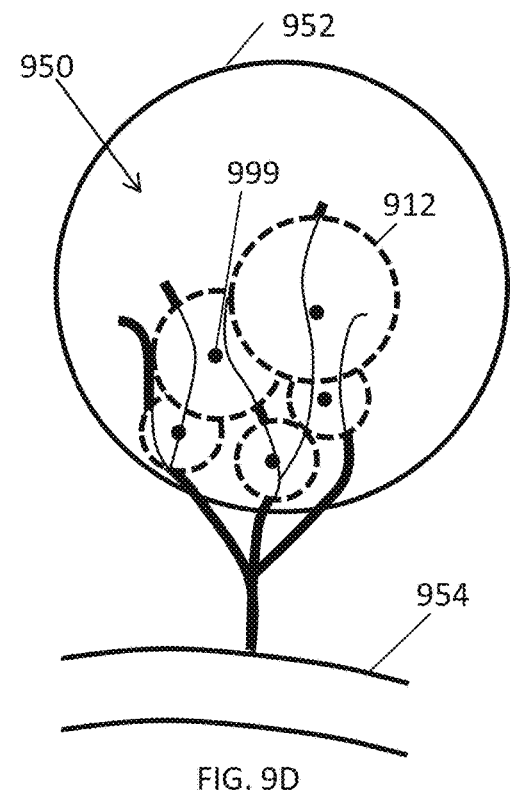

In some embodiments, a source 608 FIG. 6B positioned within a lumen 651 of a first vessel 650 is configured to treat (e.g. by irradiating suitable radiation levels e.g. as described elsewhere in this document) the first vessel and/or additional vessel/s 600 (another exemplary embodiments is illustrated and/or described regarding FIGS. 9B-D).

FIG. 7 is a simplified schematic cross section of a vessel being treated with a plurality of radiation sources 708, 709, according to some embodiments of the invention.

In some embodiments, a plurality of sources 708, 709 are used to treat, for example, a larger area of tissue. In some embodiments, radiation levels and/or separation between sources 708, 709 is selected so that an area 742 between the sources where, for example, neither source emits sufficient radiation e.g. to promote hyperproliferation and/or negative remodeling (e.g. outside boundaries 740), but where, in some embodiments, the combination of the overlapping radiations received by tissue e.g. in region 742 is sufficient to promote hyperproliferation and/or negative remodeling.

Exemplary Radiation Source Materials

Exemplary radiation sources emit alpha and/or beta and/or gamma radiations.

Exemplary radiation emitting isotopes ("isotopes") include 135Iodine gamma radiating isotope, 192Irridium gamma emitting isotope and 32Phosphorus beta emitting isotope and combinations thereof.

Additional exemplary isotopes include any isotope known in the art, for example, used in radiological and/or oncological and/or neurosurgical and/or nuclear medicine arts. Exemplary isotopes include, for example: 198gold, 125iodine, 137cesium, 55ocobalt, 55cobalt, 56cobalt, 57cobalt, 57magnesium, 55iron, 32phosphorus, 90strontium, 81rubidium, 2O6bismuth, 67gallium, 77bromine, 129cesium, 73selenium, 72selenium, 72arsenic, 1O3palladium, 2O3lead, 111ilindium, 52iron, 167thulium, 57nickel, 62Zinc, 63copper, 201thallium and 123iodine, and combinations thereof.

In some embodiments, a radiation source or seed as described in this document, contains one or more isotope e.g. as listed above.

Exemplary Radiation Levels

In some embodiments, overall cumulative (total dosage) of radiation is between 10 to 35 Gy. Exemplary radiation includes total radiation of 0.1-120 Gy, or 0.5-80 Gy, 1-60 Gy, or 1-45 Gy, or 2-40 Gy, or 2-36 Gy, applied at 1-500 mGy/hour, or at 100-500 mGy/hour, or 100-300 mGy/hour or lower or higher or intermediate ranges and values for total dosage and/or rate. Exemplary radiation includes and/or total radiation of 0.1-20 Gy, or 0.1-15 Gy, or 1-15 Gy, or 1-13 Gy at 500-1000 mGy/hour, or 500-1500 mHy/hour, or 300-1500 mGy/hour, or 300-2000 mGy/hour, or lower or higher or intermediate ranges and values for total dosage and/or rate.

In some embodiments, a target region of tissue is exposed to acute irradiation and/or chronic irradiation.

In some embodiments, acute irradiation is 0.1-40 Gy, or 0.1-13 Gy, at an irradiation rate of over 500 mGy/hour, for example, 500-1500 mGy/hour and/or 500-1000 mGy/hour, or lower or higher or intermediate ranges or values.

In some embodiments chronic irradiation is 0.1-120 Gy or 0.1-40 Gy, or 1-40 Gy, at an irradiation rate of between 5 m-500 mGy/hour, or 25-500 mGy/hour, or 50-500 mGy/hour, or 50-200 mGy/hour, or lower or higher or intermediate ranges or values.

FIG. 4I is a table showing exemplary radiation rates and total radiation doses, according to some embodiments of the invention. Where illustrated radiation values are levels of radiation that tissue is exposed to.

Exemplary radiation rates and radiation doses are marked with the time in hours of exposure (or seconds—marked "secs") required to achieve the total dose with the given radiation rate. Regions of the table where rates and/or total doses are unsuitable, for example, too low or too high (e.g. for hyperproliferation and/or negative remodeling e.g. for treatment/s as described in this document) are marked with "x". Regions of the table where time of exposure, in some embodiments, is longer than treatment according to some embodiments of the invention are marked with "-".

It should be noted that the values that are presented in FIG. 4I are average hourly values, and that the actual radiation intensity reduces with time and distance.

FIG. 4I illustrates radiation rates and doses for both chronic and acute radiation treatment, according to some embodiments. Without necessarily wanting to be bound by theory, the table illustrates, in some embodiments, that:

hyperproliferation and/or negative remodeling is expected at total dosage 2-40 Gy at radiation rates of 1-400 mGy/hour. In some embodiments, hyperproliferation and/or negative remodeling is expected at total dosage 2-80 Gy at radiation rates of 1-400 mGy/hour.

And/or hyperproliferation and/or negative remodeling is expected at total dosage 2-13 Gy at radiation rates of 500-1000 mGy/hour. In some embodiments, accurate irradiation promotes hyperproliferation and/or negative remodeling at rates above 1000 mGy/hour.

And/or low radiation rates with low total dosage (below 400 mGy/hour and below 1 Gy total) are not expected to generate sufficient hyperproliferation and/or negative remodeling e.g. for treatment/s as described in this document.

And/or high radiation rates with high total dosage (above 500 mGy/hour and above 14 Gy total) are not expected to generate sufficient hyperproliferation and/or negative remodeling e.g. for treatment/s as described in this document.

In some embodiments, lower dose rate (e.g. <10 mGy/hour or <1 mGy/hour, or <0.1 mGy/hour) for cumulative doses of over 40 Gy elicit hyperproliferation and/or negative remodeling.

FIG. 4J is a table showing potential for hyperproliferative vascular growth and/or negative remodeling potential with respect to total radiation dose and irradiation rates, according to some embodiments of the invention. Where illustrated radiation values are levels of radiation that tissue is exposed to.

In some embodiments, the radiation rate illustrated by FIG. 4J refers to an average radiation rate (e.g. depending of half-life of particular isotopes used). In some embodiments FIG. 4J illustrates average radiation rates for 32P.

FIG. 4J illustrates potential for vascular closure by hyperproliferation and/or negative remodeling as between 0 and 1 in arbitrary units.

FIG. 4K is a graphical representation of the table of FIG. 4J, according to some embodiments of the invention.

In some embodiments, FIGS. 4J-K illustrate ranges of vascular closure rates, as a function of average dose rates. Where average dose rates are illustrated for some embodiments where the radioisotope used is 32P and where, in some embodiments, boundaries of potential vascular closure (arbitrary unit >0) and little or no potential for vascular closure (arbitrary unit=0) and vascular closure are the same for all exemplary isotopes. In some embodiments, for highest potential vascular closure (arbitrary unit=1), radiation rates and/or total radiation doses for other exemplary isotopes are within 30%, or 25%, or 20% of those illustrated in FIGS. 4J-K and, for example, depend on the isotope half-life.

In some embodiments, vascular closure rate (e.g. by hyperproliferation and/or negative remodeling) is 0.01 mm-10 mm/month, or 0.1-7 mm/month, or 0.2-5 mm/month, or about 1 mm/month, or lower or higher or intermediate ranges or rates.

In some embodiments, exemplary radiation levels include any portion of the table of FIG. 4I and/or FIG. 4J where there is indicated potential for vascular closure e.g. in FIG. 4I portions of the table not marked "-" or "x" e.g. in FIG. 4J portions of the table with values of >0. In some embodiments, exemplary radiation is a range selected between any two such points within the table and/or including, values up to 10% or 20% beyond those indicated in the tables of FIG. 4I and FIG. 4J.

Acute Radiation Examples

TABLE 1

| Example # | Isotope type | Initial irradiation intensity rate at the source boundaries | Inner boundary distance from source and total radiation level | Outer boundary distance from source and total radiation level | Time for cumulative radiation to reach listed values |
|---|---|---|---|---|---|
| 1 | 125I | 13 Gy | 2 mm 8 Gy | 7 mm 2 Gy | 10 mins |
| 2 | 169Yb | 13 Gy | 9 mm 8 Gy | 34 mm 2 Gy | 10 mins |

For acute radiation examples 1 and 2, in some embodiments, within the region contained within the inner boundary, total radiation exposure between the source and the inner boundary of levels suitable for (e.g. neointimal) hyperproliferation and/or negative remodeling. In the region between the inner boundary and the outer boundary, there is lower potential for (e.g. neointimal) hyperproliferation and negative remodeling potential.

Chronic Radiation Examples

TABLE 2

| Example # | Isotope type | Initial irradiation intensity rate at the source boundaries | Inner boundary distance from source and total radiation level | Middle boundary distance from source and total radiation level | Outer boundary distance from source and total radiation level | Duration |
|---|---|---|---|---|---|---|
| 3 | 125I | 60 mGy/hour | 3 mm 35 Gy | 11 mm 8 Gy | 18 mm 2 Gy | 90 days |
| 4 | 169Yb | 60 mGy/hour | 15.5 mm 35 Gy | 42 mm 8 Gy | 66 mm 2 Gy | 90 days |

For chronic radiation examples 3 and 4, in some embodiments, within the region contained within the inner boundary, total radiation exposure between the source and the stenosis. In some embodiments, radiation values of the art which may cause stenosis are used to achieve gradual stenosis of vessel/s e.g. as described within this document.

TABLE 3

| Article | source used | Acute/chronic irradiation | Source geometry | prescribed edge effect dosage, or activity where dosage is not presented directly | est. actual edge effect related dosage (Gy) | trial duration (days) | avg. dosage rate at edges (Gy/hours) for acute or (mGy/hours) for chronic | Late Loss (%) |
|---|---|---|---|---|---|---|---|---|
| Geographic Miss A Cause of Treatment Failure in Radio-Oncology Applied to Intracoronary Radiation Therapy | 90Sr/90Y (β) | acute | rail (brachytherapy sources) | 16 Gy at 2 mm radius from the source axis | 9.6 | 180 | 5760 | 35 |
| | | | | 20 Gy at 2 mm radius from the source axis | 12 | 180 | 7200 | 35 |
| INTRACORONARY IRRADIATION: DOSE RESPONSE FOR THE PREVENTION OF RESTENOSIS IN SWINE[21] | 192Ir (γ) | acute | rail (brachytherapy sources) | 10 Gy | 10 | 30 | 554 | 24 |
| Effects of Endovascular Radiation From a β-Particle-Emitting Stent in a Porcine Coronary Restenosis Model | 32P (β) | chronic | stent | est. 15 Gy at 0.4 mm radius from stent for 1 [μCi] | 15 | 28 | 8.93 | 64 |
| "Edge Effect" of 32P Radioactive Stents Is Caused by the Combination of Chronic Stent Injury and Radioactive Dose Falloff[22] | 32P (β) | chronic | stent | est. 100 Gy at 1 mm radius from stent | 17 | 88 | 3.22 | 46 |
| | | | | — | — | 28 | — | 32 |
| Short- and Intermediate-Term Results of 32P Radioactive b-Emitting Stent Implantation in Patients With Coronary Artery Disease The Milan Dose-Response Study | 32P (β) | chronic | stent | est. 8-45 est. 45-70 est. 70-140 | est. 1.5-9 est. 9-18 est. 18-36 | 180 180 180 | — — — | 50 39 45 |
| Edge Restenosis After Implantation of High Activity 32P Radioactive - Emitting Stents | 32P (β) | chronic | stent | est. 59 est. 153 | 12 30 | 180 180 | — — | 37 31 | inner boundary is of levels too high for potential hyperproliferation and/or negative remodeling at time duration less than 45 days and at level suitable for (e.g. neointimal) hyperproliferation and/or negative remodeling. In the region between the inner boundary and the middle boundary, radiation levels are suitable for (e.g. neointimal) hyperproliferation and negative remodeling potential. In the region between the middle boundary and the outer boundary, radiation levels are suitable for limited (e.g. neointimal) hyperproliferation and negative remodeling potential.

In some embodiments, exemplary radiation level/s are found in literature (e.g. according to Table 3 below and/or one or more of the "Additional articles" described hereinbelow), which indicate value/s where radiation may cause Additional Articles Intracoronary Irradiation: Dose Response for the Prevention of Restenosis in Swine[21]

This article features a dose response dependent restenosis effect in swine, after a percutaneous transluminal coronary angioplasty involving Ir192 source. On histopathological analysis after 30 days, the 20 animals who received 20 Gy and 15 Gy shown a neointimal area decrease of 71.4% and 58.3%.

However, the 10 animals that were exposed to 10 Gy shown a neointimal area increase of 123%.

"Edge Effect" of 32P Radioactive Stents[22]

This text features a use of half-radioactive stent (half of the stent was radioactive—"hot"—while the other half was cold)—32P source—transplanted the coronary arteries in 20 animals. The trial was conducted for 12 weeks.

Original post stent implementation lumen diameter avg. 2.8 mm

Areas exposed maximal radiation (~100-500 Gy) and no radiation shown reduction of lumen diameter to 2.4 mm Areas exposed to partial radiation—"mid-stent" (~10-30 Gy) shown a decrease in lumen diameter to 1.9 mm.

Hormesis Induces by Low Dose Ionizing Radiation in Rat Mesenchymal Stem Cells[23]

In this article, rat MSC's were exposed to 5 MV X-rays of 20, 50, 75 and 100 mGy with a dose rate of 100 mGy/min. The cells were analyzed 24 h after exposure.

All of the radiation shown increase in viable cell count, with highest results—from baseline of 5 to 11 (10^4 cells) at 75 mGy.

In addition, a rise of MAPK/ERK—cellular proliferation signaling pathway kinases—had risen from a baseline of 1 (arb. Units) to a peak of 4 6 h after irradiation, and 1-2.5 after 24 h—at 75 mGy.

Low Dose Ionizing Radiation Enhances Cell Proliferation at Normal Human Lung Fibroblasts[24]

This article features human lung fibroblast proliferation after exposure to 137Cs gamma radiation, from 0.015 Gy-2 Gy at a dose rate of 0.8 Gy/min. the cells were analyzed 24, 48 and 72 hours after irradiation.

Results show increase in cells number at 0.015-0.05 Gy (peak proliferation, from 1.5 baseline to 3.6(×10^4), and decrease for values greater than 1 Gy.

In addition, peak rise in MAPK, ERK2 and p38 proteins was found at 0.05 Gy.

"Candy Wrapper Effect"—Due to Neointimal Hyperplasia or Remodeling?[25]

In this article, 11 human patients were treated with implantation of 32P (1.5-4 µCi) Palmaz Schantz stents, and were diagnosed 6 months after procedures.

Significant restenosis area was found at the central stent articulation (20%) and at the edges (13%).

Mean Lumen Diameter decreased from 2.99 to 1.38 mm.

The estimated cumulative radioactive dose at a distance of 0.5 mm from the surface of a 3.0 mCi 32P stent is about 20 Gy and 0.125 Gy at 0.1 mm.

Beta—Particle Emitting Radioactive Stent Implantation—a Safety & Feasibility Study[26]

In this article, 26 patients were treated with 32P (14.3 days HL, 0.75-1.5 µCi), and diagnosed after 6 months.

MLD increased from 0.87 mm preprocedure to 2.84 mm postprocedure. MLD at follow-up was 1.85 mm.

Point to be taken—the article states no restenosis was found, but lumen area was decreased.

In addition, this is the only article where balloon injury is specifically avoided and edge effect was still appearing.

Short and Intermediate Term Results of 32p Radioactive Betta Emitting Events[27]

In this text, 82 human patients divided into 3 groups, and were treated with 32P—1.71 MeV, with HL time of 14.3 days—emitting stents with activity levels of 0.75-3 µCi, 3-6 µCi & 6-12 µCi.

The patients were diagnosed 6 months after procedure.

0.75 to 12 µCi delivered a total dose of 8 to 140 Gy over a 28 days period 0.5 mm from the stent surface.

After 6 month, Mean Lumen Diameter for group 1, 2, 3 results were 1.6, 1.9 & 1.74 mm compared to 3.17, 3.13 & 3.17 mm reference diameters.

In addition, lumen areas loss was ~2.7 mm^2 at near stent edges comparing to ~0.8 mm at the stent center.

Edge Stenosis and Geographical Miss Following Gamma Radiation Therapy[28]

This article seeks the relationship between catheter balloon related injury ("Geographical Miss") and edge restenosis.

100 patients were treated with gamma radiation 192Ir/placebo.

Prescribed dose was 15 Gy/18.5 Gy for 2 mm & 4 mm diameter vessels.

Follow up irradiated edge MLD—1.60 mm compared to 2.63 mm reference.

Follow up placebo edge MLD—1.89 mm compared to 2.66 mm reference.

Late Lumen Loss was 0.74 mm at GM+ group, comparing to 0.13 mm at GM− group.

Edge restenosis was found at 8 of the 80 irradiated stent edges and 4 of the 84 placebo.

Exemplary Internal Problems/Risks

Exemplary Radiation Sources

Exemplary Geometry

In some embodiments, a radiation source and/or seed geometry is elongate e.g. approximately cylindrical. For example, including one or more feature as illustrated and/or described regarding one or more of FIGS. 6A, 12, 13, 14A-C, 15, 17A-B.

In some embodiments, a seed shape is spherical, cylindrical, elliptic, cuboid. In an exemplary embodiment (e.g. as illustrated by FIGS. 12, 13, 14A-C, 15, 17A-B) a radiation source shape is cylindrical with two spheric ends.

In some embodiments, a radiation source is embedded in another material and/or structure, for example, a vessel and/or valve support structure (e.g. stent), a bio-degradable polymer, an adhesive, an amplatzer.

In some embodiments, a radiation source is sized and/or shaped for endovascular insertion and/or positioning. In some embodiments, a radiation source size and/or shape is selected for a treatment lumen.

Exemplary Source Intensities and Relative Intensities

In some embodiments, a radiation source and/or a plurality of radiation sources used for a single treatment includes 0.01-20 mCi, or 0.01-20 mCi, or 0.1-20 mCi, or 0.1-10 mCi or lower or higher or intermediate ranges or values. For example, for chronic radiation treatment/s.

In some embodiments, a radiation source and/or a plurality of radiation sources used for a single treatment includes or 0.01-100 µCi, 0.1-50 µCi, or 1-15 µCi, or lower or higher or intermediate ranges or values. For example, for acute radiation treatment/s.

In an exemplary embodiment, radioisotopes are uniformly distributed within a source (e.g. inner portion of a seed which is encapsulated by another material). For example, the uniform distribution meaning that radiation intensity at the source's outer boundaries is uniform.

In some embodiments, a geometrical shape of the radiation field (e.g. where the field shape is, in some embodiments, defined as the shape of one or more equal radiation level) emitted by a source is spherical, cylindrical or a complex and/or irregular shape.

In some embodiments, the shape of the radiation field is the same general shape as a shape of the source material e.g. when radioisotopes are distributed uniformly within the source. Alternatively, in some embodiments, the radiation field shape is different from the source shape and/or seed shape where, for example, radioisotopes are distributed non-uniformly within the source material and/or source.

In some embodiments, one or more source (e.g. seed, device, portion of a device) has irradiates at exemplary radiation levels, in all directions (e.g. uniformly). In some embodiments, one or more source (e.g. seed, device, portion of a device) irradiates in different directions to different extents e.g. where, in some embodiments, one or more portion of a source is shielded (e.g. with thicker encapsulation and/or different composition encapsulation, e.g. including an additional shielding layer).

Exemplary Source and/or Seed Structures and/or Materials

In some embodiments, one or more source is a seed including radiation source/s (isotopes), and solid or mixed material used to contain (e.g. encapsulate) the isotope.

In some embodiments, the encapsulation material is gold, titanium, stainless steel, nitinol, platinum or combinations thereof and/or any material known to the art of Brachytherapy and as a medically intended radiation source containment.

In some embodiments, the source including radioisotope is singly encapsulated in stainless steel. In some embodiments, the stainless steel encapsulation is then welded an anchoring structure (e.g. including one or more feature as illustrated and/or described regarding one or more of FIGS. 12, 13, 14A-C, 15, 17A-B).

In some embodiments, a seed includes a core of radioactive material encapsulated by an outer shell of non-radiative material. In some embodiments, a seed includes radioactive material located between two layers of non-radiative material e.g. where, in some embodiments, radiative material partially or fully covers a core of non-radiative material which is then encapsulated by non-radiative material.

In some embodiments, irradiative material is located non-centrally within in the seed, for example an encapsulating material thickness varying around the irradiative material core.

In some embodiments, seed encapsulation material includes degradable material. For example, including oxidized regenerated cellulose and/or other biodegradable materials. In some embodiments, radioisotopes are embedded within cellulose (e.g. oxidized regenerated cellulose) strands and/or coated onto the outer surfaces of the strands. In some embodiments, a biodegradable encapsulation material is designed to disintegrate after a treatment time duration, for example, the radioisotopes being released from the seed and, for example, diluted within and/or removed by the body.

In another embodiment, the isotope containing source includes radioisotopes mixed with and/or incorporated into one or more polymer known in the art of embolization, for example gelatin foam, synthetic polymers such as poly(vinyl alcohol). For example, bioresorbable microspheres e.g. composed of chitosan and/or poly(ethylene glycol) derivatives. For example, in situ gelling liquid embolics. For example, radiopaque embolics e.g. which trackable in vivo.

In one embodiment, one or more type of radioisotope is integrated within the polymer uniformly.

Exemplary Tissue Injury

Exemplary Tissue Injury Via Exemplary Sclerosing Agent/s

In traditional vascular therapy, sclerotherapy is known as the injection of an irritant into a vascular malformation to cause endothelial cell death followed by scarring and obliteration of the vessel. In some embodiments, sclerotherapy irritant/s are used to inflict less severe injuries than those inflicted in the art of sclerotherapy. For example, one or more of; a lower area and/or volume of tissue effected, a less pronounced irritation and/or injury of tissue. In some embodiments, sclerotherapy irritants are used at lower concentrations than used in the art of sclerotherapy e.g. 1-90%, or 5-90%, or 5-50%, or lower or higher or intermediate percentages of the concentration of sclerotherapy concentration/s.

In some embodiments, a kit includes one or more radiation source and a sclerosing agent supply (e.g. including one or more sclerosing agent e.g. as a fluid). Where, in some embodiments, the radiation source is provided coupled and/or as part of an anchoring device (e.g. according to one or more anchoring device embodiment as described in this document and/or illustrated in accompanying figures). In some embodiments, the sclerosing agent is provided at a therapeutic (e.g. as according to embodiments described in this document) concentration and/or quantity e.g. the kit includes a single use quantity of sclerosing agent.

For example, including one or more feature as described regarding step 103 FIG. 1A and/or step 106 FIG. 1B, in some embodiments, one or more sclerosing agent (e.g. as known in the art of sclerotherapy) is administered (e.g. percutaneously) to a treatment region. In some embodiments, the sclerosing agent/s are administered to a pathologic area being treated (e.g. an AVM nidus).

Exemplary sclerosing agent/s, in some embodiments, are diluted (e.g. to exemplary concentrations e.g. as detailed hereinbelow) using one or more of water, isotonic saline and/or other solvents used in the art of vascular therapy.

Exemplary Sclerosing Agents Include:

Biological product/s. For example, OK-432 (e.g. Picibanil®), a freeze-dried biologic product is prepared from the Su strain of *Streptococcus pyogenes* (Group A) by treatment with benzylpenicillin and heat. (OK-432) has shone to produce an inflammatory response similar to atherosclerosis by inducing ICAM-1 expression. In some embodiments, concentration of 0.1 to 20 KE/mL OK-432, or lower or higher or intermediate values or ranges of OK-432 is used.

Chemical irritant/s, for example, glycerin which is a chemical irritant that acts as a corrosive agent, injuring cells through a heavy metal cauterizing effect. In some embodiments, concentration of glycerine used is 0.1% to 75%, or lower or higher or intermediate percentages or ranges.

Alcohol/s, for example, ethanol. Generally, ethanol is used as a 95% or a 100% solution. Without necessarily wanting to be bound by theory, it is thought that ethanol chemically injuries the vascular endothelium by denaturing blood protein. In some embodiments, concentration of alcohol e.g. ethanol used is 0.1% to 100% or lower or higher or intermediate percentages or ranges. Potential benefits of using ethanol include that ethanol is highly potent and/or quickly diluted and/or inexpensive.

Detergent agent/s, for example, polidocanol, sodium tetradecyl sulfate (STS). Without necessarily wanting to be bound by theory, it is thought that detergent agents such as polidocanol and/or STS kill cells by disrupting and/or denaturing cell membrane e.g. dissipating the cytoplasm, e.g. leaving only the nucleus. In some embodiments, concentration of polidocanol used is 0.0005% to 5%, or lower or higher or intermediate percentages or ranges. In some embodiments, concentration of STS is 0.0001% to 3%, or lower or higher or intermediate percentages or ranges.

Hyperosmolar solution/s, for example, hypertonic saline (sodium chloride 23.4%). Without necessarily wanting to be bound by theory, it is thought that hyperosmolar solutions are nonspecific in cellular destruction affecting endothelial cells as well as red blood cells through dehydration. In some embodiments, concentration of sodium chloride is 0.1% to 25%, or lower or higher or intermediate percentages or ranges.

Angiography contrast agent/s, for example, ionic contrast agent/s. Where exemplary angiographys contrast agents include diatrizoate, metrizoate, iothalamate, ioxaglate, iobytridol and combinations thereof. Without necessarily wanting to be bound by theory, one of the properties of a contrast media is an increase in endothelial permeability, which grants the contrast agent hypertonic attributes e.g. potentially causing nonspecific in cellular destruction affecting endothelial cells as well as red blood cells through dehydration.

In some embodiments, concentration of diatrizoate is 0.1-1500 mg/ml, or lower or higher or intermediate concentrations or ranges. In some embodiments, concentration of metrizoate is: 0.1-2000 mg/ml, or lower or higher or intermediate concentrations or ranges. In some embodiments, concentration of iothalamate is 0.1-1700 mg/ml, or lower or higher or intermediate concentrations or ranges. In some embodiments, concentration of ioxaglate is 0.1-1800 mg/ml, or lower or higher or intermediate concentrations or ranges. In some embodiments, concentration of iobytridol is 100-500 mg iodine/ml, or 200-350 mg iodine/ml or about 300 mg iodine/ml, or lower or higher or intermediate concentrations or ranges.

Exemplary Tissue Injury Via Initial Irradiation

In some embodiments (e.g. alternatively or additionally to other injury techniques described in this document) endothelial injury is via an initial high dose of irradiation. In some embodiments, vessel tissue is exposed to an acute administration of a high dose ionic irradiation. For example, In some embodiments tissue is exposed to a total of 14-200 Gy, at rates of over 500 mGy/hour.

In some embodiments, initial radiation e.g. of a portion of a vessel endothelial layer microscopically injures and/or irritates the layer.

Without necessarily wanting to be bound by theory, it is thought that the initial high dose irradiation disrupts the endothelial integrity, meaning that a later administration of low level and/or low dose ionic irradiation promote SMC migration and hyperproliferation.

In some embodiments initial injury and/or irritation is achieved by positioning a seed including one or more low duration half-life isotope at the treatment site. In some embodiments the seed includes both low duration half-life isotope/s e.g. configured to cause an initial injury and higher duration half-life isotope/s e.g. configured to provide low level irradiation e.g. to promote hyperproliferation and/or negative remodeling. In some embodiments the low duration half-life isotope/s are configured to irradiate target tissue at injurious and/or irritating levels for an initial 1 minute to 1 hour after implantation or 1 hour-10 hours after implantation or 1 hour-24 hours after implantation, or lower or higher or intermediate ranges or time durations.

In some embodiments, a seed includes a single radioisotope distributed within the seed and/or in an amount configured to initially irradiate the tissue at a high enough level to cause irritation and/or injury and, for example, after a time duration, to irradiate the tissue at lower levels selected to promote hyperproliferation and/or negative remodeling.

Alternatively or additionally, In some embodiments a linear accelerator is used to administer a radiation intensity field at a target tissue area where the radiation intensity field and/or duration of exposure and/or target tissue area is selected (e.g. according to a treatment plan) e.g. to injure and/or irritate the tissue.

Alternatively or additionally, In some embodiments stereotactic surgery, is used to administer a radiation intensity field at a target tissue area where the radiation intensity field and/or duration of exposure and/or target tissue area is selected (e.g. according to a treatment plan) e.g. to injure and/or irritate the tissue.

In some embodiments, initial radiation as an injury mechanism, followed by low level radiation, includes one or more feature of radiation levels as described in reference 17.

Exemplary Mechanical Methods for Tissue Injury

In some embodiments, (e.g. alternatively or additionally to other injury techniques described in this document) tissue (e.g. endothelial tissue e.g. of one or more portion of a vessel) is injured and/or irritated mechanically.

In some embodiments injury is performed via balloon angioplasty, where, for example, a vessel portion is distended (e.g. over-distention) by inflation of a balloon positioned within the vessel. For example, by inflation of the balloon to a size (e.g. central balloon region diameter) which is 1.01:1 to 2:1, or 1.05:1 to 1.5:1, or lower or higher or intermediate ratios or ranges, of the original vascular size (e.g. diameter). Without necessarily wanting to be bound by theory, it is thought that the stretching of the blood vessel results in mechanical injuries to the endothelial layer, e.g. which promote SMC migration and proliferation e.g. that, in some embodiments, is promoted by exposure to low radiation. In some embodiments, the balloon catheter is extracted after the procedure. In some embodiments the balloon is an angioplasty balloon delivered via catheter to the treatment area of the desired injury.

Alternatively or additionally, In some embodiments mechanical injury is via stereotactic surgery.

Alternatively or additionally, In some embodiments mechanical injury is via movement of a stent positioned within the vessel to be treated e.g. where friction irritates and/or injures tissue e.g. endothelial tissue. In some embodiments, the stent is moved linearly and/or twisted e.g. by manipulation of a guidewire to which the stent is attached.

Alternatively or additionally, In some embodiments mechanical injury is via movement of a guide wire which is, In some embodiments, positioned at a treatment area. In some embodiments, the guidewire is moved (e.g. laterally and/or by twisting) such that portion/s of the guidewire (e.g. the guidewire tip) contact and/or press against the vessel endothelial layer e.g. during the motion. Resulting frictional forces, in some embodiments induce endothelial injury and/or irritation.

Exemplary Tissue Injury Via Ablation

In some embodiments an ablation device is delivered to a target region (e.g. by a catheter). In some embodiments the ablation device includes portion/s (e.g. a tip) configured to heat and/or cool tissue in proximity and/or in contact with the portion/s. Without necessarily wanting to be bound by theory it is thought that high or low temperatures inflicted on tissue (e.g. endothelial tissue) result in cellular damage by protein denaturation and/or destruction.

Exemplary Ablation Techniques Include:

Radiofrequency ablation (RFA) where, for example, heat is generated e.g. at a catheter tip, e.g. by electrical resistance to medium or high frequency alternating current.

Microwave ablation where, for example, electromagnetic waves (e.g. 300 MHz to 300 GHz) are emitted, and locally transmitted to tissue e.g. via a catheter tip. In some embodiments affected tissue water molecules vibrate, producing heat.

Laser Ablation where, for example, a focal laser beam is emitted from a catheter (e.g. the ablation catheter tip) and for example, directed towards and/or at target tissue. In some embodiments the laser is high fluxed, e.g. evaporating and/or sublimating tissue. In some embodiments the laser is low fluxed, e.g. locally eliminating solid and/or liquid material by converting it into plasma. In an exemplary embodiment, CO2 laser, which, for example, ablates and/or cauterizes cells is used. Other exemplary lasers include argon, erbium, excimer, and Nd:YAG.

Ultrasound ablation, e.g. High Intensity Focused Ultrasound, and/or Magnetic Resonance guided Focused Ultrasound. In some embodiments low frequency ultrasound is used (0.25-2 MHz). In some embodiments high energy multiple intersecting beams which e.g. focus on a local target tissue area are used. In some embodiments ablation temperature, localized at target region/s are created by mechanical vibration due to acoustic wave absorption. In some embodiments ultrasound ablation is performed non-invasively. In some embodiments ultrasound ablation is performed endovascularly (IVUS).

Cryogenic Ablation, where, for example, low temperatures produce cold cellular damage. In some embodiments cooled fluid/s are circulated within a device which is contacted to and/or put in proximity with target tissue. In some embodiments the device includes cooled tip e.g. a hollow tip within which cooled fluid/s are circulated. Without necessarily wanting to be bound by theory it is thought that cell damage is sustained by mechanical damage associated with ice crystal formation e.g. which disrupts cellular membranes, and/or via metabolism dysfunction due to cold temperature. In some embodiments, indirect damage is produced by ischemia associated with blood coagulation, and/or apoptosis induction.

Balloon angioplasty, for example, hot or cold balloon angioplasty. For example, where one or more technique e.g. as described in this section is used where the device contacting tissue to be treated includes a cooled and/or heated balloon, for example a fluid filled balloon where the fluid transfers heat and/or to and/or from tissue to the device.

In some embodiments, mechanical injury and ablation injuries are performed with the same device and/or during the same procedure e.g. a cooled or heated angioplasty balloon both used to inflict temperature related and mechanical injury to vessel tissue (e.g. endothelial tissue)

Exemplary Applications

Exemplary Treatment of Aneurysm

FIG. 8A is a simplified schematic of a blood vessel 800 including an aneurysm 816.

FIGS. 8B-E are simplified schematics illustrating treatment of the aneurysm of FIG. 8A, according to some embodiments of the invention.

In some embodiments a structure 818 is positioned in proximity to aneurysm 816 (e.g. within a lumen 801 with which aneurysm 816 is associated). In some embodiments, structure 818 includes and/or is coupled to a radioactive source 808. In some embodiments, structure 818 is positioned such that source 808 is in proximity to aneurysm 816 e.g. at the aneurysm base.

In some embodiments, structure is an expandable structure, where, for example the structure is expanded into position within lumen 801. For example, in some embodiments, structure 818 is plastically expanded into position e.g. by balloon expansion. For example, In some embodiments structure 818 is a self-expanding structure which expands upon delivery and/or release at the treatment site e.g. elastically.

Figure 8D:
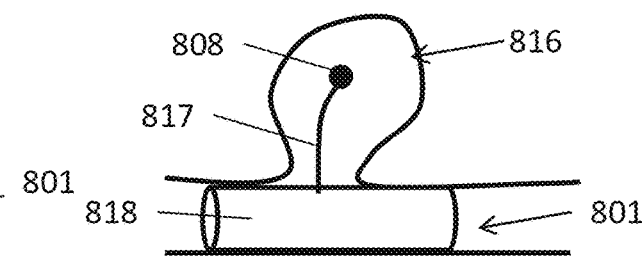

Referring now to FIG. 8D, In some embodiments structure 818 is configured to have a portion 817 which expands and/or moves into aneurysm. For example, In some embodiments source 808 is located on a protrusion 817 which, in some embodiments, is configured to unbend (e.g. elastically) into aneurysm 816 e.g. as structure is advanced within lumen 801.

Figure 8C:
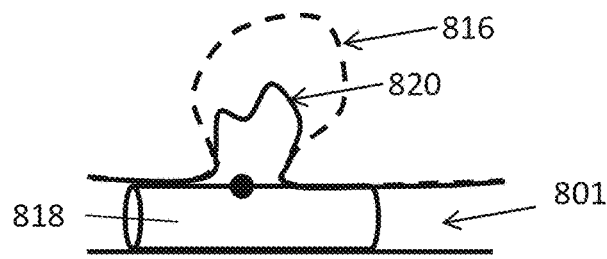
Figure 8E:
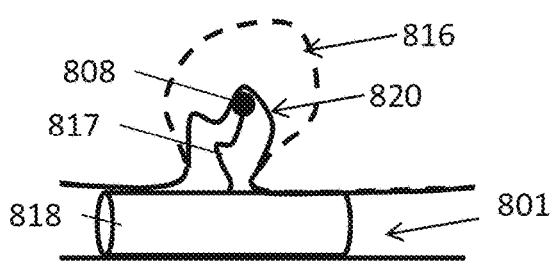

In some embodiments, (e.g. as described elsewhere within this document e.g. with respect to FIGS. 2A-C) an inner wall of aneurysm contracts, e.g. due to hyperproliferation and/or negative remodeling e.g. as illustrated in FIGS. 8C and 8E as the change in vessel inner wall topography from 816 to 820.

Exemplary Vascular Malformation Treatment

FIGS. 9A-D are simplified schematics illustrating treatment of a vascular malformation 950, according to some embodiments of the invention. In some embodiments, vascular malformation 950 is vascularization associated with a tumor 952. In some embodiments, vascular malformation 950 is an AVM. In some embodiments, positioning and/or number and/or radiation of one or more source (e.g. seed) is according to a treatment plan e.g. including one or more feature as described in FIG. 1B.

Referring to FIG. 9B, in some embodiments, one or more source 908 (e.g. seed) is positioned in proximity to vascular malformation 950. In some embodiments, one or more source 908 is positioned within a vessel 954 connected to vascular malformation 950, for example, within one or more artery feeding the vascular malformation (e.g. AVM nidus's feeding artery). In some embodiments, source 908, for example, through hyperproliferation and/or negative remodeling, effects stenosis and/or closure of at least part of the malformation 950 and/or vessel 954.

Referring to FIG. 9C, in some embodiments, alternatively or additionally, one or more source 909 is positioned within vascular malformation 950 for example, by anchoring the source to (e.g. inside) a vessel of vascular malformation. In some embodiments, one or more source 909 is positioned in a central region of the vascular malformation (e.g. arteriovenous malformation nidus e.g. tumor nidus) (e.g. within an axially central 30-70%, or 40-60%, or lower or higher or intermediate ranges or percentages, of the malformation). In some embodiments, source 909, for example, through hyperproliferation and/or negative remodeling, effects stenosis and/or closure of at least part of the malformation 950 and/or vessel 954.

Referring to FIG. 9D, in some embodiments, alternatively or additionally, a plurality of sources 999 (where in FIG. 9D identifier indicates one of the plurality of sources each source indicated by a black dot). Potentially using more than one source enables a larger portion of tissue to be treated. In some embodiments, sources have different sized and/or shaped radiation emissions (e.g. as illustrated in FIG. 9D).

Exemplary Valvular Treatment

FIG. 10 is a simplified schematic illustrating treatment of a valve, according to some embodiments of the invention In some embodiments, one or more source 1008 (e.g. seed) is positioned at the vicinity of a valve, for example, heart valve, for example venous valve (e.g. deep venous valve). In some embodiments, source/s 1008 are positioned at a base of the valve.

In some embodiment, radioisotopes are encapsulated within a stent tip, where the stent tip is positioned in the vicinity of a venous or heart valve. For example, the body of the stent connected to the tip, which in some embodiments is nonradioactive, anchoring the stent in position. In some embodiments, the stent provides structural support to the vessel, for example, preventing stenosis above a desired geometry.

In some embodiments, Chronic Venous insufficiency (CVI) and/or heart valve insufficiency and/or regurgitation e.g. associated with valve malfunction, is treated by placing one or more source (e.g. emitting radiation level/s as described and/or illustrated elsewhere in this document and/or associated figures) in a vicinity of an affected valve base, for example, in order to elicit an annuloplasty result by thickening of the valve base and reducing the distance between the cusps. In some embodiments, a closure final distance is determined by a supporting structure sufficiently robust to limit the stenosis to a desired annulus size.

Additional Exemplary Treatments

In some embodiments, treatment is of tumor/s (e.g. tumor associated vascular anomaly/anomalies e.g. tumor feeding blood vessel/s) and/or vascular anomaly/anomalies and/or vascular pathology. that relies upon or directly involves formation of abnormal blood vessels meaning. In some embodiments, treatment is of vasculogenesis and/or angiogenesis.

In some embodiments, treatment of angiogenesis includes implanting one or more source (e.g. emitting radiation level/s as described and/or illustrated elsewhere in this document and/or associated figures) at and/or near an angiogenesis source. For example, an angiogenesis within a tumor. The source, for example, exposing neovessels to a low dose and/or low dose rate radiation which results in occlusion of blood vessels (e.g. developed blood vessel/s, e.g. all developed blood vessels) for example, reducing and/or arresting tumor supply of nutrients.

In some embodiments, treatment of Vascular Anomaly Vascular Malformation (AVM) and/or Hemangiomas (e.g. Ophthalmic, Hepatic and Cardiac Hemangiomas) includes implanting one or more source (e.g. emitting radiation level/s as described and/or illustrated elsewhere in this document and/or associated figures) within the vascular anomaly or malformation and/or hemangioma volume, which may or may not follow an vascular injury or irritation. The portion of the pathology positioned within the therapeutic window will undergo vascular growth, remodeling or both and gradually occlude, thus obliterating the lesion, and/or treated portion of the lesion.

In some embodiments, treatment is of varicocele, where, for example, one or more radiation source is positioned to cause stenosis and/or constriction of vessels e.g. veins associated with varicocele.

Exemplary Anchoring Devices

In some embodiments, an anchoring device includes and/or is constructed partially or fully from material including radioactive material. In some embodiments, one or more radiation source (e.g. seed) is coupled to and/or attached to an anchoring device which, in some embodiments, does not include radioactive material.

In some embodiments, an anchoring device holds one or more radiation source within a vessel, for example, without structurally supporting the vessel.

FIG. 11 is a simplified schematic of an anchoring device 1118 including a connector 1160, according to some embodiments of the invention. In some embodiments, one or more source 1108 is attached to a vessel 1100 by one or more connector 1162. In some embodiments, connector 1162 includes one or more hook which is configured to enter and/or penetrate the vessel wall e.g. upon expansion of device 1118 and/or movement of device 118 (e.g. advancing and/or retraction of the device) within the vessel.

FIG. 12 is a simplified schematic of an anchoring device 1218, according to some embodiments of the invention. In some embodiments, device 1218 includes one or more source 1208.

In some embodiments, source 1208 is coupled to one or more expandable portion 1216, 1222. In some embodiments, source 1208 is elongate. In some embodiments, source 1208 is located at a central region of device 1218 (e.g. within an axially central 30-70%, or 40-60%, or lower or higher or intermediate ranges or percentages, of the device, for one or more device axis), for example, potentially enabling location of the source at a central region of a lumen to be treated. Where, for example, in some embodiments, expandable portion/s 1216, 1222 are configured (e.g. sized and/or shaped and/or biased e.g. elastically) to hold the source in a central region of a lumen (e.g. within an axially central 30-70%, or 40-60%, or lower or higher or intermediate ranges or percentages, of the lumen) for example, while a part of the expandable potion/s is in contact with the lumen wall.

In an exemplary embodiment, expandable portion/s are elastic, where, for example, the expandable portion/s are delivered in a contracted (e.g. crimped) configuration (e.g. through a catheter) to a treatment site. In some embodiments, device 1218 is anchored to a vessel by pushing the device out of the catheter and/or retracting the catheter. Expandable portion/s then, In some embodiments, elastically expanding e.g. to anchor the device to the vessel walls. In some embodiments, a device where a relaxed configuration of expandable portions 1216, 1222, has a larger dimension (e.g. diameter) than the vessel to be treated, elastic force applied by the expandable portions for example holding the device in position. Alternatively or additionally, in some embodiments, expandable portion/s are plastically expandable e.g. by balloon expansion.

In some embodiments, expandable portions are rounded, potentially preventing injury (e.g. and associated pathologies such as coagulation and/or deposition of plaque) to the vessel by the expandable portions. In some embodiments, one or more expandable portion (e.g. each expandable portion) describes a loop starting at source 1208 and returning to source 1208. In some embodiments, both expandable portions 1216, 1222 are formed by a single wire where the ends of the wire are connected at the source 1208.

Alternatively or additionally, in some embodiments, device 1318 includes one or more expandable portion which does not terminate at the source and/or which terminates extended away from a center of the device e.g. a wire which is configured to protrude into the lumen e.g. hooking the device onto the lumen wall e.g. including one or more feature illustrated and/or described regarding device 1908 FIGS. 19A-19C.

In some embodiments, source 1208 includes a hollow through which the wire passes e.g. twice e.g. in a "figure of eight" configuration.

In some embodiments, a shape of one or more of expandable portions 1216, 1222 is contained by a thin cuboid shape (e.g. where a thickness of the cuboid is 1-10% of a largest linear dimension of the device). In some embodiments, a shape of one or more of the expandable portions is contained within a plane e.g. as illustrated by the dashed planes illustrated on FIG. 12.

In some embodiments, shapes of different expandable portions are defined by cuboids and/or planes at different orientations e.g. as illustrated in FIG. 12 where the planes are orientated at about 90 degrees to each other. Potentially different angles of expandable portions strengthens anchoring the expanded device to the vessel.

In some embodiments, a device has a single expandable portion. In some embodiments, a device has two expandable portions e.g. as illustrated in FIG. 12. In some embodiments, a device has more than two expandable portions, for example, 3-20, or 3-10, or lower or higher or intermediate numbers or ranges. In some embodiments, a device has different sized and/or shaped expandable portions.

In some embodiments, expandable portions include one or more of Nitinol, Stainless Steel, Cobalt Chromium. In some embodiments, expandable portions are constructed from wire.

FIG. 13 is a simplified schematic of an anchoring device 1318, according to some embodiments of the invention. In some embodiments, FIG. 13 illustrates a device according to one or more features described and/or illustrated regarding FIG. 12 where device 1318 includes more than two expandable portions, for example, six expandable portions 1316. In some embodiments, expandable portions extending from one or both sides of a central region of the device are evenly dispersed at one or more axial point along a long axis of the device e.g. along the entire longitudinal axis of the device.

FIGS. 14A-C are simplified schematics of an anchoring device 1418, according to some embodiments of the invention. In some embodiments, anchoring device 1418 includes one or more expandable portion 1416, 1422. In some embodiments, one or more expandable portion is configured (e.g. shaped and/or sized and/or elastically biased) such that where a high proportion (e.g. 20-80% or 20-70%, or lower or higher or intermediate percentages of a length of the expandable portion) of one or more expandable portion, when the device is deployed, is in contact with the lumen walls and/or is located at an external portion (e.g. within a volume which is 20% or 10% of a volume of the lumen volume proximal to lumen walls).

Potentially high contact between the expandable portion/s and the lumen wall increases friction between the device and the wall, potentially reducing a risk of migration of the device.

Another potential benefit of a high proportion of the expandable portion/s being located proximal to lumen walls is lower influence of the deployed device on blood flow e.g. potentially reducing risk of coagulation and/or deposition (e.g. of plaque).

In some embodiments, the high proportion of the expandable portion configured to be in contact with or proximal to lumen walls (e.g. a low portion of the expandable portion/s length and/or volume within a central portion of the lumen), in some embodiments, is while the expandable portion/s are configured to hold one or more source 1408 in a central region of the lumen (e.g. within an axially central 30-70%, or 40-60%, or lower or higher or intermediate ranges or percentages, of the lumen).

FIG. 14C, in some embodiments, illustrates a top view of anchoring device 1418. In some embodiments, a shape of one or more expandable portion (e.g. when in a relaxed configuration e.g. as illustrated, in some embodiments, by FIGS. 14A-C) extends linearly in a small area 1470 (e.g. 1-30%, or 1-10% or lower or higher or intermediate areas) of the device and/or extendable portion/s maximal projected cross sectional area 1472 away from source 1408. Then, in some embodiments, the shape of the expandable portion/s delineates a loop at a constant distance (e.g. distance from the source varying by at most 1-30%, or 1-10%, or lower or higher or intermediate ranges or percentages) from the source 1408 and/or longitudinal center of the device.

FIG. 15 is a simplified schematic of an anchoring device 1518, according to some embodiments of the invention. In some embodiments, anchoring device 1518 has a tubular shape. In some embodiments, anchoring device 1518 is a woven structure e.g. woven from wire e.g. including one or more of Nitinol, Stainless Steel, Cobalt Chromium. Alternatively or additionally, in some embodiments, a tubular anchoring device is constructed by laser cutting, e.g. of a hollow tube. In some embodiments, a tubular structure is sufficiently compressible that the structure provides minimal support to the vessel in which it is located, for example, such that the structure does not prevent stenosis of the vessel. Alternatively, in some embodiments, structure 1518 is a stent which provides support to the vessel. For example, in the case of treatment of an aneurysm, structure 1518 provides support to the vessel e.g. while the aneurysm suffers stenosis.

In some embodiments, structure includes and/or is coupled to one or more source 1508 (e.g. seed) for example, by a protrusion 1517 (e.g. including one or more feature illustrated and/or described regarding element 817 FIGS. 8D-E). In some embodiments, protrusion 1517 is a wire extending from the weave of a woven structure 1524. In some embodiments, protrusion 1517 is configured to extend (e.g. elastically) into an aneurysm. In some embodiments, protrusion is thin e.g. 0.01 mm-1 mm thick, or lower or higher or intermediate thicknesses or ranges. Potentially, a thin protrusion is able to enter a narrow-necked aneurysm. In some embodiments, structure 1518 is an aneurysm graft (e.g. as known in the art) with an addition of one or more protrusion 1517 and/or source 1598.

FIG. 16A-B are simplified schematics of anchoring devices 1617, 1618, according to some embodiments of the invention. In some embodiments, structure/s 1617, 1618 are constructed by braiding or weaving. A potential benefit of a braided and/or woven structure is ability to crimp the devices to small dimensions (e.g. small cross sectional dimension) enabling their use in narrow lumen/s and/or in nerovascularture treatments/s. In some embodiments, one or more seed is attached to a braided structure.

FIG. 16C is a simplified schematic of an anchoring device 1619, according to some embodiments of the invention. In some embodiments, an anchoring device is an elongated element, for example, wire, ribbon 1619. In some embodiments, the elongated element is wrapped and/or coiled into position within a vessel e.g. using technique/s known in the art of endovascular coiling.

In some embodiments, radioisotopes are integrated within the structure (e.g. structure 1617, 1618, structure 1619) e.g. uniformly. In some embodiments, radioisotopes are integrated with the structure at different concentrations and/or where only portion/s of the structure are radioactive. For example, in some embodiments, radioisotopes are encapsulated within a tip of a structure (e.g. stent tip) where the body of the stent coupled to the tip anchors the tip in position.

FIG. 17A is a simplified schematic of an anchoring device 1718, according to some embodiments of the invention.

FIG. 17B is a simplified schematic plan view of the anchoring device 1718 of FIG. 17A, according to some embodiments of the invention.

In some embodiments, an anchoring device provides structure to a vessel being treated, for example, preventing the vessel from stenosis past a desired point. For example, in treatment of aneurism/s and/or valvular malfunction where, for example, thickening and/or stenosis of one region is desired while, in some embodiments, flow through the lumen is desired in other portion/s of the vessel. For example, as illustrated regarding FIGS. 8C and 8E where, in some embodiments, integrity of lumen 801 is maintained by structure 818.

In some embodiments, anchoring device 1718 includes a plurality of portions 1720 which are, in some embodiments, connected by attachment to another structure (e.g. a tubular structure e.g. constructed from polymer e.g. as known in the art of aortic graft device/s).

In some embodiments, one or more of portion/s 1720 include and/or are constructed from metal e.g. including one or more of Nitinol, Stainless Steel, Cobalt Chromium.

In some embodiments, anchoring device 1718 (which is e.g. in some embodiments, an expandable structure) includes a plurality of sources 1708.

A potential advantage of a plurality of sources is increased uniformity of irradiation to a target tissue region, potentially enabling treatment of larger lumens (e.g. aorta) and/or lumen areas. In some embodiments, a plurality of sources means that each source can have lower irradiation levels to provide treatment for a certain treatment area volume, potentially meaning that sources are selected to have lower area region/s (in total and/or per source) where radiation high enough to inhibit (and/or promote less) hyperproliferation and/or negative remodeling.

In some embodiments, anchoring device 1718 is used to treat larger blood vessel malformation/s (e.g. aeortic aneurysm's), e.g. to effect stenosis of the aneurysm where portion/s 1708 and/or a structure connecting the portions provides structure to the vessel e.g. preventing stenosis below a desired lumen geometry.

FIG. 18 is a simplified schematic of an anchoring device 1818, according to some embodiments of the invention. In some embodiments, one or more portion of device includes (e.g. is constructed from and/or is coated with and/or has source's imbedded within) radioactive material.

In some embodiments, anchoring device 1818 is configured to be anchored to a valve e.g. a base of a heart and/or venous valve.

In some embodiments, device 1818 includes one or more protrusion 1862. Where, in some embodiments, protrusion/s are configured to increase friction between the deployed device 1818 and lumen tissue e.g. by impaling and/or breaching lumen walls e.g. with a tip of the protrusion and/or increased friction between protrusion/s and the lumen wall. In some embodiments, device 1818 is an expandable device e.g. plastically and/or elastically (e.g. where the device expands by release of elastic compression).

FIGS. 19A-C are simplified schematic illustrating delivery of an anchoring device to a treatment area, according to some embodiments of the invention At FIG. 19A, in some embodiments, an expandable device 1908 is positioned within a lumen 1901 to be treated e.g. by positioning a guide 1940 (e.g. catheter) within the lumen where the expandable device is positioned within and/or advanced through the guide 1940.

At FIG. 19B, in some embodiments, expandable device 1908 is advanced from the guide and/or the guide is retracted from the expandable device. One or more portion of the device 1922 (e.g. expandable portion, e.g. as described with reference to embodiment/s described and/or illustration/s referred to in the section of this document entitled "Exemplary anchoring devices") expands and/or is expanded.

At FIG. 19C, in some embodiments, the device is fully external to the guide which is, in some embodiments, removed. In some embodiments, the device expands (and/or is expanded) within the lumen, for example until the device contacts and/or anchors to the lumen wall.

Exemplary Embodiments

Medium AVM Lesion—Twin Sources, 125 Iodine

FIG. 20 is a simplified schematic of treatment of a vascular malformation nidus by a plurality of sources, according to some embodiments of the invention.

In some embodiments, FIG. 20 does not illustrate the sources.

Sources Properties—

A cylindrical shape source (e.g. including one or more feature as illustrated by and/or described regarding source 1408 FIGS. 14A-C), dimension 0.8×3 mm.

Source plating—stainless steel.

Anchoring device—nitinol wire, peripheral intraluminal positioning (including one or more feature as illustrated by and/or described regarding device 1418 FIGS. 14A-C).

Isotope—125 Iodine, radiation intensity of 80 [mGy/hour] distributed uniformly at the time of implantation.

Treatment Stages:

Treatment planning—positioning of the two sources at nidus areas where the radiation fields are at the therapeutic window at the entire nidus volume—view FIG. 20. (nidus length—40 mm).

Percutaneous delivery of brachytherapy seed sources into an AVM nidus site.

Anchoring the sources at the chosen places within the nidus, according to the treatment planning strategy.

Nidus area is exposed to low dose rate radiation—see FIG. 4C for radiation intensity of each 125I source.

Percutaneous delivery of a sclerosing agent into the nidus area. Chosen sclerosing agent for this example is Ethanol at concentration of 3%.

Sclerosing agent elicits endothelial irritation, which is followed by a neointimal hyperprolific (vascular growth) response within the nidus. Negative remodeling occurs in areas where the sclerotic agent did not induce a sufficient injury for vascular growth.

Hyperproliferative and remodeling blood vessels are gradually narrowed, until complete occlusion.

Large AVM Lesion—Single Source, 169 Ytterbium

FIG. 21 is a simplified schematic of treatment of a vascular malformation, according to some embodiments of the invention.

Source Properties

A single source of cylindrical shape source (see FIGs. 14A-14C), 0.5×2 mm (In some embodiments, FIG. 21 does not illustrate the source).

Source plating—nitinol.

Anchoring device—nitinol wire, peripheral intraluminal positioning (see FIGs. 14A-14C).

Isotope—169 Ytterbium, radiation intensity of 80 [mGy/hour] distributed uniformly at the time of implantation.

Treatment Stages:

Treatment planning—positioning source at nidus center where the radiation fields are at the therapeutic window at the entire nidus volume—view simplified Illustration below. (nidus length—60 mm). In some embodiments, treatment involves irradiating the entire AVM model with therapeutic range radiation levels e.g. without injuring and/or while minimally injuring and/or radiating surrounding tissue.

Percutaneous delivery of brachytherapy seed source into an AVM nidus site center.

Anchoring the source at the center of the nidus.

Nidus area is exposed to low dose rate radiation—see FIG. 4D for radiation intensity of 169Yb source.

Percutaneous delivery of a sclerosing agent into the nidus area. Chosen sclerosing agent for this example is Chromated Glycerin at undiluted 50% concentration.

Sclerosing agent elicits endothelial irritation, which is followed by a neointimal hyperprolific (vascular growth) response within the nidus. Negative remodeling occurs in areas where the sclerotic agent did not induce a sufficient injury for vascular growth.

Hyperproliferative and remodeling blood vessels are gradually narrowed, until complete occlusion.

Exemplary Treatment of Aneurysm e.g. Cranial Aneurysm

FIG. 22 is a simplified schematic of treatment of an aneurysm, according to some embodiments of the invention.

In some embodiments a device 2208 for treatment of aneurysm includes a single 2222 element (e.g. expandable element) connected to a radiation source 2208 (e.g. seed). In some embodiments, This example features a specific strategy of closing a cranial aneurysm narrow opening, thus preventing blood flow into the aneurysm volume, promoting hemostasis and clotting which fill the Aneurysm volume and remove bleeding risk.

Exemplary Source Properties

A cylindrical shape source (see FIGs. 14A-14C), 0.5×2 mm.

Source plating—nitinol.

Anchoring device—nitinol wire, peripheral intraluminal positioning (see FIGs. 14A-14C).

Isotope—125 Iodine, radiation intensity of 80 [mGy/hour] distributed uniformly at the time of implantation.

Exemplary Treatment Stages:

Treatment planning—positioning source at a position within the aneurysm volume, where the therapeutic window comes in contact specifically with the opening and promoting its closure.

Percutaneous delivery of a brachytherapy seed source into a cranial aneurysm site.

Anchoring the source at the desired position within the aneurysm volume.

Aneurysm volume area is exposed to low dose rate radiation—see FIG. 4C for radiation intensity of 125I source.

Mechanical irritation of the endothelial layer at the opening of the aneurysm is performed by gently rotating the implantation wire, creating friction on the inner blood vessel layer.

The endothelial irritation is followed by a neointimal hyperprolific (vascular growth) response within the opening of the aneurysm, and that area alone.

Hyperproliferative opening are is gradually narrowed, until complete occlusion.

Exemplary Abdominal Aortic Aneurysm

FIG. 23 is a simplified schematic of a treatment using an irradiating supporting structure, according to some embodiments of the invention;

This example features a strategy of promoting contact between aortic graft and an abdominal aortic aneurysm section, where device/s and/or method/s (e.g. as described within this document) are used for promoting vascular growth and thickening of the aneurysm wall—which reduces rupture risks continuously, until tissue contact with graft structure. This example features a fusiform aneurism at the beginning if its pathogenesis, where the diameter of the aneurysm is 2 mm wider than the abdominal aorta. This application enables the use of a local irradiation elicited by an 125 Iodine source.

Exemplary Source Properties

Sources placed on aortic graft (see FIGs. 17A-17B), each source geometry is 0.3×1 mm.

Source plating—steel.

Anchoring device—an aortic graft which contains the device, which two optional anchoring devices—as used if FIG. 18.

Isotope—each source contains 125 Iodine, radiation intensity of 80 [mGy/hour] distributed uniformly at the time of implantation to create a cylindrical therapeutic volume.

Exemplary Treatment Stages:

Treatment planning—positioning source at a position within the aneurysm volume, where the therapeutic window comes in contact specifically with the aneurysm vascular walls.

Percutaneous delivery of a device and anchoring mechanisms.

Anchoring the source at the desired position proximal and distal to the aneurysm volume.

Aneurysm volume area is exposed to low dose rate radiation—see FIG. 4C for radiation intensity of 125I source.

The injury mechanism in this example is endogenic—an aneurysm wall undergoes a constant endothelial dysfunction, inflammation and SMC migration which transforms into neointimal hyperproliferation under the radiation therapeutic window.

A neointimal hyperprolific (vascular growth) response within the inner wall of the aneurysm begins to take place.

Hyperproliferative opening is gradually narrowed, until in contact (e.g. complete contact) with the graft that contains the radiation source/s.

Exemplary Aortic Valve Anuloplasty

FIG. 24A is a simplified schematic of an anchoring device, according to some embodiments of the invention.

FIG. 24B is a simplified schematic of treatment of a valve, according to some embodiments of the invention.

This example features a specific strategy of Re shaping a valve annulus, this is done in order to assist the valves leaflets to meet in a proper way, without the need to replace the any part of the patient's own valve.

Exemplary Source Properties

The radiative source is embedded within the struts of the distal anchor. This section is used for radiation emission, and for limiting the in-growth of the anulus due to the hyperfroliferative, low dose induced phenomena, which implies that it's relatively stiff and covered with a coat of polymer in order to serve this phenomena as well.

The proximal anchor which is the larger section, serves for anchoring to the blood vessel (aorta).

Between the 2 anchors there is a polymer which joins them.

Anchoring device—nitinol structure that is cut from a tube.

Isotope—125 Iodine, radiation intensity of 80 [mGy/hour] distributed uniformly at the time of implantation.

Exemplary Treatment Stages:

Treatment planning—positioning source at a position within the valves anulus, where the therapeutic window comes in contact specifically with the opening and promoting its closure.

Percutaneous delivery of a device into the aortic valve's site.

Anchoring the device at the desired position within the valves proximity.

Annulus volume area is exposed to low dose rate radiation—see FIG. 4C for radiation intensity of 125I source.

Mechanical irritation of the endothelial layer at the opening of the aneurysm is performed by gently rotating the implanted distal anchor, creating friction on the inner annulus layer.

The endothelial irritation is followed by a neointimal hyperprolific (vascular growth) response within the annulus, and that area alone.

Annulus is gradually narrowed, until it comes to contact with the distal (smaller & radiative) Anchor.

Exemplary Method

FIG. 25 is a flow chart of a method, according to some embodiments of the invention.

At 2500, in some embodiments, inspect anatomy and/or physiology of pathology e.g. using one or more feature as described regarding step 100 FIG. 1B.

At 2502, in some embodiments, design and/or select and/or generate a theoretical treatment plan e.g. using one or more feature as described regarding step 102 FIG. 1B.

At 2504, in some embodiments, design a therapeutic window volumetric geometry.

At 2506, in some embodiments, design a radiation field.

At 2508, in some embodiments, select radioactive source.

At 2510, in some embodiments, select coating material.

At 2512, in some embodiments, select isotope distribution strategy.

At 2514, in some embodiments, select initial source's activity (e.g. radiation emitted by stent including and/or coupled to radioactive material), after taking into account coating and shape factors.

At 2516, in some embodiments, perform design review.

In some embodiments, table 4 illustrates exemplary embodiments of the method of FIG. 15.

extended from the sheath, for a treatment time duration. In some embodiments, the radiation source is delivered endovascularly e.g. by catheter.

FIG. 29 is a flow chart of a method of an exemplary treatment, according to some embodiments of the invention. For example, of an acute radiation treatment plan design method e.g. for a gamma emitting device for treatment of aneurysm e.g. as illustrated, in some embodiments thereof by FIG. 28.

The present invention, in some embodiments thereof, relates to methods and/or devices for treating tumors and/or vascular disease and/or anomalies and/or pathologies using a radiation regime which includes low dose ionizing radiation. The radiation is administered using a source or sources from within the tumors' blood vessels. This is done in order to induce hyperplasia that will occlude or partially occlude the tumor's blood vessels.

The present invention, in some embodiments thereof, is directed to methods and devices for treating pathologies related to the existence of tumors—both malignant and benign, as well as vascular and/or valvular abnormalities—by eliciting cell hyperproliferation/hyperplasia with a radiation regime which includes low dose ionizing radiation by using radioactive compositions. These methods and devices entail the in vivo delivery of radioactive source or sources,

TABLE 4

| Step number, FIG. 25 | Example - Chronic device activity design - gamma emitting device | Example - Chronic device activity design - beta emitting device |
|---|---|---|
| 2500 | Brain Fusiform Aneurysm, 1 mm vessel diameter, 3 mm aneurysm diameter | Brain Fusiform Aneurysm, 1 mm vessel diameter, 3 mm aneurysm diameter |
| 2502 | using a stent with uniform source distribution | using a stent with uniform source distribution |
| 2504 | a 3 mm cylinder around an implanted stent, for 90 days | a 3 mm cylinder around an implanted stent, for 90 days |
| 2506 | cumulative irradiation will be 10-35 [Gy] at aneurysm wall throughout a 90 days period, and an initial 50 [Gy] at the surface of the implanted stent. | cumulative irradiation will be 10-35 [Gy] at aneurysm wall throughout a 180 days period, and an initial 100 [Gy] at the surface of the implanted stent. |
| 2508 | selected source is a gamma emitting I125, with a 59.4 days half life time. | selected source is a beta emitting 32P, with a 14 days half life time. |
| 2510 | selected material is Cobalt Chromium | selected material is Cobalt Chromium |
| 2512 | selected strategy is a unformal distribution. | selected strategy is a unformal distribution. |
| 2514 | Activity 1.5 mCi (gamma) | Activity - 8.7 µCi (beta) |

FIG. 26 is a flow chart of a method of an exemplary treatment, according to some embodiments of the invention. For example, of a chronic radiation treatment plan design method, e.g. for a gamma emitting device for aneurysm e.g. as illustrated, in some embodiments thereof by FIG. 22.

FIG. 27 is a flow chart of a method of an exemplary treatment, according to some embodiments of the invention. For example, of a chronic radiation treatment plan design method, e.g. for a beta emitting device for treatment of aneurysm e.g. as illustrated, in some embodiments thereof by FIG. 23.

FIG. 28 is a simplified schematic of acute treatment, according to some embodiments of the invention. In some embodiments, acute treatment includes delivery of an irradiation-sheathed radiation source (or sources) e.g. to prevent irradiation of tissue during delivery e.g. as known in the art of brachytherapy. In some embodiments, the source is which are delivered to one or more vascular sites in the tumor's blood supply vessels This will result in vascular occlusion/stenosis to at least partially occlude the affected blood vessels. The effect is found in the blood vessel that the radiative source is located, and (Possibly) in neighboring vessels that are influenced by the radiation regime. A delivery of continues controlled amount of radiation is performed to further block the tumor's blood vessels by exhibit growth of the vessels' Smooth Muscle Cell layers inwards, thus narrowing their lumen diameter.

Another application of the hyperproliferative effect is for valvular insufficiency. By thickening the tissue at venous or heart valves or at their base, the distance between their cusps reduces and normal valve physiological functionality is restored.

The hyperproliferative effects include but are not limited to the Tunica Intima/Media, but to the induction of hyperactivity in specific target cells such as malignant cells— which, combined with lack of resources as a result of the said blood vessels' obstruction, can exhaust their metabolism and cause desired cellular death.

This invention, in some embodiments thereof, applies to any tumor that relies upon or directly involves formation of abnormal blood vessels—meaning, tumor feeding blood vessels (either resulted via vasculogenesis or angiogenesis) and/or any type of Vascular Anomaly.

Angiogenesis, among its other modalities, is a result of a malignant tumor's metabolic resources' recruitment, as its growth and metabolic activity requires ever growing nutrients supply via blood stream. Thus, any tumor that reaches a certain size (usually 1-2 mm diameter) will secret vascular growth factors (mainly VEGF bFGF) that will induce vascular sprouting and creation of blood vessels from nearby existing arteries. Nowadays, a few cancer treatment protocols comprise of Angiogenesis based tumor therapy, which involve usage of chemical protein based angiogenesis inhibitors[1]. In other treatment modalities, radiation treatment/chemotherapy is used together with Angiostatic drugs, which tend to show conflicting results—as the inhibition of angiogenesis can potentiate the effects of radiotherapy[2].

Vascular Malformation is a blood vessel anatomical abnormality, that involve either a shunt between an artery and a vein, an abnormal blood vessels structure or both.

Vascular malformations are divided into two sub-categories: High Flow Malformations, which comprise of Arteriovenous Malformations (AVMs) and Arteriovenous Fistulas (AVFs), and/or Low Flow Malformations, which comprise of Venous Malformations (VMs), Capillary Malformations (CMs), and Lymphatic Malformations (LMs). There pathologies possess several risk factors, while the main clinical risk is hemorrhage—especially within the High Flow Vascular Malformations. A significant risk factor within the Low Flow Vascular Malformation is clotting—which might appear in a Venous Malformation due to local turbulences, as the vessels' smooth muscle abnormal structure prevented it from attaining its primary target—drop of blood pressure and velocity.

Treatment modalities defer from one pathology to another, and vary from Surgical recession, Laser ablation (to superficial LFVMs only), embolization and/or radiotherapy procedures[3].

Hemangiomas are vascular anomalies that comprise of local benign tumors which show a local anatomical structure featuring abnormal blood vessels—both anatomically and histologically—regarding their large number of unique endothelial cells. While most Hemangiomas are not dangerous, some do cause clinical risks such as Ophthalmic, Hepatic and/or Cardiac Hemangiomas.

Chronic Venous insufficiency (CV/) 4 comprises retrograde blood flow at the peripheral venous system, originating mainly from incompetence of valves. The pathophysiological pathway initiates from the inability of a valve to close properly and obtain antegrade flow only, thus creating local reflux. The pressure down the path of an affected valve. In some embodiments, affecting additional valves as well and causing regional venous hypertension. The pathology can occur at the superficial, perforating or deep venous levels. Deep Venous Insufficiency (DVI)[5] ar. In some embodiments from incompetence of the deep venous valves due to congenital abnormalities or post thrombotic damage. The pathology indicates in rise a dramatic rise of hydrostatic venous pressure. No treatment for Deep Venous.

Insufficiency has been proved to be both safe and effective at a large-scale trial.[6] This is significant, since a patient with indications for DVI and SVI is difficult to treat, despite the efficacy of SVI treatments.

Heart Valve Insufficiency Regurgitation 7 is a condition where one of the heart valves is not fully sealed while closed, thus allowing a portion of the pumped blood to backflow. The pathology may occur in each of the heart valves—Aortic, Mitral (left heart disease oriented), Tricuspid or Pulmonary (right heart disease oriented). The leakage causes less blood to reach the aorta at each stroke, as well as increased turbulence at the affected area. Thus, the heart work for sustaining tissue oxygen levels despite the leakage is chronically increased, results in a variety of symptoms, most related to heart failure—dyspnea, chest pain, edema, palpitations and more. When reaching dangerous levels, the valve is treated or replaced surgically.

For example, we will describe in detail a pathology that has a significant potential to benefit from the device/method, due to the limitations of existing therapy possibilities.

Arteriovenous Malformation (AVM)[8] is a congenital disorder characterized by a complex, tangled Web of arteries and veins. An AVM may occur in the brain, brainstem, or spinal cord of a mammal or may be at a different anatomical site such as in the pelvic areas, limbs, heart, lungs, etc. and is caused by abnormal development of blood vessels. The most common risk of AVM is hemorrhaging (bleeding). AVMs of the brain cause symptoms such as, brainstem or spinal cord, seizures, headaches, and neurological problems such as paralysis or loss of speech, memory, or vision. The symptoms of AVMs are often due to circulatory "steal" or insufficiencies caused by the AVM. AVMs, particularly those located in the brain or spine of mammals (humans), are difficult or dangerous to treat[9,10]. Cerebral AVMs, for example, are most commonly discovered in young human adults aged 20-40 years. These lesions are usually detected in patients as the result of a seizure or hemorrhage. AVMs hemorrhage at a rate of 4% per year (meaning—a 28% hemorrhaging rate after 10 years).

Approximately half of these hemorrhages will carry significant morbidity or mortality[10] and, accordingly, the lifetime risk of hemorrhage can be substantial. Treatment of AVMs has employed a team approach utilizing combined modality therapy. Three modalities of treatment heretofore employed include endovascular introduction of tissue glues which occlude parts or all of the AVM, microsurgical techniques to remove the AVM or radiosurgery (focused radiation) to ablate the AVM. Combined modality therapies include a first reduction of the AVM via endovascular introduction of tissue glues followed by stereotactic radiosurgery where a focused beam of radiation is used on a one-time treatment basis at a dose of from about 10 to 30 Gy With an average dose of about 20 Gy. This radiation causes changes in blood vessel Walls, and over the course of 2-3 years the remainder of the AVM can be obliterated. This technique is most effective in smaller lesions (diameters less than 2.5 cm). Obliteration rates of up to 85% have been reported by two years after treatment. The risk of injury to surrounding normal tissue (e. g., brain tissue) is significant and is dependent upon the dose and focus of the radiation used which is kept to minimal levels to prevent collateral damage to healthy tissue. Notwithstanding the benefits of a team approach of combined modalities for the treatment of AVMs, such a team approach requires an average of 2.6 separate medical procedures on the patient. Accordingly, simpler procedures to effect treatment of AVMs Would be particularly beneficial.

At the current time, treating AVMs with the current modalities do not solve all of the pathology related problems, and even create new ones. The first issue is that even though the bigger nidus sized AVMs should necessitate a higher intervention rate, the feasibility of treatment is in favor of smaller AVMs.

(76% of those with a nidus <30 mm are treated, compared with ~57% of those 30 to 59 mm and ~14% of those >60 mm.[8]

Moreover, Embolism, which is one of the prevalent treatment methods, necessitates a series of interventional sessions (up to 11 with an Avg of 2.6). Each session includes hospitalization for a minimum of 2 days, the use of advance imaging modalities, general anesthesia and a high-risk operation. This interventional operation exhibits a 2.7% chance for significant neurological complications in each session immediately after embolization. In addition, there is a permanent morbidity rate of 3%-14%.[8]

However, Embolism is not recommended as a single-modality therapy, due to a low obliteration likelihood (11-40%)[8], and is usually done along with radio surgery. Radiosurgery takes 1-3 years to achieve thrombosis, and cure is not always obtained. Thus, the patient remains at risk for hemorrhage from AVM during the treatment period.

In a study done on 300 patients in the US at 2011[8], about 18% of the people that were treated got worse and 6% died.

Brachytherapy

Brachytherapy is a form of radiotherapy, where the radiative source (isotope) is sealed within a capsule and manually placed within or at the vicinities of the anatomical area meant for treatment.

The common uses for Brachytherapy are mainly oncologic and involve cervical, prostate, breast, skin cancer—but not limited to these locations.

The encapsulated source emits x-ray, gamma or beta radiation at prescribed doses and thus causes the desired effect on the surrounding tissues—most commonly inflicting radiation related injuries[11] at tumors and thus shrinking or obliterating it.

The biological controlling mechanism is direct damage to the tissue, which causes scarring and fibrotic tissue formation at the injury sites, and thus neutralizing the primary function of the affected area.

This biological mechanism are similar to those activated in the AVM treatment state of the art Stereotactic Surgery (Radioactive surgery for AVM's), where a focal beam locally ablates a blood vessel's tissue and causes injury and blockage by fibrotic tissue.

The doses in Brachytherapy can be roughly divided into two segments: Low Dose Radiation[11,12] and High Dose Radiation[11,12] Brachytherapy methods. The first comprises of a seed placement at the desired area, and a slow release of radiation from the seed to the surrounding tissue, producing the desired outcome over weeks/months. The latter comprises of a temporary seed placement at the desired area, release of the entire dose of the desired radiation amount within hours and extraction of the seed.

It is important to note that on both treatment strategies, the desired biological effect is injury and scarring of the tissue—while the LDR relies on the continues injury—fibrosis cycle that will, eventually, kill the tumor, the HDR relies on a concentrated damage and focused trauma to the tumor structure.

The LDR is commonly administered at the intracellular matrix at the tumor and/or on its vicinities—a placement strategy known as "Interstitial Brachytherapy". The HDR seed is mainly inserted via a specifically designed catheter/guide tube into a blood vessel in or at the vicinities of the tumor—a placement strategy known as "Intraluminal Brachytherapy", "Vascular Brachytherapy" or "Intravascular Brachytherapy".

In some embodiments, methods and/or devices e.g. as described within this document are used to treating tumors, vascular malformations and vascular pathologies e.g. by eliminating their blood supply and/or restoring vascular physiological functionality by reshaping a vessel/valve anatomy, by partially or completely blocking their lumen by eliciting Tunica Intima/Media cells hyperplasia reactions to a low dose ionizing radiation via radioactive compositions. These compositions are delivered to one or more vascular sites of the tumor/malformation in a mammal as one embodiment of an anchor with a radioactive mass.

The radiation regime of some preferred embodiments follows a micro injury the site location endothelial cells, which allows a full potential of the desired effect by encouraging migration of smooth muscles cells to the injury sites and enhancing the cell hyperproliferation that is performed by the low dose radiation.

The radiation regime in one embodiment includes an initial vascular exposure to ethanol/OK-432 (Picibanil)/Glycerin/Polidocanol/Hypertonic Saline/STS or other irritating agents known in the art of Sclerotherapy that creates micro injuries at the vascular, thereby creating smooth muscles cells migration to the injury sites and allowing enhanced hyperplasia. This should result in further obliteration of the tumor and exhibit cell growth inside the lumens of the tumor's blood vessels, or local lumen decrease for vascular/valvular repair. The continuous low dose radiation exposure strategy approach reduces the number of steps required to effectively treat a tumor. For example, this method/device provides a one-step treatment plan for treating AVMs.

Another embodiment for the initial vascular injury includes an initial high dose exposure for a limited amount of time, that will irritate the Tunica Intima's endothelial layer.

Our method/device for treating tumors can be related as a new and unique form of Intraluminal Brachytherapy, and it differs from the state of the art brachytherapy in at least two aspects:

The outcome of the radiation regime is tunica media/neointimal hyperproliferation, rather than tissue injury.

The strategy of the radiation regime is blood vessels blockage, rather than direct tumor damage.

As stated, we propose An Endothelial Hyperproliferation method and device using a Low Ionizing Radiation regime at a tumor (for example, an AVM's nidus), or for vascular disease (for example, an insufficient deep vein valve) in order to induce a fast paced growth of the tunica intima layer of the blood vessels within its perimeters and thus to cause a complete or partial blockage of the vessels via cellular proliferation mechanisms.

The proliferative response is expected at a defined volume within each radiation source, according to the radiation source intensity, half life time, and source type/geometry.

The effect differs from the outcomes of the state of the art Stereotactic Surgery strategy, which induces a local ablation via significantly higher doses from an external source—and cause a possible vessel blockage via fibrotic mechanisms,[13,14].

Radiation Isotopes and Regime

The radiation emitted from each source (which will be described at the embodiments section) is to be defined as a Low Dose Ionizing Radiation, both at the overall cumulative and the local hourly resolutions. This is defined by the radiative element type and quantity within the source, sources quantity and placement, or any other strategy that influences the potential radiation levels within the tumor.

Overall cumulative (total dosage) radiation that are expected to induce a proliferative effect over a blood Bessel levels include, but not limited to, a range of 10 to 35 Gy.[15]

Hourly dosages include, but not limited to, Initial radiation levels of 100 mGy/hour.

Meaning, any vessel segment that will be exposed to the stated range (possibly followed by minor injury to the endothelial cells) is expected to undergo a Smooth Muscle Cells proliferative response, causing a partial or complete blockage of that vessel.

Radiation sources will emit beta or gamma radiations.

a list of isotopes that can be used as a hyperproliferation inducing factor:

In some preferred embodiments, a radiation source contains 135Iodine gamma radiating isotope.

Another embodiment contains 192Irridium gamma emitting isotope.

Another embodiment contains 32Phosphorus beta emitting isotope.

Additional Radiation emitting isotopes ("isotopes") include any isotope known in the art, examples: 198gold, 125iodine, 137cesium, 55ocobalt, 55cobalt, 56cobalt, 57cobalt, 57magnesium, 55iron 57magnesium, 5Siron, 32phosphorus, 90strontium, 81rubidium, 2O6bismuth, 67gallium, 77bromine, 129cesium, 73selenium, 72selenium, 72arsenic, 1O3palladium, 2O3lead, 111ilindium, 52iron, 167thulium, 57nickel, 62Zinc, 63copper, 201thallium and 123iodine, or any other source used in radiological, oncological, neurosurgical or nuclear medicine.

The said device can contain one or more isotope, according to each embodiment.

Radiation Encapsulation Embodiments:

Seed—

A preferred embodiment can be a seed planted within or at the periphery of a blood vessel located within or at the proximity of the target site (for example—an AVM nidus's feeding artery).

Another embodiment can be a seed planted on a stent at the proximity of a venous or heart valve base.

Another embodiment is a seed planed within or at the proximity of a venous or heart valve base.

A seed is a geometric element containing the said Radiation sources (isotopes), as well as a solid or mixed material used to contain the isotope. The seed is designed to be used as an emitting source for the isotope, according to the desired radiation levels across the tumor and throughout the treatment duration.

Geometry:

In a preferred embodiment, the seed's geometry is cylindrical.

The seed shapes can be spherical, cylindrical, elliptic, or a combination of the three (for example—a cylinder with two spheric edges)—view FIG. 12—schematic of seed+anchoring device Relative Intensities:

The radiation relative intensity, as a function of a spherical angle, can be unified, normally distributed relative to the center, or any other relative distribution.

The volumetric relative intensity can be defined via the seed geometry, or by the isotope placement spreading at the seed surface/within the seed.

In a preferred embodiment, the isotope is uniformly distributed so that the radiation intensity across the source's outer boundaries will be roughly unified. view FIGS. 4B-F—radiation spread examples (simulated)

Materials—the seed material can be any material known to the art of Brachytherapy and as a medically intended radiation source containment, and include, for example—gold, titanium, stainless steel, nitinol, or platinum.

Anchoring Techniques:

Seed anchoring techniques can be any technique known in the arts of Vascular Brachytherapy/Intravascular Brachytherapy and angioplasty, Vena cava filters, endograft anchoring.

A preferred embodiment includes a Nitinol/Stainless Steel/Cobalt Chromium wire that creates an "8 shape" geometry, while the seed is placed at the center (view FIG. 12). This geometry allows a solid anchoring to the blood vessel's interior wall with an adaptation to its inner lumen diameter.

Another embodiment includes an array of wires arranged at the "8 figure" geometry shown in FIG. 12, additional wires covering contact points, thus enhancing the anchor stability (view FIG. 13).

Sources delivery embodiments—The delivery embodiment can be any Vascular Brachytherapy/Intravascular Brachytherapy catheter used in the art, also known as a "guide tube", "Delivery Catheter".

Source Manufacturing:

The Seed, containing the said isotope, can be manufactured by any way known in the art at the field of Brachytherapy.

In a preferred embodiment, the source consists of the said isotope is singly encapsulated in stainless steel and welded to means of the said means of anchoring.

In other embodiments, the encapsulation within the seed can be at the surface of the seed, at a trapped layer between two material layers and (a shell), or mixed within a selected material to produce the desired distribution across the seed.

In another embodiment, a seed encapsulation assembly can be made from a degradable material. The material can be an oxidized regenerated cellulose or other biodegradable materials with the radioisotope either embedded within the strands or coated onto the outer surfaces of the strands.

In another embodiment, the isotope containing source is a stent or Anchor.

The stent geometric features can be any known in the art of angioplasty—cerebral, cardiovascular or peripheral.

In one embodiment, the said isotope is integrated within the stent uniformly.

In another embodiment, the isotope is encapsulated within the said seed, while the stent acts as an anchoring system only as it contains no isotope and attached physically to the said seed.

In another embodiment, the isotope is encapsulated within a stent tip, at the vicinities of an affected venous or heart valve, while the body of the stent acts as an anchoring system alone.

In another embodiment, the isotope is encapsulated within a stent tip, at the vicinities of an affected venous or heart valve, while the body of the stent acts as an anchoring system as well as a physical barrier for preventing excessive tissue accumulation at the base of the valve due to hyperproliferation, or any other reason.

In another embodiment, the isotope containing source is a wire.

The wire's geometric and delivery methods can be any of the techniques known in the art of endovascular coiling.

In one embodiment, the said isotope is integrated within the stent uniformly.

In another embodiment, the isotope is encapsulated within the said seed, while the wire acts as an anchoring system only as it contains no isotope and attached physically to the said seed.

In another embodiment, the isotope containing source is any polymer know in the art of embolization.

In one embodiment, the said isotope is integrated within the polymer uniformly.

In another embodiment, the isotope is evenly distributed within the said polymer, while the desired effect is caused after an initial embolization.

Operation

Preferred Radiation Treatment Protocol:

The seed, when placed within a blood vessel within/at the vicinity of a tumor (for example—an artery within an AVM nidus)/at the vicinity of a venous or heart valve (for example—deep venous valve), contains an isotope that emits x-ray, gamma or beta radiation. The radiation decreases exponentially both at the space and the time variables.

According to numerous experiments,[15,16,17] where the response of blood vessels to radiation regime (mainly irradiating stents) was tested, a surprising result of SMC hyperproliferation was found at the total dosage rate of 10-35 Gy e.g. with a top hourly rate of 100 mGy/hour.

This in contradiction to the expected result of endothelial permanent damage and fibrosis.

According some exemplary designs (view FIGS. 4B-F—example of radiation regime changes over time simulation), the seed—once placed within a blood vessel—will begin to irradiate the surrounding tissues, while the endothelial cells found at the proliferative response inducing values of the radiation regime—both total and hourly—are likely to hyperproliferate and cause a partial or a complete blockage of their vessel segment.

This way, each seed will create defined volume of blocked blood vessels, and stop the blood flow locally into the tumor. The spatial combination of seed placement will be done according to the treatment strategy, with methodologies known in the art of brachytherapy.

In some embodiments, a treatment protocol includes an initial microscopic injury to the site's Tunica intima/Tunica Media. This is done in order to further enhance the hyperproliferation effect by attracting SMC cells to the injury sites, and trigger Hyperplasia at all of the said sites.

In some embodiments, a preferred method for causing the micro endothelial injuries is usage of an irritating medium, injected to the site prior/immediately after the seeds' anchoring at the site.

The irritating fluid main embodiment is a diluted Ethanol/OK-432 (Picibanil)/Glycerin/Polidocanol/Hypertonic Saline/STS or other irritating agents known in the art of Sclerotherapy combined with a radiopathic agent, which causes endothelial injuries and used at the art of AVM embolization at high concentration in order to cause direct embolization.[18] For example—Picibanil with non-ionic contrast medium such as Iobytridol-xenetix 300, guerbet, cedex, france.

The irritating fluid injection is done by any mean known at the art for embolization and/or minimally invasive angiography.

Thus, the desired area for treatment is both irritated—creating the said micro injuries which serve as a basis for the large scale hyperplasia, and marked for imaging.

Additional Radiation Treatment Strategy:

In another embodiment, the radiation regime will include, instead of a micro injury strategy caused by an irritating agent, an initial high dose of irradiation—for a microscopic sporadic injury of endothelial cells within the radiation regime volume. As said, an initial microscopic injury enhances the hyperproliferation process by encouraging migration of smooth muscles cells into the injury sites. These, along with the cellular growth factors that are being induced in the process of low dose radiation exposure, are likely to cause additional proliferation at and near the micro injuries sites—and produce a faster blockage.

As seen in histological analyses[17], the irradiated sites (only the sites that were exposed to the hourly and cumulative dosages that caused the hyperproliferation effect) show a significant increase in neointima compared to control sites—containing smooth muscle cells, as well as inflammation related material and cells. This puts further evidence on the significance of the initial injury as a catalyzer for the hyperproliferation effect.

The radiation amount needed for tissue microscopic injuries is known in the arts or intravascular brachytherapy, as well as stereotactic neurosurgery.

Seed Insertion and Placement

When treating a tumor/Vascular malformation, the seed can be placed at the center of the tumor, its periphery or its vicinities—all according to the tumor's treatment strategy chosen by the clinician. In some embodiments, it is preferred to place the seed at the center of the nidus in order to cover as much volume for each seed.

When treating valvular insufficiency, the seed can be placed at the proximity of the affected valve via using one or more of the following methods:

Placing the seed on a stent that is anchored at the vicinity of the affected valve.

Placing the seed on an anchor that is anchored at the vicinity of the affected valve.

Placing the seed directly at the Tunica intima or tunica media or tunica externa layers, or at any chosen anatomical location by the clinician.

This is done in order to elicit the said hyperproliferative response at the valve's base.

The catheter seed insertion systems, as well as seed localization, are well known in the art of intravascular brachytherapy.

Any of the said isotopes can be used as a marker for a feedback to the clinician regarding seed placement within a blood vessel.

General

It is expected that during the life of a patent maturing from this application many relevant vascular treatment methods and devices will be developed and the scope of the term vascular treatment is intended to include all such new technologies a priori.

As used herein the term "about" refers to ±20%

The terms "comprise", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

What is claimed is:

1. A method of treatment comprising:
    selecting tissue to be exposed to radiation for gradual closure of one or more blood vessel within said tissue to be exposed to radiation;
    selecting therapeutic window radiation levels to promote gradual constriction of said one or more vessel;
    providing a device comprising:
        a body; and
        one or more radiation sources coupled to said body and configured to form said therapeutic window radiation levels at a separation greater than zero and less than 30 mm from said one or more radiation sources;
    positioning said one or more radiation sources away from said body and at a distance from said selected tissue to be exposed to radiation, where the only tissue where said therapeutic window starts is blood;
    exposing said tissue to be exposed to radiation to selected radiation levels emitted from said one or more radiation sources.

2. The method according to claim 1, wherein said selecting comprises selecting said radiation levels to promote said constriction by one or more of:
    hyperproliferation of cells of said one or more blood vessel; and
    negative remodeling of said one or more blood vessel.

3. The method according to claim 1, wherein said selecting radiation levels comprises planning a spatial distribution of said one or more radiation sources to provide radiation within a therapeutic window over a geometry of said selected tissue.

4. The method according to claim 1, wherein said gradual closure is over a time period of 1 week to 6 months.

5. The method according to claim 1, wherein an effect of said radiation on said tissue to be exposed to radiation is asymmetrical.

6. The method according to claim 1, wherein said gradual closure is for the treatment of one or more of: tumor feeding blood vessels; angiogenesis; vascular anomaly; vascular malformation (AVM); hemangioma; chronic venous insufficiency (CVI); valve malfunction; deep vein thrombosis; varicocele; aneurysm.

7. The method according to claim 1, wherein said one or more radiation sources comprise one or more seed comprising encapsulated radioactive material.

8. The method according to claim 1, comprising:
    selecting tissue to be injured; and
    injuring said tissue to be injured, where said tissue to be exposed to radiation has a different extent to said tissue selected to be injured.

9. The method according to claim 1, wherein said positioning comprises anchoring said device to tissue while keeping said one or more radiation sources at a distance from said tissue.

10. The method according to claim 9, wherein said anchoring comprises expanding a structure coupled to said one or more radiation sources within a vessel, while keeping said one or more radiation sources at a distance from a wall of said vessel and said tissue to be treated;
    wherein said vessel is a vessel to be treated or a vessel proximal to tissue to be treated.

11. The method according to claim 10, wherein said structure, when expanded is shaped to anchor said structure at axially separated locations along said vessel allowing at least 0.1 mm between these locations for luminal collapse on said structure.

12. The method according to claim 1, wherein said positioning of said one or more sources and
    said one or more sources themselves are configured to emit radiation levels suitable to cause gradual closure of said one or more blood vessel at a distance of less than 30 mm from said one or more sources.

13. The method according to claim 1, wherein said one or more- sources has an activity of 0.01-20 mCi.

14. The method according to claim 1, wherein said one or more sources is part of an element configured to anchor said device within a lumen or is said element.

15. The method according to claim 1, wherein said one or more radiation source emits one or more of alpha, beta and gamma radiation.

16. The method according to claim 1, wherein said one or more radiation sources emits gamma radiation.

17. The method according to claim 1, wherein said constriction is to an extent that promotes closure of said one or more vessel.

18. The method according to claim 1, comprising:
injuring said tissue to be exposed to radiation, prior to said exposing.

19. The method according to claim 18, wherein said injuring comprises one or more of injuring via:
application of one or more sclerosing agent;
mechanical injury;
temperature change;
irradiation;
ultrasound;
radiofrequency (RF).

20. The method according to claim 1, wherein said positioning comprises positioning said one or more radiation sources at a distance from said selected tissue to be exposed to radiation, so said one or more radiation sources are surrounded by blood.

21. The method according to claims 1, wherein said one or more radiation sources has an activity of 1-15 µCi.

22. The method according to claims 1, wherein said one or more radiation sources is configured to emit a radiation dose of 0.1-120 Gy.

23. The method according to claims 1, wherein said one or more radiation sources is configured to emit a radiation dose of 1-60 Gy.

24. The method according to claim 1, wherein said distance is greater than zero.

25. The method according to claim 1, wherein said distance is more than 1 mm.

26. The method according to claim 1, wherein said method comprises anchoring said device to a blood vessel wall.

27. The method according to claim 1, wherein said body is an expandable body, said method comprising:
expanding said expandable body to position said one or more radiation sources at said position away from said body and at said distance from said selected tissue to be exposed and within in a central region of said device.

* * * * *